(12) United States Patent
Milner et al.

(10) Patent No.: US 8,125,648 B2
(45) Date of Patent: Feb. 28, 2012

(54) POLARIZATION-SENSITIVE SPECTRAL INTERFEROMETRY

(75) Inventors: Thomas E. Milner, Austin, TX (US); Nathaniel J. Kemp, Austin, TX (US); Eunha Kim, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 366 days.

(21) Appl. No.: 12/131,825

(22) Filed: Jun. 2, 2008

(65) Prior Publication Data

US 2008/0291463 A1     Nov. 27, 2008

Related U.S. Application Data

(63) Continuation-in-part of application No. 11/446,683, filed on Jun. 5, 2006, now Pat. No. 7,783,337.

(60) Provisional application No. 60/932,546, filed on May 31, 2007.

(51) Int. Cl.
G01B 9/02  (2006.01)
(52) U.S. Cl. .................................................. 356/497
(58) Field of Classification Search .................. 356/450, 356/456, 491, 364, 497
See application file for complete search history.

(56) References Cited

U.S. PATENT DOCUMENTS

| | | | | |
|---|---|---|---|---|
| 6,134,033 A | | 10/2000 | Bergano et al. | 359/122 |
| 6,208,415 B1 * | | 3/2001 | De Boer et al. | 356/450 |
| 6,463,313 B1 * | | 10/2002 | Winston et al. | 600/407 |
| 6,501,551 B1 * | | 12/2002 | Tearney et al. | 356/477 |
| 6,961,123 B1 | | 11/2005 | Wang et al. | 356/364 |
| 7,177,491 B2 * | | 2/2007 | Dave et al. | 385/11 |
| 7,256,894 B2 | | 8/2007 | Chen et al. | 356/497 |
| 7,359,062 B2 | | 4/2008 | Chen et al. | 356/479 |
| 2005/0213103 A1 * | | 9/2005 | Everett et al. | 356/479 |
| 2006/0241493 A1 | | 10/2006 | Feldman et al. | 600/476 |
| 2007/0015969 A1 * | | 1/2007 | Feldman et al. | 600/160 |
| 2007/0045471 A1 | | 3/2007 | Erben et al. | 244/129.4 |

FOREIGN PATENT DOCUMENTS

WO     2004/096049     11/2004

OTHER PUBLICATIONS

International Search Report, pp. 1-3 (Jun. 17, 2009).
Written Opinion of the International Searching Authority, pp. 1-5 (Jun. 17, 2009).
Chen, et al., "Laser-based Microscale Patterning of Biodegradable Polymers for Biomedical Applications", International Journal of Materials and Product Technology, vol. 18, No. 4/5/6, pp. 457-468, (2003).
Chen, et al., "Melting and Surface Deformation in Pulsed Laser Surface Micromodification of Ni-P Disks", Journal of Heat Transfer, vol. 122, pp. 107-112, (Feb. 2000).
Davies, et al., "Plaque Fissuring—The Cause of Acute Myocardial Infarction, Sudden Ischaemic Death, and Crescendo Angina", British Heart Journal, vol. 53, pp. 363-373, (1985).

(Continued)

*Primary Examiner* — Hwa Lee

(74) *Attorney, Agent, or Firm* — J. Peter Paredes; Rosenbaum & Silvert, P.C.

(57) ABSTRACT

A polarization sensitive spectral interferometer apparatus and method for analyzing a sample. The polarization sensitive spectral interferometer apparatus and method determines polarization properties of the sample.

16 Claims, 18 Drawing Sheets

OTHER PUBLICATIONS

Davies, et al., "Risk of Thrombosis in Human Atherosclerotic Plaques; Role of Extracellular Lipid, Macrophage, and Smooth Muscle Cell Content", British Heart Journal, vol. 69, pp. 377-381, (1993).

Feldchtein, et al., "Design and Performance of an Endoscopic OCT System for In Vivo Studies of Human Mucosa", Technical Digest for Summaries of Papers—Conference on Lasers and Electro-Optics Conference Edition, Technical Digest Series, vol. 6, pp. 122-123, (1998).

Feldchtein, et al., "Endoscopic Applications of Optical Coherence Tomography", Optics Express, vol. 3, No. 6, pp. 257-270, (Sep. 14, 1998).

Giattina, et al., "Assessment of Coronary Plaque Collagen with Polarization Sensitive Optical Coherence Tomography (PS-OCT)", International Journal of Cardiology, vol. 107, pp. 400-409, (2006).

Iseri, et al., "Relationship Between Cognitive Impairment and Retinal Morphological and Visual Functional Abnormalities in Alzheimer Disease", Journal of Neuro-Ophthalmology, vol. 26, No. 1, pp. 18-24, (2006).

Jang, et al., "Visualization of Coronary Atherosclerotic Plaques in Patients Using Optical Coherence Tomography: Comparison With Intravascular Ultrasound", Journal of the American College of Cardiology, vol. 29, No. 4, pp. 604-609, (2002).

Jesser, et al., "High Resolution Imaging of Transitional Cell Carcinoma with Optical Coherence Tomography: Feasibility for the Evaluation of Bladder Pathology", The British Journal of Radiology, vol. 72, pp. 1170-1176, (1999).

Jin, et al., "Imaging Linear Birefringence and Dichroism in Cerebral Amyloid Pathologies", Proceedings of the National Academy of Sciences, vol. 100, No. 26, pp. 15294-15298, (2003).

Kancharla, et al., "Fabrication of Biodegradable Polymeric Micro-Devices Using Laser Micromachining", Biomedical Microdevices, vol. 4, No. 2, pp. 105-109, (2002).

Kemp, et al., "Depth-Resolved Optic Axis Orientation in Multiple Layered Anisotropic Tissues Measured with Enhanced Polarization-Sensitive Optical Coherence Tomography (EPS-OCT)", Optics Express, vol. 13, No. 12, pp. 4507-4518, (2005).

Kemp, et al., "Form-Biattenuance in Fibrous Tissues Measured with Polarization-Sensitive Optical Coherence Tomography (PS-OCT)", Optics Express, vol. 13, No. 12, pp. 4611-4628, (2005).

Kemp, et al., "High-Sensitivity Etermination of Birefringence in Turbid Media with Enhanced Polarization-Sensitive Optical Coherence Tomography", Journal of the Optical Society of America A, vol. 22, No. 3, pp. 552-560, (2005).

Kemp, et al., "Fibre Orientation Contrast for Depth-Resolved Identification of Structural Interfaces in Birefringent Tissue", Physics in Medicine and Biology, vol. 51, pp. 3759-3767, (2006).

Kim, et al., "Fiber-Optic Spectral Polarimeter Using a Broadband Swept Laser Source", Optics Communications, vol. 249, pp. 351-356, (2005).

Kim, et al., "Fiber-Based Single-Channel Polarization-Sensitive Spectral Interferometry", Journal of the Optical Society of America A, vol. 23, No. 6, pp. 1458-1467, (2006).

Little, et al., "The Underlying Coronary Lesion in Myocardial Infarction: Implications for Coronary Angiography", Clinical Cardiology, vol. 14, pp. 868-874, (1991) (Abstract Only).

Liu, et al., "Characterizing of Tissue Microstructure with Single-Detector Polarization-Sensitive Optical Coherence Tomography", Applied Optics, vol. 45, No. 18, pp. 4464-4479, (2006).

MacIlwain, Colin, "US Plans Large Funding Boost to Support Nanotechnology Boom", Nature, vol. 400, p. 1, (Jul. 8, 1999).

McAllister, D.V., et al., "Microfabricated Microneedles for Gene and Drug Delivery", Annual Review of Biomedical Engineers, vol. 2, pp. 289-313, (2000).

Nisssen, S., "Coronary Angiography and Intravascular Ultrasound", American Journal of Cardiology, vol. 87, pp. 15A-20A, (Feb. 16, 2001).

Optical Cable Corporation homepage, http://www.occfiber.com, (Oct. 17, 2008).

Polla, D., et al., "Microdevices in Medicine", Annual Review of Biomedical Engineering, vol. 2, pp. 551-576, (2000).

Rabbani, R., et al., "Strategies to Achieve Coronary Arterial Plaque Stabilization", Cardiovascular Research, vol. 41, pp. 402-417, (1999).

Rollins, A.M., et al., "Real-time In Vivo Imaging of Human Gastrointestinal Ultrastructure by Use of Endoscopic Optical Coherence Tomography with a Novel Efficient Interferometer Design", Optics Letters, vol. 24, No. 19, pp. 1358-1360, (1999) (Abstract Only).

Tearney, et al., "Endoscopic Optical Coherence Tomography", SPIE—International Society of Optical Engineers, vol. 2979, pp. 2-5, (1997).

Villard, et al., "Use of a Blood Substitute to Determine Instantaneous Murine Right Ventricular Thickening With Optical Coherence Tomography", Circulation, vol. 105, pp. 1843-1849, (Apr. 1, 2002).

Volker, et al., "Real-Time, High Velocity-Resolution Color Doppler Optical Coherence Tomography", Optics Letters, vol. 27, No. 1, pp. 34-36, (2002) (Abstract Only).

Zheng, et al., "Micro-Manufacturing of a Nano-Liter-Scale, Continuous Flow Polymerase Chain Reaction System", Transactions of NAMRI/SME (North American Manufacturing Research Institution of the Society of Manufacturing Engineers), vol. 30, pp. 551-556, (2002).

\* cited by examiner

POLARIZATION-SENSITIVE SPECTRAL INTERFEROMETRY

CROSS-RELATED APPLICATIONS

The present application claims priority to U.S. Provisional Application Ser. No. 60/932,546, filed May 31, 2007, and claims priority to U.S. patent application Ser. No. 11/446,683, filed Jun. 5, 2006, as a continuation-in-part, both applications incorporated by reference herein.

BACKGROUND OF THE INVENTION

The field of the invention generally relates to optical imaging, and more specifically relates to Optical Coherence Tomography ("OCT") systems and methods.

Spectral modifications resulting from interference of light in, also known as channeled spectra can be observed with various spectral interferometric techniques, commonly consisting of a nonscanning interferometer and spectrometer in the detection path in OCT systems. The superposition of two light beams that are identical except for a relative optical path-length difference L results in a new spectra with ripples that have minima at wavelength λ whenever (n+½)λ=L. If the optical path length difference is constant over the bandwidth of light, the spacing between the adjacent minima of the resultant spectrum in the optical frequency (ν) domain is a constant c/L, where c is the speed of light.

The interference fringes in the spectral domain can be obtained by performing Fourier transform of those recorded in the time domain, distinct differences are recognized between these two measurements. When the optical path length difference between two interfering beams, L=c τ, of the source light is much greater than the source temporal coherence length, high visibility interference fringes are not observed in the time domain. In the spectral domain, however, high visibility fringes are formed irrespective of how long or short the optical path-length difference may be. Additionally, superior sensitivity and signal to noise ratio of spectral interferometry over time-domain approaches are recognized.

Channeled spectra recorded by spectral interferometers have been used to measure absolute distance, dispersion, and both absolute distance and dispersion. By analogy with a two-beam interferometer, the two axes of an optically anisotropic sample or optical fiber can be regarded as two beam paths, while a polarizer placed at the exit end of a sample under test or optical fiber can superpose light from the two beam paths to generate interference fringes in the spectral domain. In practice, polarization control is difficult to realize, since the polarization-mode dispersion in fiber is random and the polarization transformations introduced by fiber components are not common for light in reference and sample paths. Therefore, at the output of the fiber-based polarization-sensitive Michelson, Mach-Zehnder or similar hybrid interferometers, recorded interference fringe signals may contain an unknown time-varying random phase factor due to polarization changes induced by fiber components.

The embodiments described herein solve these problems, as well as others.

SUMMARY OF THE INVENTION

The foregoing and other features and advantages are defined by the appended claims. The following detailed description of exemplary embodiments, read in conjunction with the accompanying drawings is merely illustrative rather than limiting, the scope being defined by the appended claims and equivalents thereof.

A method and apparatus for analyzing a sample. The method and apparatus determines depth-resolved polarization properties of the sample. In one embodiment is a spectral interferometer for analyzing a sample. The interferometer comprises a light source which produces light over a multiplicity of optical frequencies. The interferometer comprises an analyzer that records the intensity of light at the output of the interferometer. The interferometer comprises at least one optical fiber through which the light is transmitted to the sample. The interferometer comprises a receiver which receives the light reflected from the sample. A computer coupled to the interferometer determines depth-resolved polarization properties of the sample.

Another embodiment pertains to a method for analyzing a sample with a spectral interferometer. The method comprises the steps of directing light to the sample with at least one optical fiber of the interferometer. There is the step of reflecting the light from the sample. There is the step of receiving the light with a receiver of the interferometer. There is the step of determining depth and polarization properties of the light reflected from the sample with a computer coupled to of the interferometer.

BRIEF DESCRIPTION OF THE DRAWINGS

The foregoing description of the figures is provided for a more complete understanding of the drawings. It should be understood, however, that the embodiments are not limited to the precise arrangements and configurations shown.

DETAILED DESCRIPTION OF THE EMBODIMENTS

The methods, apparatuses, and systems can be understood more readily by reference to the following detailed description of the methods, apparatuses, and systems, and the following description of the Figures.

Figure 1:
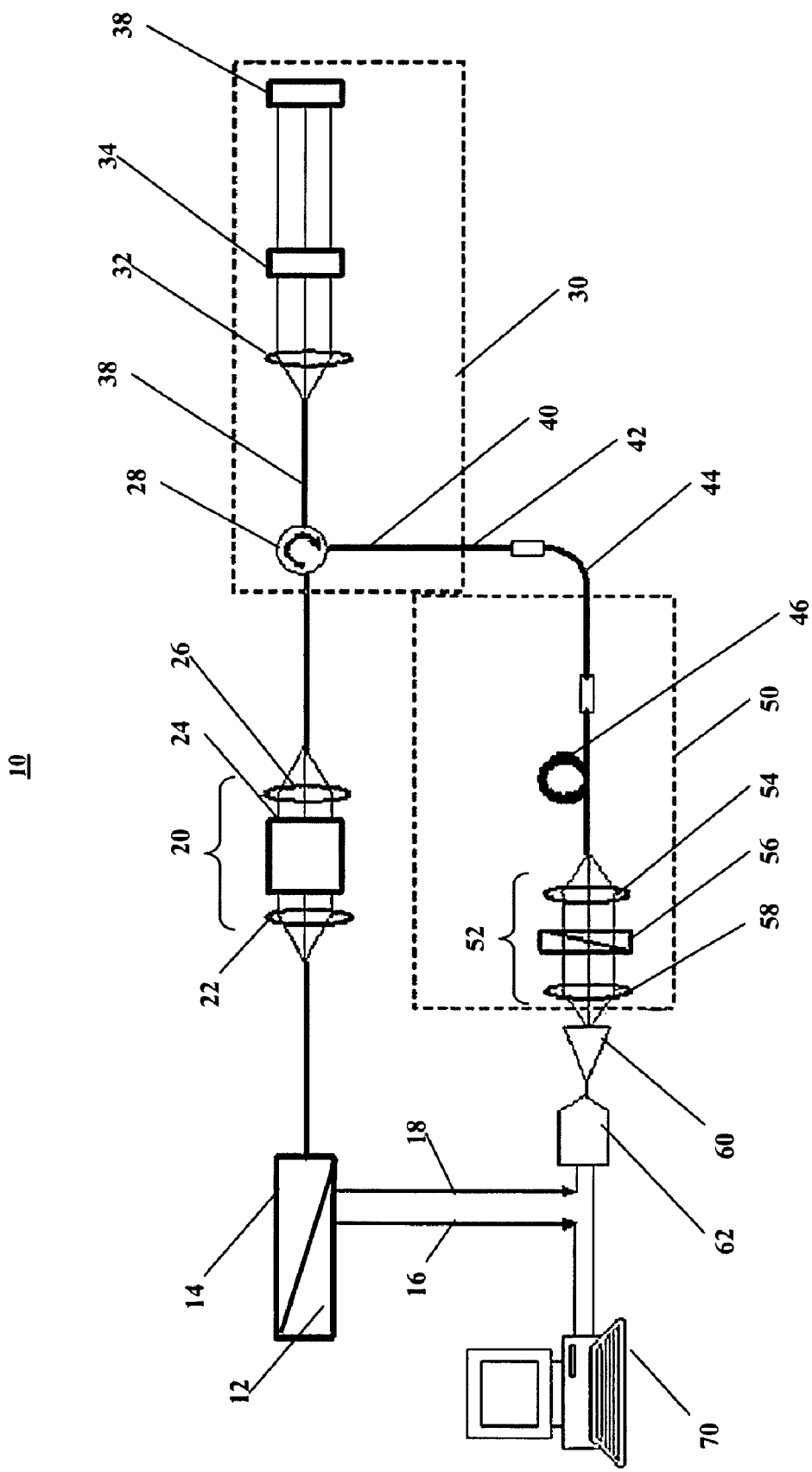
FIG. 1 is a schematic diagram of a polarization-sensitive spectral interferometer in accordance with one embodiment.
Figure 2:
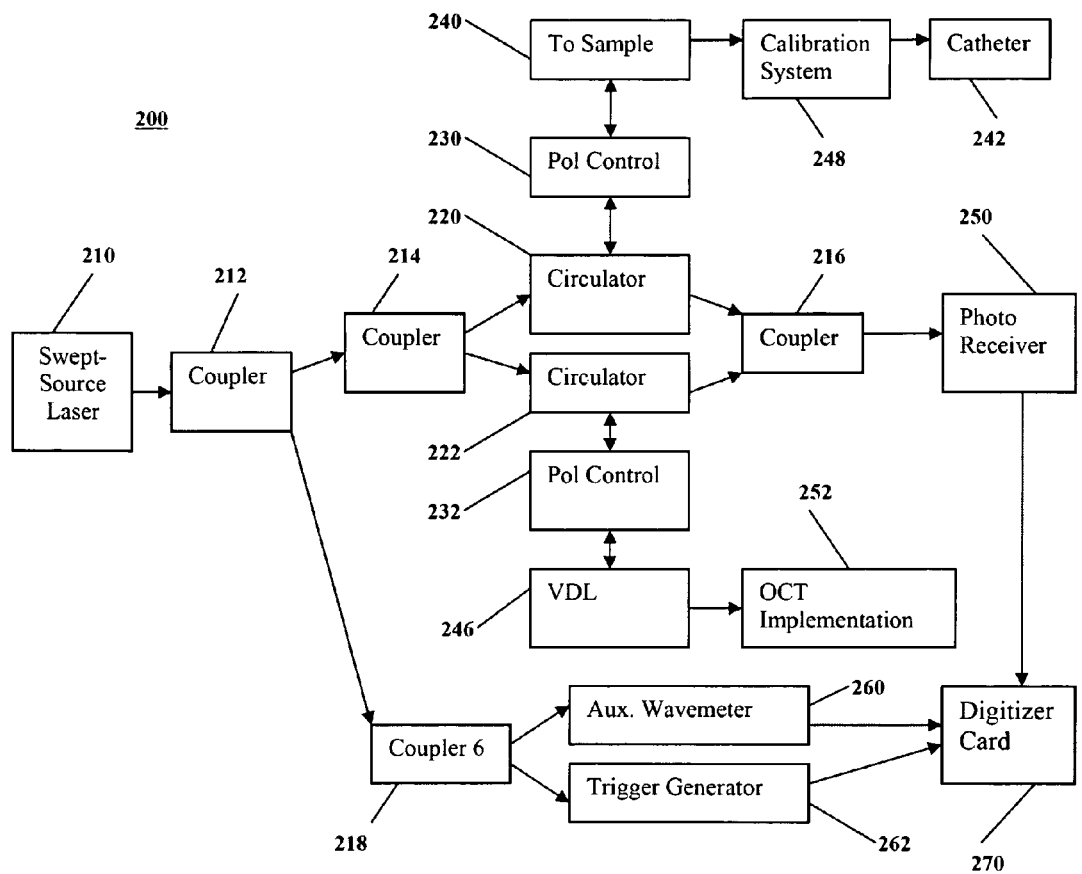
FIG. 2 a schematic diagram of a PS-OCT interferometer in accordance with one embodiment.

Referring now to the drawings wherein like reference numerals refer to similar or identical parts throughout the several views, and more specifically to FIGS. 1 and 2 thereof, there is shown a polarization sensitive spectral interferometer for analyzing a sample. Polarization sensitive spectral interferometer and polarization sensitive Optical Coherence Tomography ("PS-OCT") may be used interchangeably throughout the application. PS-OCT combines polarimetric sensitivity with the high resolution tomographic capability of optical coherence tomography ("OCT") to determine phase retardation (δ) and birefringence (Δn) biattenuance (Δχ) and optical axis orientation (θ). In one embodiment, the PS-OCT configuration includes an interferometer and a light source which produces light over a multiplicity of optical frequencies. The interferometer comprises at least one optical fiber through which the light is transmitted to the sample. The interferometer comprises a receiver which receives the light reflected from the sample. The interferometer comprises a computer coupled to the receiver which determines depth-resolved polarimetric properties of the sample. "Depth-resolved" is may be used in the context of either measuring in the depth dimension or the local variation in a parameter versus depth [e.g., Δχ(z)]".

In one embodiment, the computer coupled to the interferometer determines simultaneously the depth-resolved polarimetric properties of the light reflected from the sample in the interferometer. In another embodiment, the computer determines variations of the polarization of the reflected light as a function of depth of the sample. In another embodiment, the computer determines the depth resolved birefringence of the sample, depth resolved retardation of the sample, depth resolved biattenuance of the sample, and depth resolved optical axis of the sample. The sample is preferably living human tissue, and the reflected light is obtained in vivo in a patient, as described in U.S. patent application Ser. No. 11/466,683 and U.S. patent application Ser. No. 10/548,982, both of which are incorporated by reference herein. The computer preferably identifies tissue type of the sample as a function of depth from the depth-resolved birefringence, retardation, biattenuance and optical axis of the sample. For instance, by maintaining a table look-up in a memory of the computer having a priori information regarding tissue types and their associated birefringence, retardation, biattenuance, and optical axis properties; when unknown tissue is tested using the techniques described herein, the birefringence, biattenuance, retardation, and optical axis properties obtained as a function of depth of the unknown tissue is compared with the known information in the table look-up, and the tissue type as a function of depth is identified. Tissues may include any type of tissue including, but not limited to, arterial vessels and plaques, amyloid plaques and neurofibrillary tangles, aneurysms, urethra, tumors, cartilage, cornea, muscle, retina, nerve, skin and tendon. Alternatively, a follow-up PS-OCT measurement may be employed, looking for changes in birefringence, biattenuance, retardation, and optical axis with the previous measurement(s). Alternatively, the sample may be an optical fiber or general optical element transmitting device under test.

Another embodiment pertains to a method for analyzing a sample with a spectral interferometer. The method comprises the steps of directing light to the sample with at least one optical fiber of the interferometer. There is the step of reflecting the light from the sample. There is the step of receiving the light with a receiver of the interferometer. There is a step of combining or interfering the light reflected from the sample with the light reflected from the reference surface. There is the step of determining depth and polarization properties of the light reflected from the sample with a computer of the interferometer.

In one embodiment, the determining step includes the step of determining simultaneously the depth-resolved polarimetric properties of the light reflected from the sample with the computer. The determining step preferably includes the step of determining variations of the polarization of the reflected light as a function of depth of the sample. Preferably, the determining step includes the step of determining depth resolved birefringence of the sample, depth resolved biattenuance of the sample, depth resolved retardation, and depth resolved optical axis of the sample. There is preferably the step of identifying tissue type of the sample as a function of depth from the depth-resolved birefringence, depth-resolved biattenuance, depth-resolved retardation, and depth-resolved optical axis.

In another embodiment, a polarization-sensitive spectral interferometer generally comprising a broadband frequency-swept laser source, an optical spectrum analyzer ("OSA"), a fiber-based common-path spectral interferometer coupled with a fiber-optic spectral polarimetry instrument ("FOSPI") in the detection path, and photoreceiver. The fiber-based single channel polarization spectral interferometer provides depth resolved measurement of polarization transformations of light reflected from a sample. The range of detectable optical path-length difference using spectral interferometry is proportional to the inverse resolution of the OSA. Algebraic expressions for the Stokes parameters or alternative measure of the polarization state of light—Jones vector or complex Z-parameter, at the output of the interferometer are derived for light reflected from a birefringent sample by using the cross-spectral density function. By insertion of the fiber optic spectral polarimetry instrument into the detection path of a common path spectral interferometer, the full set of Stokes parameters of light reflected from a sample can be obtained with a single optical frequency scan—or improved estimates by averaging multiple optical frequency scans. This embodiment requires neither polarization control components nor prior knowledge of the polarization state of light incident on the sample.

In another embodiment, the interferometer comprises a polarimeter with channeled spectra in spectral polarimetry without polarization control. The polarimeter comprises of a pair of thick birefringent retarders in series with a polarizer and OSA, and a fiber optic spectral polarimetry instrument to measure polarization state of collected light with single optical frequency scan utilizing the principle of the channeled spectral polarimetry. Alternatively, the polarimeter comprises polarization sensitivity that records four sequential single-channel measurements or simultaneous dual-channel horizontal and vertical polarization component measurements in conjunction with a well characterized reference beam. The polarimeter may be utilized to measure the polarization state of light or sample birefringence.

In another embodiment, the fiber-based polarization-sensitive Michelson, Mach Zehnder or similar hybrid interferometer extracts the Stokes parameters of reflected light from a sample from the interference fringe signal recorded in two orthogonal polarization channels. The recorded interference fringe signal includes the phase difference between light reflected from the reference and sample surfaces as well as amplitudes, so polarization-state control of light reflected form the reference surface may be employed. In the common-path spectral interferometer, the phase factor due to polarization changes induced by fiber components is common in light reflected from reference and sample surfaces and cancels in the interference fringe signals recorded in orthogonal channels. In the PS-OCT configurations, the interferometer determines the depth resolved birefringence of the sample, depth resolved retardation of the sample, depth resolved biattenuance of the sample, and depth resolved optical axis of the sample.

Retardation and Birefringence

PS-OCT combines polarimetric sensitivity with the high resolution tomographic capability of optical coherence tomography ("OCT") to determine phase retardation ($\delta$) and birefringence ($\Delta n$) biattenuance ($\Delta \chi$) and optical axis orientation ($\theta$). Noninvasive and invasive determination of $\delta$, $\Delta n$, $\Delta \chi$, and $\theta$ in biological tissue makes the PS-OCT configurations well-suited for clinical diagnostics and biomedical research applications where monitoring of tissue is important. Optical anisotropy properties birefringence ($\Delta n$), biattenuance ($\Delta \chi$), and axis orientation ($\theta$) convey information about the sub-microscopic structure of fibrous tissue (e.g., connective, muscle, nervous tissue, fibrous cap, and the like).

A primary obstacle to high sensitivity determination of tissue retardation and birefringence is polarimetric speckle noise. Speckle noise is common to all imaging modalities that employ spatially-coherent waves (e.g. ultrasound, radar, OCT, etc.). The method to determine accurately polarimetric properties addresses the degrading effects of speckle noise in polarimetric signals detected with PS-OCT configurations. The method comprises the sensitivity required for accurate determination of $\delta$, $\Delta n$, $\Delta \chi$, and $\theta$ in thin tissues with weak birefringence [e.g., primate retinal nerve fiber layer ("RNFL"), $\Delta n \times 10^4$] and/or biattenuance.

The method to determine $\delta$, $\Delta n$, $\Delta \chi$, and $\theta$ comprises multiple incident polarization states and a nonlinear fitting algorithm to determine $\delta$, $\Delta n$, $\Delta \chi$, and $\theta$ with high sensitivity and invariance to unknown incident unitary polarization transformations that may occur in the interferometer. In one example, the "multi-state nonlinear algorithm" is demonstrated in a thin turbid birefringent film.

Form-Biattenuance ($\Delta n$) and Form-Birefringence ($\Delta \chi$)

Form-birefringence ($\Delta n$) in tissue arises from anisotropic light scattering by ordered submicroscopic cylindrical structures (e.g., microtubules, collagen fibrils, etc.) whose diameter is smaller than the wavelength of incident light but larger than the dimension of molecules. Inasmuch as form-birefringence ($\Delta n$) describes the effect of differential phase velocities between light polarized parallel- and perpendicular-to the fiber axis (eigenpolarizations), the term form biattenuance ($\Delta \chi$) describes the related effect of differential attenuation on eigenpolarization amplitudes. Biattenuance ($\Delta \chi$) is an intrinsic physical property responsible for polarization-dependent amplitude attenuation, just as birefringence ($\Delta n$) is the physical property responsible for polarization-dependent phase delay. Diattenuation (D) gives the quantity of accumulated anisotropic attenuation over a given depth ($\Delta z$) by a given optical element.

Optical Axis

Optic axis orientation ($\theta$) provides the direction of constituent fibers relative to a fixed reference direction (i.e., horizontal in the laboratory frame). The PS-OCT configurations measures depth-resolved optic axis orientation [$\theta(z)$] deep within multiple layered tissue using. Using the PS-OCT configurations, the depth-resolved optic axis orientation [$\theta(z)$] unambiguously represents the actual anatomical fiber direction in each layer or depth (z) with respect to a fixed laboratory reference and can be measured with high sensitivity and accuracy. Characterization of the anatomical fiber direction in connective tissues with respect to a fixed reference is important because functional and structural characteristics such as tensile and compressive strength are directly related to the orientation of constituent collagen fibers.

Depth Resolved Identification of Structural interfaces

Depth-resolved curvature ($\kappa(z)$) of normalized Stokes vectors (S(z)) may identify boundaries in multiple-layered fibrous tissue. When contrast in backscattered intensity (I(z)) is not sufficient for identification of lamellar interfaces, the PS-OCT configurations can detect changes in depth-resolved fiber orientation and increases image contrast in multiple layered birefringent tissues. For example, interfaces in the annulus fibrous identified using depth-resolved fiber orientation or the depth-resolved curvature allowed quantification of lamellae thickness. Moreover, the PS-OCT configuration can detect changes in fiber orientation without intense processing needed to effectively quantify tissue retardation and diattenuation.

Cytoskeletal elements, cell membranes, and interstitial collagen impart form-birefringence to tissues such as arterial vessels, amyloid plaques, aneurysms, tumors, cartilage, cornea, muscle, urethra, nerve, retina, skin and tendon. Noninvasive and invasive quantification of form-birefringence, retardation, and optical axis by the PS-OCT configurations 10 and 200 has implications in the clinical management and basic understanding of diseases including but not limited to osteoarthritis, myocardial heart disease, thyroid disease, aneurism, gout, Alzheimer's disease, cancers, tumors, glaucoma, and chronic myeloid leukemia. In addition, changes in form-birefringence may elucidate traumatic, functional, or physiologic alterations such as the severity and depth of burns; wound healing, optical clearing by exogenous chemical agents, or the contractile state of muscle.

Exemplary Polarization Sensitive Spectral Interferometer Configuration

As shown in FIG. 1, in one configuration of the PS-OCT system is a polarization-sensitive spectral interferometer 10 generally comprising a broadband frequency-swept laser source 12, an Optical Spectrum Analyzer ("OSA") 14, a fiber-based common-path spectral interferometer 30, a Fiber-Optic Spectral Polarimetry Instrument ("FOSPI") 50, and a photoreceiver 60. In one embodiment, the broadband frequency-swept laser source 10 operates with a mean frequency of the output spectrum that varies over time. The swept laser source may be any tunable laser source that rapidly tunes a narrowband source through a broad optical bandwidth. The tuning range of the swept source may have a tuning range with a center wavelength between approximately 500 nanometers and 2000 nm, a tuning width of approximately greater than 1% of the center wavelength, and an instantaneous line width of less than approximately 10% of the tuning range with an instantaneous coherence length of over 10 mm. The mean frequency of light emitted from the swept source may change continuously over time at a tuning speed that is greater than 100 terahertz per millisecond and repeatedly with a repetition period. The OSA 14 provides real-time OSA or a clock signal 18 that is used to trigger data acquisition for real-time synchronization of output intensity with optical frequency (v) 16. High spectral resolution of the laser source (or alternatively long coherence length) 12 and the OSA 14 can provide a scan range greater than 10 mm and up to 3 m and allows a flexible system configuration, such as a reference-sample separation up to several centimeters. Selecting optimal optics for the frequency range of the broadband frequency-swept laser source 12 is readily known by those skilled in the art. In one embodiment, the narrowband laser source 12 is swept the over a wide optical frequency range and the optical frequency 16 is optically coupled to a processor 70. The polarization-sensitive spectral interferometer 10 may be based on optical fibers for optically coupling the components thereof.

As shown in FIG. 1, in one embodiment, the swept laser source 12 is optically coupled to an input polarization state preparation optics 20, comprising a lens 22 and a polarizing element 24. The input polarization optics preparation optics 20 allows the preparation of a variety of fixed user-specified states. The light then collected by a lens 26 and transmitted to the fiber circulator 28. The sample and reference beams share a common path 38 in the spectral interferometer 10. This configuration provides automatic compensation for dispersion and polarization difference in the sample and reference paths up to the sample and nearly ideal spatial overlap of reflected sample and reference beams, giving high fringe visibility.

FIG. 1 depicts one embodiment of the common-path spectral interferometer 30 including, the fiber optic circulator 28, a lens 32, a glass window 34 as a reference, and a sample 36 in a common path 38. Emitted light from the source 12 is transmitted to the fiber optic circulator 28, which prevents any unnecessary light loss returning to the source 12 so a fiber based system can be implemented. Emitted light inserted into one port of the circulator 28 is transmitted to a center tap, while the reflected light from the glass window 16 reference and sample 18 is transmitted to the third port of the circulator 22 to a detection path 40. The back surface of the glass window 34 serves as a reference surface. The thickness of the glass window 34 is large enough, so that reflection from the front surface of the glass window does not contribute to the spectral interferogram between light reflected from the reference and that reflected from the sample. In one embodiment, a borosilicate glass window of 6.3 mm thickness is used. In one embodiment, an end facet of the sample path illuminating fiber instead of the glass window 34 can be used in the sample path.

Alternatively, the sample path can be coupled to a probe or catheter via a fiber optic rotary junction. Examples of a rotating catheter tip for the sample path include, a Catheter for In Vivo Imaging as described in 60/949,511, filed Jul. 12, 2007, or an OCT catheter as described in Provisional Application Ser. No. 61/051,340, filed May 7, 2008, each herein incorporated by reference for the methods, apparatuses and systems taught therein. The catheter 242 can be located within a subject to allow light reflection off of subject tissues to obtain optical measurements, medical diagnosis, treatment, and the like. The reference 16 can be coupled to a reflective surface of a ferrule coupled to a lens and rotating prism to provide the common path 38.

Data acquisition is synchronized with calibrated optical clock transitions generated by the OSA 14, so each measured and digitized light intensity corresponds to uniformly spaced or a known optical frequency or spectral component of the spectral interferogram in equation (1).

$$W_{ij}(r;r;v) = W_{ij}^{(1)}(r;r;v) + W_{ij}^{(2)}(r;r;v) + 2R\{W_{ij}(r_1,r_2,v)e^{i2\Pi v\tau}\}, i=j \quad (1)$$

Equation (1) includes autocorrelation terms that arise from interference between surfaces within the sample are not shown. Autocorrelations terms can appear as artifacts and coherent noise; they can be separated from the interference term between the reference and the sample containing useful depth information by shifting the reference and sample containing useful depth information by shifting the reference surface by a distance larger than the sample optical thickness.

$$F^{-1}\{W_{ij}(r;r;v)\} = F^{-1}\{W_{ij}^{(1)}(r;r;v)\} + F^{-1}\{W_{ij}^{(2)}(r;r;v)\} + \Gamma_{ii}(r_1,r_2,t-\tau) + \Gamma^*_{ii}(r_1,r_2,t+\tau). \quad (2)$$

With equation (2), interference fringes can be analyzed by a Fourier transform of the recorded spectrum. Equation (2) is the inverse Fourier transform of Equation (1) with respect to optical frequency v.

As shown in FIG. 1, the detection path 40 includes a first Polarization-Maintaining ("PM") fiber segment 42, a second PM fiber segment 44, and a polarization controller 46 coupled to the FOSPI 50. The first and second PM fibers 42 and 44 are spliced at 45 degrees with respect to each other. The PM fibers are a birefringent optical waveguide that has two orthogonal axes with different refractive indices due to internal stress structures. The first and second PM fiber segments 42 and 44 are used as sequential linear retarders in a retarder system. In one embodiment, the first PM fiber 42 is 2.5 m and the second PM fiber 44 is 5 m. In another embodiment, the use of longer PM fiber segments would allow wider channel separation and provide better estimates of sample phase retardation and fast-axis orientation. The PM fibers are thermally isolated in mechanical enclosures to improve the stability of PM fiber phase retardations. Orthogonal oscillating field components of collected light experience different phase delays due to internal birefringence while passing through the first PM fiber segment 42. At the 45 degree splice 44, both oscillating field components are projected equally on fast and slow axes of the second PM fiber segment 44 and experience different phase delays. Light exiting the second PM fiber 44 segment has four field components with different phase delays depending on the propagation path and passes through an analyzer 36 aligned with the fast axis of the first PM fiber segment 42. All four field components of light are projected onto the transmission axis of the analyzer 36 and produce interference fringes with characteristic time delay (τ) given by the PM fiber segments 42 and 44. In one embodiment, the use of thermally isolated mechanical enclosure improves the stability of PM fiber phase retardations. In one embodiment, the use of longer PM fiber segments allows wider channel separation and provides better estimates of sample phase retardation and fast-axis orientation. The FOSPI is but one implementation of an apparatus to accomplish interference between the different polarization states. Bulk optical elements may accomplish more or less the same objective of the FOSPI. Bulk components may include better stability but the size ranges of optical delays that can be realized are limited, as described in K. Oka and T. Kato, "Spectroscopic polarimetry with a channeled spectrum," Opt. Lett. 24: 1475-1477 (1999), herein incorporated by reference.

The FOSPI 50 includes an analyzer 52 coupled to a photoreceiver 60. In one embodiment, the analyzer 52 includes a collimating lens 54, a polarizer 56, and a lens 58. In operation, output intensity from the common-path spectral interferometer 30 is collected by the FOSPI 50, which is then coupled into the photoreceiver 60 and then input into an analog-to-digital converter 62 that acquires output intensity data by a processor 70 under a LabView™ software interface. By insertion of the FOSPI 50 in the detection path of a common-path spectral interferometer 30, the fall set of Stokes parameters of light backscattered from specific sample depths can be obtained without either polarization-control components in the reference, sample, or detection paths of the interferometer or prior knowledge of the polarization state of light incident on the sample. The OSA 14 provides real-time OSA or clock signal 18 that is used to trigger data acquisition for real-time synchronization of output intensity with optical frequency (v).

Output spectral intensity [$I_{out}$(v)] at optical frequency v emerging from the FOSPI is:

$$I_{out}(v) = 1/2 S_{0,in}(v) + 1/2 \cos\phi_2 S_{1,in}(v) + \quad (3)$$
$$1/2 \sin\phi_1(v)\sin\phi_2(v) S_{2,in}(v) -$$
$$1/2 \cos\phi_1(v)\sin\phi_2(v) S_{3,in}(v)$$
$$= 1/2 S_{0,in}(v) + 1/2 \cos\phi_2(v) S_{1,in}(v) +$$
$$1/4 |S_{23,in}(v)| \cos(\phi_2(v) - \phi_1(v) + \arg(S_{23,in}(v))) -$$
$$1/4 |S_{23,in}(v)| \cos(\phi_2(v) + \phi_1(v) - \arg(S_{23,in}(v)))$$

with $S_{0,in}(v)$, $S_{1,in}(v)$, and $S_{23,in}(v)=S_{2,in}(v)-iS_{3,in}(v)$ representing Stokes spectra of collected light (i.e., incident on the first PM fiber segment 32). The fiber coordinate system utilized to represent the Stokes spectra is oriented so that light oscillating along the fast axis of the first PM fiber segment 34 corresponds to $S_1$=1. Here $\phi_1(v)$ and $\phi_2(v)$ are the phase retardations due to the first and second segments of the PM Fiber 42 and 44 and dependent on optical frequency v, $$\phi_{1(2)}(v) = \frac{2\prod v\Delta n(v)}{c} L_{1(12)}, \quad (4)$$

where Δn(v) is internal birefringence of the PM fiber.

From Equation (3), the output intensity from the FOSPI [$I_{out}$(v)] is a superposition of four Stokes spectra [$S_{0,in}$(v), $S_{1,in}$(v), and $S_{23,in}$(v)=$S_{2,in}$(v)-i$S_{3,in}$(v)] modulated at different carrier frequencies dependent on phase retardations [$\phi_1$(v) and $\phi_2$(v)] in the PM fiber segments. Simple Fourier transformation of $I_{out}$(v) isolates each Stokes spectral component in the time-delay domain (τ) or optical path length difference (cτ) domain. Subsequent demodulation of each peak in the time-delay domain provides the complete set of Stokes spectra [$S_{0,in}$(v),$S_{1,in}$(v),$S_{2,in}$(v),$S_{3,in}$(v)].

When the FOSPI is placed in the detection path of a common path spectral interferometer, two factors determine the spectral modulation. One is the optical path-length difference between reference and sample surfaces, Δ(v), introduced by the common-path spectral interferometer, and the other factor is the phase retardations, $\phi_1$(v) and $\phi_2$(v), generated by the retarder system in the FOSPI. These two factors combine sequentially so that output from the fiber based single channel polarization sensitive spectral interferometer is a convolution of the FOSPI output and that from the common path spectral interferometer.

Computation of the Output Intensity of Interfering Light

When a FOSPI is connected to the detection path of a common path spectral interferometer, an expression for the output intensity of interfering light can be derived. With Equations (25) and (28), measured interference fringe intensity of light from the common path spectral interferometer passing through the FOSPI after reflecting from a birefringent sample is:

$$I_{out}^{(i)}(v) = r_s \cos\Delta(v) \cos\frac{\delta(v)}{2} S_0^{(1)}(v) + \qquad (5)$$

$$r_s \sin\Delta(v\sin)\frac{\delta(v)}{2}(co2\alpha S^{(1)}(v) + \sin2\alpha S_s^{(1)}(v)) +$$

$$\frac{1}{2}r_s\left[\left(\cos\frac{\delta(v)}{2}S_1^{(1)}(v) - \sin\frac{\delta(v)}{2}\sin2\alpha S_3^{(1)}(v)\right) \times \cos(\Delta(v) - \phi_2(v)) + \sin\frac{\delta(v)}{2}\cos2\alpha S_0^{(1)}(v) \times \sin(\Delta(v) - \phi_2(v))\right] +$$

$$\frac{1}{2}r_s\left[\left(\cos\frac{\delta(v)}{2}S_1^{(1)}(v) - \sin\frac{\delta(v)}{2}\sin2\alpha S_3^{(1)}(v)\right) \times \cos(\Delta(v) - \phi_2(v)) + \sin\frac{\delta(v)}{2}\cos2\alpha S_0^{(1)}(v) \times \sin(\Delta(v) - \phi_2(v))\right] +$$

$$\frac{1}{4}r_s\left[\left(\cos\frac{\delta(v)}{2}S_2^{(1)}(v) - \sin\frac{\delta(v)}{2}\cos2\alpha S_3^{(1)}(v)\right) \times \cos(\Delta(v) - \phi_2(v) + \phi_1(v)) + \right.$$

$$\left\{\sin\frac{\delta(v)}{2}\sin2\alpha S_0^{(1)} \times (v) + S_1^{(1)}(v) - \sin\frac{\delta(v)}{2}\cos2\alpha S_2^{(1)}(v) + \cos\frac{\delta(v)}{2}S_3^{(1)}(v)\right\} \sin(\Delta(v) - \phi_2(v) + \phi_1(v))\right] +$$

$$\frac{1}{4}r_s\left[\left(\cos\frac{\delta(v)}{2}S_2^{(1)}(v) + \sin\frac{\delta(v)}{2}\cos2\alpha S_3^{(1)}(v)\right) \times \cos(\Delta(v) + \phi_2(v) - \phi_1(v)) + \right.$$

$$\left\{\sin\frac{\delta(v)}{2}\sin2\alpha S_0^{(1)} \times (v) - S_1^{(1)}(v) + \sin\frac{\delta(v)}{2}\cos2\alpha S_2^{(1)}(v) - \cos\frac{\delta(v)}{2}S_3^{(1)}(v)\right\} \sin(\Delta(v) + \phi_2(v) - \phi_1(v))\right] -$$

$$\frac{1}{4}r_s\left[\left(\cos\frac{\delta(v)}{2}S_2^{(1)}(v) + \sin\frac{\delta(v)}{2}\cos2\alpha S_3^{(1)}(v)\right) \times \cos(\Delta(v) - \phi_2(v) - \phi_1(v)) - \right.$$

$$\left\{\sin\frac{\delta(v)}{2}\sin2\alpha S_0^{(1)} \times (v) - S_1^{(1)}(v) + \sin\frac{\delta(v)}{2}\cos2\alpha S_2^{(1)}(v) - \cos\frac{\delta(v)}{2}S_3^{(1)}(v)\right\} \sin(\Delta(v) - \phi_2(v) - \phi_1(v))\right] -$$

$$\frac{1}{4}r_s\left[\left(\cos\frac{\delta(v)}{2}S_2^{(1)}(v) + \sin\frac{\delta(v)}{2}\cos2\alpha S_3^{(1)}(v)\right) \times \cos(\Delta(v) + \phi_2(v) + \phi_1(v)) + \right.$$

$$\left\{\sin\frac{\delta(v)}{2}\sin2\alpha S_0^{(1)} \times (v) + S_1^{(1)}(v) - \sin\frac{\delta(v)}{2}\cos2\alpha S_2^{(1)}(v) + \cos\frac{\delta(v)}{2}S_3^{(1)}(v)\right\} \sin(\Delta(v) - \phi_2(v) - \phi_1(v))\right].$$

A Fourier transform of Equation (5) gives seven components for each backreflection of light in the positive optical path-length difference domain ($c\tau > 0$), which are centered at $cL_o$, $c(L_o \pm l_{2,o})$, $c(L_o \pm (l_{2,o} l_{1,o}))$, and $c(L_o \pm (l_{2,o} + l_{1,o}))$, respectively, with $\Delta(v) = 2\Pi L_o v + 2\Pi L_1(v)$, $\phi_1(v) = 2\Pi l_{i,o} v + 2\Pi l_{i,1}(v)$.

By computing an inverse Fourier transform of each isolated component in the optical path-length difference domain ($c\tau$), Equations (6-9) are obtained:

$$L_o: \frac{1}{2}r_s e^{i\Delta(v)}\left\{\cos\frac{\delta(v)}{2}S_0^{(1)}(v) - i\sin\frac{\delta(v)}{2}(\cos2\alpha S_1^{(1)}(v) + \sin2\alpha S_2^{(1)}(v))\right\}, \qquad (6)$$

$$L_o + l_{2,o}: \frac{1}{4}r_s e^{i\phi_2} e^{i\Delta(v)}\left\{\left(\cos\frac{\delta(v)}{2}S_1^{(1)}(v) - \sin\frac{\delta(v)}{2} \times \sin2\alpha S_3^{(1)}(v)\right)\right\}, \qquad (7)$$

$$L_o + l_{2,o} - l_{1,0}: \frac{1}{8}r_s e^{i(\phi_2(v) - \phi_1(v))} \qquad (8)$$

$$e^{i\Delta(v)}\left[\left(\cos\frac{\delta(v)}{2}S_1^{(1)}(v) + \sin\frac{\delta(v)}{2}\cos2\alpha S_3^{(1)}(v)\right) - i\left\{\sin\frac{\delta(v)}{2}\sin2\alpha S_0^{(1)}(v) - S_1^{(1)}(v)\right\} + \sin\frac{\delta(v)}{2}\cos2\alpha S_2^{(1)}(v) - \cos\frac{\delta(v)}{2}S_3^{(1)}(v)\right\}\right]$$

$$L_o + l_{2,o} - l_{1,0}: \qquad (9)$$

$$-\frac{1}{8}r_s e^{i(\phi_2(v) + \phi_1(v))}$$

$$e^{i\Delta(v)}\left[\left(\cos\frac{\delta(v)}{2}S2^{(1)}(v) + \sin\frac{\delta(v)}{2}\cos2\alpha S_3^{(1)}(v)\right) - i\left\{\sin\frac{\delta(v)}{2}\sin2\alpha S_0^{(1)}(v) + S_1^{(1)}(v)\right\} - \sin\frac{\delta(v)}{2}\cos2\alpha S_2^{(1)}(v) + \cos\frac{\delta(v)}{2}S_3^{(1)}(v)\right\}\right]$$

The real part of expression (6) gives $S_0^{(i)}(v)/4$, and the real part of expression (7), after the phase shift by $-\phi_2(v)$, gives $S_1^{(i)}(v)/8$. Likewise, $S_2^{(i)}(v)/8$ and $S_3^{(i)}(v)/8$ is obtained by taking the real part of the subtraction of expression (9) from expression (8) and the imaginary part of the sum of expressions (8) and (9) after the appropriate phase shift from the FOSPI, $-(\phi_2(v)-\phi_1(v))$ and $-(\phi_2(v)+\phi_1(v))$ for expressions (8) and (9), respectively. Since the phase retardations $\phi_1(v)$ and $\phi_2(v)$ depend only on the length and birefringence of PM fiber segments, they are calibrated regardless of the unknown polarization characteristics of the sample and polarization state of incident light.

Simple arithmetic gives sample phase retardation ($\delta$) due to the birefringence and the fast axis ($\alpha$ or $\theta$) angle without knowledge of the incident polarization state. The real part of expression (6), the imaginary part of expression (7), and the imaginary part after the subtraction of expression (8) from expression (9) are:

$$\frac{1}{2}r_s \cos\frac{\delta(v)}{2} S_0^{(1)}(v), \qquad (10)$$

$$\frac{1}{4}r_s \sin\frac{\delta(v)}{2} \cos2\alpha S_0^{(1)}(v), \qquad (11)$$

$$\frac{1}{4}r_s \sin\frac{\delta(v)}{2} \sin2\alpha S_0^{(1)}(v), \qquad (12)$$

after phase shifts by $-\Delta(v)$, $-(\Delta(v)+\phi_2(v))$, $-(\Delta(v)+\phi_2(v)-\phi_1(v))$, and $-(\Delta(v)+(\phi_2(v)+\phi_1(v)))$, respectively. $\Delta(v)$ can be obtained from the location of the $S_0^{(i)}$ component in the optical path-length difference domain, assuming dispersion in the sample is small. With a trigonometric identity, Equation (13) is obtained:

$$\tan\frac{\delta(v)}{2} = \frac{2\sqrt{\text{expression}(36)^2 + \text{expression}(37)^2}}{\text{expression}(35)}, \qquad (13)$$

$$\tan\alpha = \frac{\text{expression}(37)}{\text{expression}(36)}. \qquad (14)$$

In this analysis, sample phase retardation ($\delta(z)$) and fast-axis angle ($\alpha$ or $\theta$) can be estimated with the interference fringes and without knowledge of the polarization state of the incident light. When the polarization optics is inserted between the reference and the sample surfaces, the segment can be considered a known portion of the birefringent sample with a specified polarization transformation, and the analysis may be modified to determine the depth-resolved birefringence ($\Delta n$) and fast axis ($\alpha$ or $\theta$) of a sample, as explained in the Optical Axis and Birefringence sections below.

Exemplary PS-OCT Configuration

As shown in FIG. 2, another embodiment of the PS-OCT system can comprise, a Mach-Zehnder interferometer in a PS-OCT configuration 200, which measures the complex mutual coherence function (magnitude and phase) between two non-reciprocal optical paths, one path encompassing an object under test (i.e. "the sample") and the other a reference path. This is in contrast to a Michelson interferometer configuration which measures the same coherence function in a reciprocal configuration (i.e. the same splitter/coupler is used for both input splitting and output recombination). Alternatively, the PS-OCT interferometer can comprise a Michelson interferometer configuration which measures the same coherence function in a reciprocal configuration, i.e. the same splitter/coupler is used for both input splitting and output recombination. The PS-OCT system and calculations for the OCT interferometer is generally described and explained by the inventors in U.S. patent application Ser. No. 11/446,683, and Provisional Application Ser. No. 60/932,546, herein incorporated by reference.

As shown in FIG. 2, The PS-OCT system has a light source 210 with cascaded fiber optic couplers to subdivide the source light into three primary modules (1) the primary OCT interferometer, (2) an auxiliary wavemeter interferometer 260, and (3) an optical trigger generator 262. In one embodiment, the light source 210 is a High Speed Scanning Laser HSL-2000 (Santec) with an instantaneous coherence length of over 10 mm. The swept laser source 210 includes emitted light with a mean frequency of the output spectrum that varies over time. The mean frequency of light emitted from the swept source may change continuously over time at a tuning speed that is greater than 100 terahertz per millisecond and repeatedly with a repetition period. The swept laser source may be any tunable laser source that rapidly tunes a narrowband source through a broad optical bandwidth. The tuning range of the swept source may have a tuning range with a center wavelength between approximately 500 nanometers and 2000 nm, a tuning width of approximately greater than 1% of the center wavelength, and an instantaneous line width of less than approximately 10% of the tuning range. Optionally, the swept laser source 210 is coupled to an electro-optic polarization modulator to modulate the polarization state of the source light periodically in time between two semi orthogonal polarization states.

As shown in FIG. 2, the auxiliary wavemeter 260 and the optical trigger generator 262 are for clocking the swept light source in order for providing an external clock signal to a high speed digitizer 270, as disclosed in commonly assigned application Ser. No. 60/949,467, filed Jul. 12, 2007, herein incorporated by reference. The Uniform Frequency Sample Clock signal is repeatedly outputted for each subsequent optical trigger that occurs as the laser is sweeping and the optical trigger is generated. The optical trigger is generated from the optical trigger generator 262. The high-speed digitizer card 270 is coupled to the output of the OCT interferometer, output of the auxiliary interferometer 260, the trigger signal from the trigger generator 262, and the arbitrary waveform generator. The high-speed PCI digitizer card 270 can be a dual-channel high resolution 16 bit, 125 MS/s waveform for a PCI bus. The external sample clock signal is derived from an auxiliary optical wavemeter photoreceiver during a start-up calibration step, and then repeatedly outputted by the arbitrary waveform generator for each subsequent optical trigger signal that occurs as the laser is sweeping. The external clocking system allows for the wavemeter-generated clock signal to be filtered and processed in software before being outputted on the arbitrary waveform generator. Thus, the external clock derived from the auxiliary wavemeter is regenerated by the arbitrary waveform generator (Gage CompuGen) to allow acquisition of interferometer output data directly in wavenumber (k) space.

Coupler 212 splits 90% of the light source power is split into the primary OCT interferometer and 10% into the coupler 216 for the auxiliary wavemeter 260 and trigger generator 262. A polarization modulator may be placed in the source path to modulate the polarization state of the light source periodically in time between two "semi-orthogonal" polarization states. The modulation cycle may be synchronized to the wavelength scan or during each A-line scan. Coupler 214 then splits the light 90% directed to port 1 of a 3-port polarization sensitive optical circulator 220 for the sample path and 10% of the light is directed to port 1 of a 3-port polarization sensitive optical circulator 222 for the reference path. Port 2 of circulator 220 for the sample path is coupled to a polarization controller 230 and to a sample 240. The polarization controller 230 may include, but is not limited to, a fiber-optic polarization controller based on bending-induced birefringence or squeezing. The polarization controller 230 can be used to match the polarization state of the reference arm to that of the sample arm. Alternatively, the polarization controller 230 may be a polarization control circuit. The sample path can be coupled to a probe or catheter 242 via a fiber optic rotary junction. Examples of a rotating catheter tip for the sample path include, a turbine-type catheter as described in Patent Cooperation Treaty application PCT/US04/12773 filed Apr. 23, 2004; or a rotating optical catheter tip as described in U.S. patent application Ser. No. 11/551,684; or a rotating catheter probe as described in U.S. patent application Ser. No. 11/551,684; or an OCT catheter as described in Provisional Application Ser. No. 61/051,340, filed May 7, 2008, each herein incorporated by reference for the methods, apparatuses and systems taught therein. The catheter 242 can be located within a subject to allow light reflection off of subject tissues to obtain optical measurements, medical diagnosis, treatment, and the like.

The coupler 216 also receives from port 3 of optical circulator 222, where port 2 of optical circulator 222 includes a polarization controller 232 and a Variable Delay Line ("VDL") 246. The VDL 246 comprises of an input fiber, a retro-reflecting mirror on a translation stage, and an output fiber. A dial controls the variable length, or delay, inserted into the optical path. The typical length variance is about 6 cm, while the typical time delay is about 300 picoseconds. Alternatively, an adjustable phase delay system can be included to modulate phase, which includes a piezo-operated stage, to provide much finer phase control, e.g., in the sub-wavelength range. In contradistinction, the VDL provides for larger pathlength adjustments with micron-size adjustment being the smallest increments. Optionally, the VDL may be coupled to an OCT implementation 252 that allows for a single detection path or receiver, which is generally described in U.S. patent application Ser. No. 12/018,706, incorporated by reference herein.

In one embodiment, the photoreceiver 250 comprise a detection element, such as an InGaAs photodiode and a transimpedance amplifier, which converts the electrical current signal generated by photons absorbed by the photodetector element into a voltage signal that can be read by the digitizer.

In one embodiment, a polarizing beam splitter divides horizontal and vertical polarization components returning from the sample and reference paths. Dual photoreceivers measure horizontal and vertical interference fringe intensities versus depth, $\Gamma_h(z)$ and $\Gamma_v(z)$, respectively. Alternatively, spectral interferometric techniques with polarization sensitivity may be implemented by recording four sequential single-channel measurements or simultaneous dual-channel horizontal and vertical polarization component measurements in conjunction with the well characterized reference path. Typically, some gain amplification is given at this stage or in a following stage, as well as some filtering for removing noise that is outside of the relevant electrical bandwidth. The gained and filtered voltage signal is digitized. The OCT interferogram [S(k)] is digitized at 16-bit resolution using a high-speed PCI digitizer board 270 (AlazarTech ATS660, Toronto, Canada) coupled to photoreceiver 250 and the primary OCT signal and auxiliary wavemeter 260 signal. The external clock derived from the wavemeter and regenerated by the arbitrary waveform generator (Gage CompuGen) allows acquisition of data directly in wavenumber (k) space. S(k) is converted using the Fast Fourier Transform (FFT) into the pathlength (z) domain. The magnitude of the transformed OCT A-scan [|S(z)|] represents the backscattered magnitude at depth z in the sample. The digitizer 270 is coupled to a computer processor, which is a state-of-the-art workstation with a fast multi-core processor, RAID striped disk array, and large RAM space.

In one embodiment, if the PS-OCT system 200 is coupled to catheter 242 then the sample path of the OCT system can propagate through a calibration system 248 including a plurality of retardation plates on the distal end of the sample path fiber to have its polarization state transformed, as shown in FIG. 2. The detected transformation will be different than the expected and actual transformation due to the ambiguity caused by the fiber optic. Polarization ambiguity in a fiber-based PS-OCT can change dramatically upon movement and bending of the fiber cable during catheterization procedures. Using the method described herein, the comparison of the detected transformation with the expected transformation of polarization in the system of retardation plates will provide calibration coefficients, such as the Jones matrix of the catheter fiber, to overcome the ambiguity and compensate or correct polarization data from back-scattering events happening distal to the calibration retardation plate system. An exemplary catheter for OCT systems is disclosed in common assigned provisional application Ser. No. 60/949,511, filed Jul. 12, 2007, herein incorporated by reference. The calibration system 248 includes a system of retardation plates with at least a first birefringent material and a second birefringent material. If a PS-OCT approach is used to calibrate, each retardation plate must have sufficient thickness and reflectivity to be visualized in an OCT image. In one embodiment, each retardation plate can be visualized concurrently with specimen imaging. The calibration retardation plate system can be imaged in the same A-scan if scan depth is sufficiently long, or with a separate interferometer (separate reference arm of different path length and separate readout) sharing only the sample path (catheter) fiber. Light must be focused/collimated and reflectivity chosen such that signal-to-noise ratio from surfaces of retardation plates is sufficiently high to avoid noise in calibration coefficients but not have detrimental self-interference patterns in the specimen imaging interferometer. One of the references would have to be looking at a non-focused image.

Calibration may be used to detect absolute axis orientations using single mode fiber base PS-OCT. Calibration requires that some signal be collected from a known element distal to the entire fiber. There are several different embodiments for a calibration system in the distal, post-fiber portion of a catheter probe. In one embodiment, separate retardation plates are placed between collimating/focusing elements and a rotating/deflecting prism. The collimating/focusing elements can be GRIN lenses.

In another embodiment, dual-layered birefringent material is used as the capsule material of the catheter. In another embodiment, the sample beam is split with a partially reflective prism, which allows the transmitted portion to propagate to the calibrating retardation plates. Such an embodiment could be used for Doppler OCT calibration. In another embodiment, the sample beam is split with a dichroic wavelength-dependent prism and a separate light source is used to calibrate the fiber independently of the imaging beam. Such an embodiment allows the calibrating signal to be completely independent of the imaging signal. The calibration will be for a different wavelength than the imaging signal wavelength and Polarization Mode Dispersion ("PMD") will be adjusted and considered accordingly. In another embodiment, a separate interferometer is coupled to the sample path with the retardation plates, in order to separately image the retardation plate system. The separate interferometer includes a separate reference arm of different optical path length and separate readout.

Birefringence and Retardation

Figure 6:
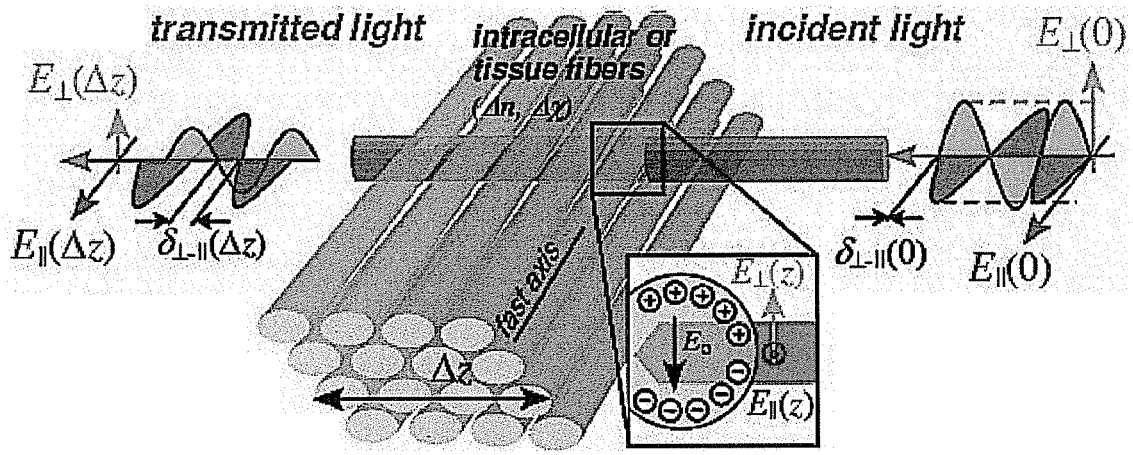
FIG. 6 is a schematic of the origin of form-birefringence ($\Delta n$) and form-biattenuance ($\Delta \chi$) in fibrous structures, where the electric field of incident light which is polarized perpendicular to the fiber axis ($E_\perp$) produces a surface charge density with an induced field ($E_o$), which changes the dielectric susceptibility and gives higher refractive index ($n_s$) relative to that experienced by light polarized parallel to the fiber axis ($E_\parallel$).

Form-birefringence is an optical property exhibited by media containing ordered arrays of anisotropic light scatterers which are smaller than the wavelength of incident light. Form-birefringence arises in biological structures when cylindrical fibers with diameters on this size scale are regularly oriented in a surrounding medium with different refractive index. The electric field of incident light oscillating perpendicular to the fibers ($E_\perp$) induces surface charges that create an induced field ($E_o$) within the fiber, as shown in FIG. 6. The induced field ($E_o$) anisotropically modifies forward scattered light so that phase and amplitude of $E_\perp$ is altered relative to the electric field component polarized parallel to the fibers ($E_\parallel$). The electric field of incident light which is polarized perpendicular to the fiber axis ($E_\perp$) produces a surface charge density with an induced field ($E_o$). This changes the dielectric susceptibility and gives higher refractive index ($n_s$) relative to that experienced by light polarized parallel to the fiber axis ($E_\parallel$). Form-biattenuance ($\Delta\chi$) causes anisotropic attenuation of amplitude between $E_\perp$ and $E_\parallel$. Many fibrillar tissue structures are optically anisotropic; however, values of $\Delta n$ vary considerably among species and tissue type.

The incremental phase retardation ($\delta_i$) incurred by the perpendicular component ($E_\perp$) results in slower light transmission and larger refractive index ($n_s$) than that experienced by light polarized parallel to the fiber axis ($E_\parallel$) with refractive index $n_f$. Incremental phase retardations ($\delta_i$) accumulate through fibrous structures and the composite retardation ($\delta$) between components polarized parallel ($E_\parallel$) and perpendicular ($E_\perp$) to the fibers after propagating a distance $\Delta z$ is:

$$\delta = \frac{360 \Delta n \Delta z}{\lambda_o} \qquad (15.1)$$

where $\delta$ is given in degrees. Similarly, the composite relative-attenuation ($\in$) between components polarized parallel ($E_\parallel$) and perpendicular ($E_\perp$) to the fibers after propagating a distance $\Delta z$ is:

$$\varepsilon = \frac{360 \cdot \Delta \chi}{\lambda_o} \cdot \Delta z \qquad (15.2)$$

where $\varepsilon$ is given in degrees.

Polarimetric Signal to Noise Ratio

Polarimetric speckle noise is one noise source impeding accurate determination of polarimetric properties of the sample under test. In contrast to intensity speckle noise, which is common to both polarization channels and only degrades I(z), polarimetric speckle noise is different for horizontal and vertical polarization channels and degrades depth resolved polarization data ("S(z)"). Intensity speckle noise is removed in part from polarization data by normalization of Stokes vectors.

First order statistics of the Stokes vector of scattered light for the case when horizontal and vertical fields are uncorrelated show that the probability density for the intensity is a sum of two orthogonal speckle fields (i.e. horizontal and vertical) and the Stokes parameters are Laplace variants. In some circumstances, speckle statistics of the Stokes vector for partially polarized light can be derived assuming Gaussian correlated field amplitudes. The statistics of polarimetric speckle noise likely depend on the tissue under investigation and possibly configuration of the sample path optics (e.g., numerical aperture of focusing lens, distal optics, and the like).

To quantitatively characterize the ability of the PS-OCT configuration to extract model P(z) from noisy S(z) a polarimetric signal-to-noise ratio ("PSNR") is introduced:

$$PSNR = \frac{l_{arc}}{\sigma_{speckle}} = \frac{2\delta \sin(\gamma)}{\sigma_{speckle}} \qquad (15.3)$$

where $l_{arc}$ is arc length of the noise-free model polarization arc [P(z)] associated with measured S(z). Standard deviation of polarimetric speckle noise (" $\sigma_{speckle}$ ") is a statistical measure of the point-by-point angular variation on the Poincaré sphere between detected S(z) and model P(z):

$$\sigma_{speckle} = \left( \frac{1}{J} \sum_j (\cos^{-1}(S(z) \cdot P(z)))^2 \right)^{1/2} \qquad (16)$$

where J is the total number of depth-resolved sample points within the specimen. By averaging an ensemble of $N_A$ uncorrelated speckle fields, $\sigma_{speckle}$ is reduced and PSNR is increased.

Exemplary Algorithm to Determine Retardation and Birefringence

The analysis for determining retardation from S(z) recorded by the PS-OCT configurations is for a region of sample depths with homogeneous polarimetric properties. If the sample is heterogeneous in depth, then retardation by the PS-OCT configurations for each range of depths where the sample polarimetric properties are homogenous is completed. In one embodiment, determining retardation from S(z) recorded with the PS-OCT configurations comprises estimating the three model parameters which mathematically specify the noise-free model polarization arc [P(z)]: (1) angle of arc rotation, which is equal to the double-pass retardation (2δ); (2) rotation axis (A) and (3) the arc's initial point, which represents the polarization at the specimen's front surface [P(0)]. A nonlinear fitting algorithm that takes S(z) as input and estimates model parameters has been developed. Implementation of the nonlinear fitting algorithm to estimate 2δ, A, and P(0) comprises formulation of a residual function ($R_o$) which specifies goodness of fit between S(z) and P(z):

$$R_o = \sum_j |S(z) - P(z; 2\delta, A, P(0))|^2 \qquad (17)$$

$R_o$ measures cumulative squared deviation between noisy S(z) and noise-free P(z). Model parameters are estimated by minimizing $R_o$ using a Levenberg-Marquardt algorithm and represent the best estimate of P(z).

Because PSNR increases with separation-angle ($\gamma$, Eq. (15.3)), the polarization at the specimen's front surface [P(0)] which gives $\gamma=90°$ provides the optimal incident polarization state for most accurate determination of δ. Because birefringence of preceding layers (e.g. single-mode optical fiber, anterior segment of the eye) is generally unknown, one is unable to select a priori a P(0) that provides a maximum separation-angle $\gamma=90°$. To resolve the problem of preceding unknown birefringent layers and estimate 2δ and A accurately, a multi-state nonlinear algorithm that uses M incident polarization states uniformly distributed on a great circle of the Poincaré sphere is employed. Utilizing multiple incident polarization states gives M distinct separation-angles ($\gamma_m$) distributed within the interval [0°, 90°] insuring that $\gamma_m=90°$ for some states. By using a multi-state approach, variance in estimated 2δ due to either uncertainty in A or low PSNR is minimized.

Implementation of the multi-state nonlinear algorithm to determine δ requires formulation of a multi-state residual function. A multi-state residual function ($R_M$) that is the algebraic sum of $R_o$ (Eq. (17)) over the M incident polarization states is:

$$R_M = \sum_{m=1}^{M} R_o(S_m(z); \delta, A, P_m(0)) \qquad (18)$$

$R_M$ gives the composite squared deviation between M sets of depth-resolved polarization data [$S_m(z)$] and corresponding M noise-free model polarization arcs [$P_m(z)$]. Model parameters [2δ, A, and $P_m(0)$] are estimated by minimizing $R_M$ using a Levenberg-Marquardt algorithm and represent the best estimates of $P_m(z)$ arcs.

The ability of the multi-state nonlinear algorithm to determine model parameters is verified on simulated noisy depth-resolved polarization data. The multi-state approach comprises all M noise-free model polarization arcs [$P_m(z)$] that rotate around the same rotation axis A by the same angle (2δ) regardless of $P_m(0), l_{arc,m}$, or $\gamma_m$. The uncertainty in any single $P_m(z)$ arc is offset through constraints placed upon the other M−1 arcs by the multi-state residual function. In addition, the multi-state nonlinear algorithm comprises a single estimate of unknown parameters using all depth-resolved data points in the scan, allowing the consideration of more than two points at a time [S(0) and S(Δz)] and the incorporation of S(z) arc curvature.

Birefringence in tissue is predominantly the form type and results from an anisotropic distribution of refractive index from ordered fibrillar structures. For high sensitivity quantification of birefringence with the PS-OCT configurations, a nonlinear fitting of normalized Stokes vectors from multiple incident polarization states provides accurate determination of retardation in thin, weakly birefringent tissue specimens such as a turbid birefringent film. Disordering of fibrillar tissue structure in response to a pathological condition will likely modify the birefringence; therefore, the highly sensitive PS-OCT configuration detects changes in birefringence, monitors the pathological conditions which alter fibrillar tissue structure, fibrillar structures corresponding to pathological conditions such as fibrous caps (fibrillar structures can correspond to pathological conditions such as fibrous caps), and diagnoses other clinical conditions.

Neurotubule fibrils in unmyelinated axons contribute to Retinal Nerve Fiber Layer ("RNFL") form birefringence. Highly sensitive determination of tissue retardation provides a measure of the number of fibrils ($N_t$), and birefringence may provide a measure of fibril density ($\rho_t$) within the volume sampled by the PS-OCT sample beam. The PS-OCT configuration can quantify the number of RNFL neurotubules during the progression of glaucoma, localize collagen denaturation in the skin of burn victims, and aid in the diagnosis of other pathologies or traumas that affect the fibrous structure of form birefringent tissue.

When polarized light propagates through the birefringent RNFL, the eigenpolarization state oriented perpendicular to the neurotubules travels slower and phase is delayed relative to the parallel eigenpolarization component, resulting in a transformation in polarization state. Each fibril (e.g. microtubule, collagen filament, actin-myosin complex) acts as a nanoretarder on incident polarized light and introduces a phase delay between eigen polarizations. Incremental phase delay $\delta_{inc}=0.0046°$ is introduced by individual neurotubules at $\lambda_o=546$ nm.

Light that propagates to the specimen's rear surface acquires an accumulated retardation from the nanoretarder fibrils:

$$\delta = \frac{360\Delta n \Delta z}{\lambda_o} = \frac{360 f \Delta n_t \Delta z}{\lambda_o} \quad (19)$$

where f is the local volume fraction of fibrils in the sampled specimen volume, $\lambda_o$ is the free-space wavelength of incident light, and Ant is the specific birefringence of the fibril (sometimes referred to as the birefringence-per-volume fraction), $\Delta z$ is the thickness from the front surface to the rear surface. The local volume fraction (f) of fibrils within the sampled specimen volume (V) may be written as:

$$f = \frac{N_t v_o}{V} \quad (20)$$

where $N_t$ is the number of fibrils in V and $v_o$ is the volume occupied by a single fibril within V. The sampled specimen volume V, may be approximated by a cylinder of light defined by the beam waist radius ($w_o$) and specimen thickness ($\Delta z$):

$$V = \pi w_o^2 \Delta z \quad (21)$$

where $A_o$ is the cross-sectional area of one fibril. For a given $w_o$, the determination of specimen thickness and retardation provides a measure of the number ($N_t$) and density ($\rho_t$) of fibrils in the sampled specimen volume:

$$N_t = \frac{\pi \lambda_o w_o}{1440 \Delta n_t A_o} \delta, \quad (22)$$

$$\rho_t = \frac{\pi \lambda_o}{1440 \Delta n_t A_o w_o} \left(\frac{\delta}{\Delta z}\right) = \frac{\pi}{4 \Delta n_t A_o w_o} \Delta n. \quad (23)$$

The number of fibrils in the sampled specimen volume scales with $\delta$. The density of fibrils scales with $\Delta n$.

The values of the scaling parameters in Eqs. (23) for neurotubules in the RNFL by assuming a beam waist radius ($w_o=10$ mm) and a free-space wavelength ($\lambda_o=0.83$ μm) and by using known values for the neurotubule-specific birefringence ($\Delta n_t=0.025$) and cross-sectional area [$A_o=\pi$ (12 nm)$^2=450$ nm$^2$]. $\Delta\delta_{RNFL}$ is used to estimate the number of neurotubules in the nasal ($N_t\approx17\times10^3$) and inferior (Nt≈133× $10^3$) regions. Similarly, $\Delta n_{RNFL}$ shows the neurotubule density is considerably lower in the nasal region ($\rho_t\approx1.1$ μm$^{-3}$) than in the inferior region ($\rho_t\approx2.5$ μm$^{-3}$).

Form Biattenuance

In the eigenpolarization coordinate frame, the polarization-transforming properties of a non-depolarizing, homogeneous optical medium such as anisotropic fibrous tissue are described by the Jones matrix $$J = \begin{bmatrix} \exp((\Delta\chi + i\Delta n)\pi\Delta z/\lambda_0) & 0 \\ 0 & \exp((-\Delta\chi - i\Delta n)\pi\Delta z/\lambda_0) \end{bmatrix} \quad (24)$$

$$= \begin{bmatrix} |\xi_1|\exp(i\arg(\xi_1)) & 0 \\ 0 & |\xi_2|\exp(i\arg(\xi_2)) \end{bmatrix}$$

where $\xi_1$ and $\xi_2$ are the complex eigenvalues representing changes in amplitude and phase for orthogonal eigenpolarization states with free-space wavelength $\lambda_0$ propagating a distance $\Delta z$ through the medium. Attenuation common to both eigenpolarizations does not affect the light polarization state and is neglected here.

The phase retardation ($\delta$, expressed in radians) between eigenpolarization states after propagation through the medium is the difference between the arguments of the eigenvalues, $\delta=\arg(\xi_1)-\arg(\xi_2)$, which allows simplification of the Jones matrix to $$J = \begin{bmatrix} |\xi_1|\exp(i\delta/2) & 0 \\ 0 & |\xi_2|\exp(i\delta/2)) \end{bmatrix}. \quad (25)$$

The polarimetric parameter diattenuation (D) is given quantitatively by:

$$D = \frac{|T_1 - T_2|}{T_1 + T_2} = \frac{||\xi_1|^2 - |\xi_2|^2|}{|\xi_1|^2 + |\xi_2|^2} \quad 0 \leq D \leq 1, \quad (26)$$

where $T_1$ and $T_2$ are the intensity transmittances for the two orthogonal eigenpolarizations and the attenuation can be a consequence of either anisotropic absorption or anisotropic scattering of light out of the detected field.

Birefringence ($\Delta n$) is the phenomenon responsible for phase retardation ($\delta$) of light propagating a distance $\Delta z$ in an anisotropic element and is given by:

$$\Delta n = \frac{\lambda_0}{2\pi} \frac{\delta}{\Delta z} = n_s - n_f, \quad (27)$$

where $n_s$ and $n_f$ are the real-valued refractive indices experienced by the slow and fast eigenpolarizations, respectively. Form-birefringence ($\Delta n$) is proportional to and given experimentally by the phase retardation-per-unit-depth ($\delta/\Delta z$).

Dichroism describes the phenomenon of diattenuation in an anisotropically absorbing element (such as that exhibited by a sheet polarizer), and the term is also used to describe differential transmission or reflection between spectral components (such as that exhibited by a dichroic beam splitter), leading to confusion if taken in the incorrect context. Neither dichroism nor diattenuation nor polarization dependent loss ("PDL") can be expressed on a per-unit-depth basis and are thus unsuitable quantities for depth-resolved polarimetry in scattering media. Attenuance has come to describe the loss of transmittance by either absorption or scattering; biattenuance is the differential loss of transmittance between two eigenpolarization states by either absorption (dichroism) or scattering. Form-biattenuance is an experimentally and theoretically relevant term that can be expressed on a per-unit-depth basis. Numerically, biattenuance ("$\Delta\chi$") is given by Equation (28):

$$\Delta\chi = \chi_s - \chi_f, \quad (28)$$

where $\chi_s$ and $\chi_f$ are attenuation coefficients of the slow and fast eigenpolarizations. For absorbing (dichroic) media, $\chi_s$ and $\chi_f$ are simply imaginary-valued refractive indices.

The phase retardation ($\delta$) and thickness ($\Delta z$) of an element are linearly related by its birefringence ($\Delta n$). However, the relationship between an element's diattenuation [D, Eq. (26)] and thickness ($\Delta z$) is nonlinear. This nonlinear relationship complicates expression of an element's form-biattenuance: one cannot generally and without approximation refer to a diattenuation-per-unit-depth as one can refer to form-birefringence as a phase retardation-per-unit-depth. For example, if optical element A has thickness $\Delta_{zA}$=1 mm, diattenuation $D_A$=0.4, and phase retardation AA=7/4 radians and element B is made of the same material but has twice the thickness AZB=2 mm, element B will have twice the phase retardation 5B=28A=n/2 radians but will not have twice the diattenuation DB=0.69:2DA.

For depth-resolved polarimetry in scattering media (i.e. PS-OCT), expression of an element's form-biattenuance on a per-unit-depth basis is desirable theoretically and experimentally. The relative attenuation ($\delta$) experienced by light propagating to a depth $\Delta z$ in an anisotropic element is defined as:

$$\varepsilon = \frac{2\pi}{\lambda_0} \Delta z \Delta \chi, \quad (29)$$

and form-biattenuance ($\Delta\chi$) can now be meaningfully expressed on a relative attenuation-per-unit-depth basis ($\delta/\Delta z$). Relative-attenuation ($\delta$) is the complimentary term to phase retardation [6, Eq. (27)], just as biattenuance ($\Delta\chi$) is the complementary term to birefringence ($\Delta n$).

The Jones matrix of the anisotropic medium from Eqs. (24) and (25) becomes $$J = \begin{bmatrix} \exp\left(\frac{\varepsilon + i\delta}{2}\right) & 0 \\ 0 & \exp\left(-\frac{\varepsilon - i\delta}{2}\right) \end{bmatrix}, \quad (30)$$

and the "anisotropic damping" effect of the relative-attenuation ($\delta$) becomes apparent. Diattenuation (D) is related to relative-attenuation ($\delta$) by:

$$D = \frac{|e^\varepsilon - e^{-\varepsilon}|}{e^\varepsilon + e^{-\varepsilon}} = \tanh(\varepsilon). \quad (31)$$

For small relative-attenuation, a small-angle approximation is valid and $D \in$.

Dual attenuation coefficients ($\mu ax$ and $\mu ay$) to represent Beer's law attenuation for each eigenpolarization can be related to diattenuation (D) using Eq. (31) where relative-attenuation ($\delta$) is related to dual attenuation coefficients by $\in = |\mu ax - \mu ay| \Delta z/2$. Phase retardation ($\delta$) is in the argument of an exponential [Eq. (30)] and therefore has units of radians, but is also commonly expressed in units of degrees ($180 \cdot \delta/\pi$), fractions of waves ($\delta/2\pi$), or length ($\lambda_o \cdot \delta/2\pi$). Similarly, relative attenuation ($\in$) is in the argument of an exponential [Eq. (30)] and has units of radians. The expression of relative-attenuation in units of radians (or degrees, fractions of waves, or length) is less intuitive than for phase retardation.

Exemplary Signal Conditioning

In one embodiment, detected photocurrents representing horizontal and vertical polarimetric fringe signals ($\Gamma_h(z)$ and $\Gamma_v(z)$) are pre-amplified, bandpass filtered, and digitized. Coherent demodulation of $\Gamma_h(z)$ and $\Gamma_v(z)$ yields signals proportional to the horizontal and vertical electric field amplitudes [$E_h(z)$ and $E_v(z)$] and relative phase [$\Delta\phi(z)$] of light backscattered from the specimen at each depth z within the A-scan. An ensemble ($N_A$) of A-scans representing uncorrelated or weakly correlated speckle fields are acquired on a grid within a small square region (50 µm×50 µm) at each location of interest on the specimen. Acquisition of an ensemble of $N_A$ A-scans at each location is repeated for M incident polarization states distributed in uniform increments on a great circle on the Poincaré sphere by M phase shifts ($\delta_{LCVR,m}$) of a polarization control element (e.g., Liquid Crystal Variable Retarder, LCVR). For each M, the calibrated LCVR phase shift ($\delta_{LCVR,m}$) is subtracted from the demodulated relative phase [$\Delta\phi_m(z)$] to compensate for the light's return propagation through the LCVR. This yields M sets of horizontal and vertical electric field amplitudes [$E_{h,m}(z)$ and $E_{v,m}(z)$] and compensated relative phase [$\Delta\phi_{c,m}(z)$]. Non-normalized Stokes vectors are calculated from $E_{h,m}(z)$, $E_{v,m}(z)$, and $\Delta\phi_{c,m}(z)$ for each of $N_A$ A-scans in the ensemble and for each M. Ensemble averaging over $N_A$ at each depth z (denoted by $\langle\rangle_{N_A}$) reduces $\sigma_{speckle}$ by a factor of approximately $N_A^{1/2}$ and then normalization yields M sets of depth-resolved polarization data [$S_m(z)$] for each location, $$S_m(z) = \begin{pmatrix} Q(z) \\ U(z) \\ V(z) \end{pmatrix} = \quad (32)$$

-continued $$\begin{pmatrix} \langle E_{h,m}(z)^2 - E_{v,m}(z)^2 \rangle_{N_A} \\ \langle 2E_{h,m}(z)E_{v,m}(z)\cos[\Delta\phi_{c,m}(z)] \rangle_{N_A} \\ \langle 2E_{h,m}(z)E_{v,m}(z)\sin[\Delta\phi_{c,m}(z)] \rangle_{N_A} \end{pmatrix} \Big/ \langle E_{h,m}(z)^2 + E_{v,m}(z)^2 \rangle_{N_A}$$

When Stokes vectors are first normalized and then ensemble-averaged over $N_A$, the resulting Stokes vectors $[W_m(z)]$ have magnitude $[0 \leq |W_m(z)|=W_m(z) \leq 1]$ which is directly related to the extent of the distribution of pre-averaged normalized Stokes vectors on the Poincaré sphere within the ensemble at each depth z, $$W_m(z) = \left( \begin{matrix} E_{h,m}(z)^2 - E_{v,m}(z)^2 \\ 2E_{h,m}(z)E_{v,m}(z)\cos[\Delta\phi_{c,m}(z)] \\ 2E_{h,m}(z)E_{v,m}(z)\sin[\Delta\phi_{c,m}(z)] \end{matrix} \right) \Big/ \overline{E_{h,m}(z)^2 + E_{v,m}(z)^2} \Big|_{N_A}. \quad (33)$$

$W_m(z)$ is used as a scalar weighting factor in the multistate nonlinear algorithm to estimate phase retardation ($\delta$) and relative-attenuation ($\in$).

Exemplary Multistate Nonlinear Algorithm to Determine Form-Biattenuance

In one embodiment, high sensitivity quantification of form-biattenuance ($\Delta\chi$) is accomplished using a nonlinear fitting algorithm based on the approach for determining form-birefringence ($\Delta n$) with the PS-OCT configurations. A modified multistate residual function ($R_M$) may be implemented which gives the composite squared deviation between M sets of depth-resolved polarization data $[S_m(z)]$ and corresponding M noise-free model polarization arcs $[P_m(z)]$ weighted by $W_m(z)$, $$R_M = \sum_{m=1}^{M} R_o[S_m(z_j), W_m(z_j); 2\varepsilon, 2\delta, \hat{\beta}, P_m(0)] \quad (34)$$

where $R_o$ is the weighted single-state residual function, $$R_o = \sum_{j=1}^{J} \{W_m(z_j)[S_m(z_j) - P[z_j; 2\varepsilon, 2\delta, \hat{\beta}_m, P(0)]]\}^2, \quad (35)$$

and the subscript "j" is used to denote the discrete nature of sampled data versus depth (z). Model parameters $[2\in, 2\delta, \hat{\beta},$ and $P_m(0)]$ are estimated by minimizing $R_M$ using a Levenberg-Marquardt algorithm and represent the best estimate of $P_m(z)$. At increased penetration depths (lower electrical signal-to-noise ratio) or large initial separation-angles $[\gamma_m(0)]$, $W_m(z)$ decreases and $S_m(z)$ are given less weight. $\Delta\chi$ and $\Delta n$ are calculated using Eqs. (27) and (29) from estimates of $\in$ and $\delta$ provided by the multistate nonlinear algorithm. $\Delta z$ is measured by subtracting the front and rear specimen boundaries in the OCT intensity image and dividing by the bulk refractive index (n=1.4).

Uncertainty in estimates of any single $P_m(z)$ arc is offset through constraints placed upon the other M−1 arcs by the modified residual function [Eq. (34)]. All M noise-free model polarization arcs $[P_m(z)]$ must collapse toward the same eigen-axis ($\hat{\beta}$) at the same rate (2$\in$) and must rotate around $\hat{\beta}$ by the same angle (2$\delta$) regardless of the incident polarization state. Discrimination between arc movements on the Poincaré sphere due to either $\Delta n$ or $\Delta\chi$ is accomplished by restricting contributions from each into orthogonal planes.

Model for Form-Biattenuance and Form-Birefringence

Figure 7:
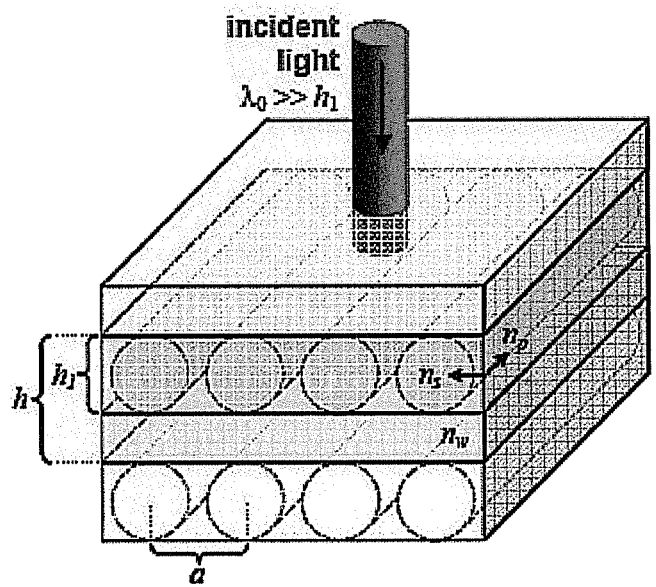
FIG. 7 is a schematic model for form-biattenuance consisting of alternating anisotropic and isotropic layers.

The phenomenon of form-biattenuance and a model predicting the relative contribution of $\Delta n$ and $\Delta\chi$ to transformations in polarization state of light propagating in anisotropic media is shown in FIG. 7. The model may be used as examples of tissues with alternating anisotropic media and isotropic layers. Other models are possible that would generally be considered to explain polarimetric properties of tissues.

Optical Axis Orientation

Optic axis orientation ($\theta$) provides the direction of constituent fibers relative to a fixed reference direction (i.e., horizontal in the laboratory frame). A method for measuring depth-resolved optic axis orientation [$\theta(z)$] deep within multiple layered tissues uses the PS-OCT, as described previously.

Figure 8:
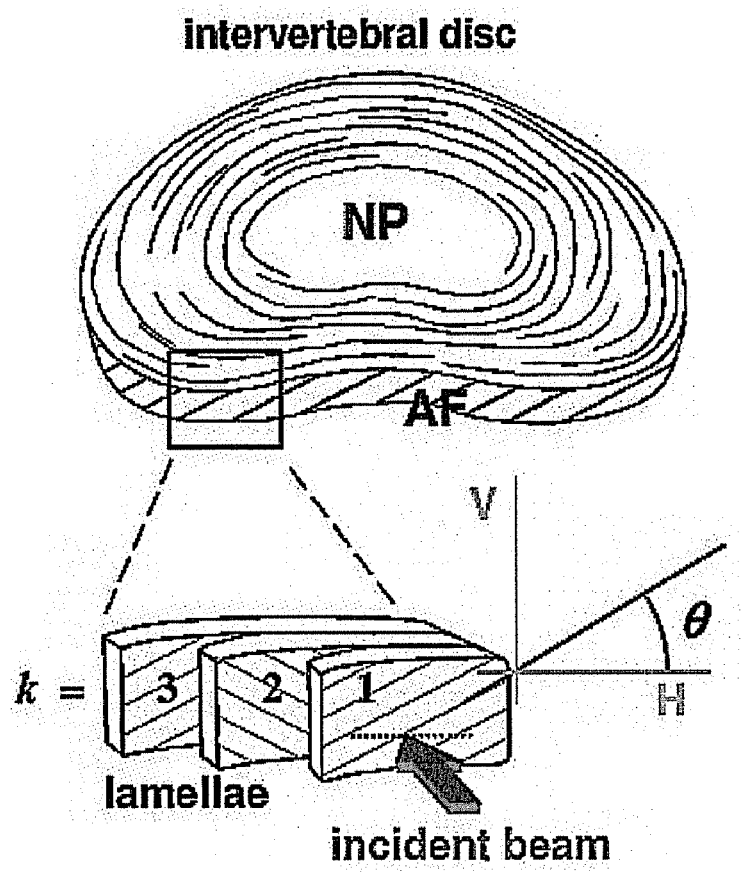
FIG. 8 is a schematic of intervertebral disc and annulus fibrosis showing alternating fiber directions in the laboratory frame (H and V), the incident beam, and scan location (dashed red line).

Collagen organization in cartilage and intervertebral disc cartilage may be used as a model tissue on which to demonstrate the depth-resolved polarimetric imaging ability of PS-OCT. As shown in FIG. 8, intervertebral discs are located between spinal vertebrae and consist of the annulus fibrous ("AF"), enclosing an inner gel-like nucleus pulposis ("NP"). Annulus fibrous is composed of axially concentric rings (i.e. lamellae) of dense type I collagen fibers (fibrocartilage), the orientation of which is consistent within a single lamella but approximately perpendicular to fibers in neighboring lamellae, forming a lattice-like pattern. Regular orientation of collagen fibers within a single lamella is responsible for form-birefringence [$\Delta n(z)$], and alternating fiber directions between successive lamellae correspond to alternation of optic axis orientation [$\theta(z)$] within the annulus fibrous.

Multiple layered fibrous tissue such as the annulus fibrous is modeled as a stack of K linearly anisotropic, homogeneous elements, each with arbitrary phase retardation ($\delta_k$), relative-attenuation ($\in_k$), optic axis orientation ($\theta_k$), and corresponding kth Jones matrix $[J_{s(k)}(\delta_k, \in_k, \theta_k)]$. Incident polarized light ($E_{in}$) propagating to the rear of the kth intermediate element and back out in double-pass ($E_{dp\_out(k)}$) is represented by:

$$E_{dp\_out(k)} = J_{s(1)}^T J_{s(2)}^T \ldots J_{s(k-1)}^T J_{s(k)}^T J_{s(k)} J_{s(k-1)} \ldots J_{s(2)} J_{s(1)} E_{in}. \quad (41)$$

For the most superficial layer (k=1), Eq. (41) becomes $E_{dp\_out(1)} = J_{s(1)}^T J_{s(1)} E_{in}$, and $J_{s(1)}(\delta_1, \in_1, \theta_1)$ can be recovered using matrix algebra. Likewise, $\delta_1$, $\in_1$, and $\theta_1$ can be found using a nonlinear fit to the trajectory between $S_{in}$ and $S_{dp\_out(1)}$ on the Poincaré sphere and Eq. (42):

$$\theta = \text{sgn}(\beta_u)\cos^{-1}(\hat{\beta}\cdot\hat{q})/2, \quad (42)$$

where $\hat{q}$ is the unit-vector defining the Q axis of the three-dimensional Cartesian coordinate system containing the Poincaré sphere and $\beta_u$ is the U component of $\hat{\beta}$.

For the next layer (k=2), Eq. (41) becomes $E_{dp\_out(2)} = J_{s(1)}^T J_{s(2)}^T J_{s(2)} J_{s(1)} E_{in}$. Matrix algebra and knowledge of $J_{s(1)}$ allows recovery of $J_{s(2)}(\delta_2, \in_2, \theta_2)$. Likewise, $\delta_2$, $\in_2$, and $\theta_2$ can be found using a nonlinear fit to the trajectory between $S_{dp\_out(1)}$ and $S_{dp\_out(2)}$ after compensation of anisotropy in the superficial layer (reverse rotation by $-\delta_1$ and reverse collapse by $-\in_1$ with respect to $\hat{\beta}_1$). This process is repeated for successively deeper layers in the stack to determine $\delta_k$, $\in_k$, and $\theta_k$ for all k layers.

In PS-OCT imaging, the polarization state detected after double-pass to the rear of the kth intermediate element $[E_{dp\_out(k)},$ Eq. (41)] is also transformed by optics in the instrument (e.g., beamsplitter, optical fiber, polarization modulator, retroreflector), adding complexity to the optic axis orientation analysis. With inclusion of a Jones matrix ($J_c$) which encompasses instrumental transformations, Eq. (41) becomes:

$$E_{dp\_out(k)} = J_c^T J_{s(1)}^T \ldots J_{s(k-1)}^T J_{s(k)}^T J_{s(k)} J_{s(k-1)} \ldots J_{s(1)} J_c E_{in}. \quad (43)$$

For a single-mode-fiber-based PS-OCT configuration, $J_c$ represents unstable phase retardation between arbitrary elliptical eigenvectors. In this case, eigenvectors of Jones matrices in Eq. (43) vary in an unknown fashion and measurement of the anatomical fiber direction with respect to the laboratory frame is distorted by the optical fiber birefringence. The calibration system 248 may allow fiber-based PS-OCT configurations to overcome distortion in the optical fiber. The PS-OCT instrument has stable $J_c$ with linear eigenvectors in the laboratory frame; therefore $J_c$ reduces to simple phase retardation ($\delta_c$, due to the beamsplitter and retroreflector) between horizontal and vertical interference fringes. In one embodiment, the PS-OCT configuration incorporates a liquid crystal variable retarder ("LCVR") to modulate the launched polarization state incident on the specimen by applying a voltage-controlled phase retardation ($\delta_{LCVR}$). The optic axis of the LCVR is horizontal, thus the total systematic phase retardation ($\delta_{LCVR}+\delta_c$) can be compensated by subtraction of $\delta_{LCVR}+\delta_c$ from the relative phase of the detected horizontal and vertical interference fringe signals, allowing unambiguous and undistorted measurement of the anatomical fiber direction ($\theta_k$) absolutely referenced to the laboratory frame.

Depth-Resolved Identification

Transformations in the depth-resolved polarization state of light backscattered from linearly anisotropic media such as fibrous tissue can be represented as depth-resolved normalized Stokes vector (S(z)) arcs on the Poincaré sphere. The trajectory of S(z) arcs in the presence of $\Delta n$ and $\Delta \chi$ is governed by a vector differential equation, as by a vector differential equation. Briefly, S(z) arcs rotate in a circular trajectory around an eigenaxis ($\hat{\beta}$) by an angle equal to the double-pass phase retardation ($2\delta$) of the specimen. Phase retardation ($\delta$, radians) is related to tissue birefringence ($\Delta n$), wavelength ($\lambda_0$) and specimen thickness ($\Delta z$) by $\delta = 2\pi \Delta n \Delta z / \lambda_0$. S(z) arcs also collapse towards $\hat{\beta}$ by an angle related to the double-pass relative attenuation ($\in$, radians), which is proportional to tissue biattenuance ($\Delta \chi$), wavelength and specimen thickness by $\in = 2\pi \Delta \chi \Delta z / \lambda_0$. The combined effect, a spiraling collapse of S(z) towards $\hat{\beta}$, occurs for tissues exhibiting both $\Delta n$ and $\Delta \chi$.

Eigenaxis ($\hat{\beta}$) is directly related to the fiber orientation ($\theta$) given with respect to the horizontal by $\theta = \mathrm{sgn}(\hat{\beta}_u \cos^{-1}(\hat{\beta} \cdot \hat{q})/2)$, where $\hat{q}$ is the unit vector defining the Q-axis of the three-dimensional Cartesian coordinate system containing the Poincaré sphere and $\hat{\beta}_u$ is the U component of $\hat{\beta}$. When $\theta$ is constant and biattenuance is negligible ($\Delta \chi \ll \Delta n$), the curvature ($\kappa(z)$) of the S(z) arc is nearly constant and is approximated by:

$$\kappa(z) \approx \frac{1}{\cos^{-1}[S(z) \cdot \hat{\beta}]} \quad (44)$$

where depth-resolved separation-angle $\gamma(z) = \cos_{-1}[S(z) \cdot \hat{\beta}]$. The unit tangent vector $[\hat{T}(z)]$ of S(z) is given by:

$$\hat{T} = \frac{dS(z)}{dl_{\mathrm{arc}}}, \quad (45)$$

where $l_{arc}$ is the arc length of S(z) on the Poincaré sphere. However, abrupt changes in fiber orientation [$\theta(z)$] versus specimen depth (e.g. in annulus fibrous) produce corresponding changes in both $\hat{\beta}$ and in the trajectory of S(z). Discontinuities in the unit tangent vector [$\hat{T}(z)$] give rise to instances of infinite or very large curvature [$\kappa(z)$] for continuous z. For numeric calculation using discrete sampled data ($z_j = 0, 1, 2, \ldots$) the unit tangent vector is:

$$\hat{T}(z_j) = \frac{S(z_j) - S(z_{j-1})}{|S(z_j) - S(z_{j-1})|} \quad (46)$$

and curvature is:

$$\kappa(z_j) = \left| \frac{\hat{T}(z_j) - \hat{T}(z_{j-1})}{|S(z_j) - S(z_{j-1})|} \right|. \quad (47)$$

Figure 9A:
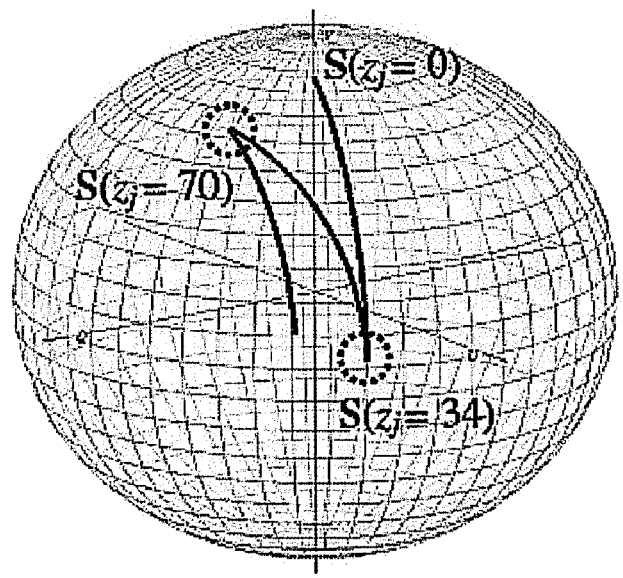
FIG. 9A is a Poincaré sphere showing the simulated trajectory of S($z_j$) for k=3 layers with fiber orientations θ=−10°, 95°, and −5°.
Figure 9B:
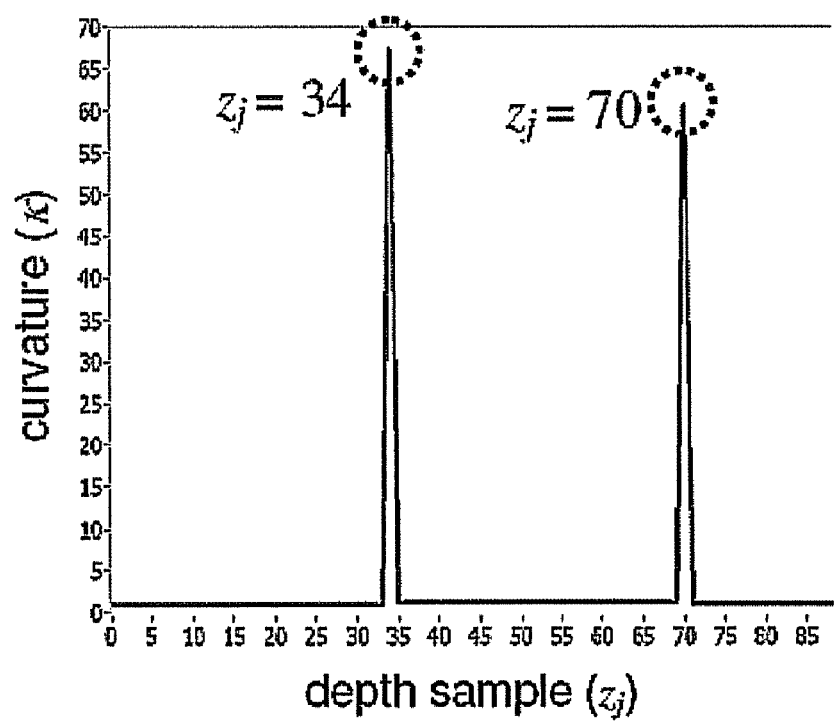
FIG. 9B is a graph of the abrupt changes in trajectory of S($z_j$) corresponding to layer interfaces at $z_j$=34 and $z_j$=70 are observed as spikes in the curvature [κ(z)] indicated by dashed circles.

FIG. 9A shows simulated depth-resolved polarization data [$S(z_j)$] and FIG. 9B shows calculated curvature [$\kappa(z_j)$] for a three-layer birefringent specimen with constant $\Delta n$ and three fiber orientations $\theta = -10°, 95°,$ and $-5°$.

Exemplary Uses of Depth-Resolved Birefringence, Depth-Resolved Biattenuance, Depth-Resolved Retardation, and Depth-Resolved Optical Axis Aneurism vulnerability may be assessed with the PS-OCT configurations described above. The likelihood of an aneurism rupturing is related to the mechanical properties of collagen in the arterial walls. If collagen fibers are oriented regularly with the artery longitude, then there is reduced mechanical strength in the perpendicular (circumferential) direction. If aneurisms that contain a more random orientation of fibers (and thus distribute strength in both longitudinal and circumferential directions) are less likely to rupture, then the PS-OCT configurations may assess the risk or vulnerability of aneurysms' to rupture. In one embodiment, fiber-based PS-OCT configuration is capable of estimating absolute collagen orientation when a known polarization reference is fixed to the distal scanning end. This could be accomplished by using a capsule made out of a known birefringent material as the reference, which is indicated above with a birefringent material in the capsule material of the catheter.

For Alzheimer's disease ("AD"), the detection of neurofibrilary tangles and amyloid plaques using the PS-OCT configuration may be applied for diagnostic purposes. Cerebral amyloid pathologies exhibit linear birefringence and dichroism, which may be detected by the PS-OCT configurations. In amyloid angiopathy, deposition of collagen fibrils in the walls of capillaries and veins results in narrowed lumina and even occlusion has been observed in patients with AD. Collagen XVIII accumulates in all types of cerebral blood vessels including arteries, arterioles, capillaries, venules, and veins in patients with AD. Collagen XVIII is associated with amyloid deposition in blood vessel walls and may be involved in the pathogenesis of AD. The mechanisms leading to the reduced blood flow may be found in the retina and are related to those that produce the cerebral blood flow abnormalities in AD. Narrowing of the retinal venous diameter may be related to an increased venous wall thickness due to collagen deposition, as found in cerebral veins. The PS-OCT configurations may assess such characteristics in the characterization of AD.

Also, RNFL thickness measurements using the PS-OCT configurations are useful in identifying the early changes associated with glaucomatous optic neuropathy ("GON"). Inferior RNFL loss corresponding to superior visual field loss is a typical pattern found in early GON. The predominant inferior visual field loss seen in patients with GON and AD would correspond structurally to superior RNFL losses. A specific pattern of superior RNFL loss could be detected by using the PS-OCT configurations in patients with early AD.

In surgical grafting during reconstructive surgery, the PS-OCT configurations may be applied to aid alignment of collagen fiber axes. Coronary artery bypass grafting ("CABG") is the most commonly performed major surgery and a critical determinant of its outcome has been postulated to be injury to the conduit vessel incurred during the harvesting procedure or any pathology preexistent in the harvested vessel. Intravascular PS-OCT imaging from the radial arteries ("RA") and/or saphenous veins may reliably detect atherosclerotic lesions in the RAs and discerns plaque morphology as fibrous, fibrocalcific, or fibroatheromatous. The PS-OCT configurations can also be used to identify patent or healthy regions in longitudinal sections of radial arteries or saphenous veins for grafting The PS-OCT configurations may be used for margin detection in bronchial tumors. The PS-OCT configurations may also perform early diagnosis of tumors and cancerous tissue. The PS-OCT configuration images may identify bronchial tumor presence as destructive growth by ignoring and effacing normal tissue boundaries. Featureless PS-OCT configuration images or regions with reduced form-birefringence may lack the ordered multilayered appearance of the healthy airway wall. The PS-OCT configurations may also differentiate between areas of chronic inflammation and invasive malignancy; where the clear demarcations of epithelium and lamina propria may be observed at inflamed sites and may be lost in presence of invasive neoplasia. The PS-OCT configurations may individually define the epithelium, subepithelial components, and cartilage. The PS-OCT configurations may identify morphologic changes associated with inflammatory infiltrates, squamous metaplasia, and tumor presence.

The PS-OCT configurations may assess the coronary plaque collagen content. Arterial plaques include intimal collagen, which degrades and leads to plaque destabilization. Collagens are major structural components of the arterial wall extracellular matrix, comprising 20%-50% of the dry weight, with the predominant types being Type I and III, where type IV is in the basement membrane. The tensile strength of plaque is determined by fibrillar collagen (type I) and extracellular lipid. Inflammation leads to release of collagenases and collagen breakdown increasing the risk of plaque rupture. Collagen birefringence is a function of highly organized alignment and also the nature of the chemical groups of the collagen encountered and layer thickness. Form-birefringence is almost exclusively a function of the fibrous nature of the structure and two refractive indices of the fiber and surrounding material. The intimal region over the necrotic core exhibits high polarization sensitivity with organized collagen. The PS-OCT configurations may assess plaque collagen content. For example, the fibrous cap is a layer of fibrous connective tissue is thicker and less cellular than the normal intima. The fibrous cap contains macrophages and smooth muscle cells. The fibrous cap of an atheroma is composed of smooth muscle cells, macrophages, foam cells, lymphocytes, collagen and elastin). The PS-OCT configurations may assess plaque collagen content and generate high resolution structural assessments to identify the thin caps associate with high risk plaques.

EXAMPLES

The following examples are put forth so as to provide those of ordinary skill in the art with a complete disclosure and description of how the articles, devices, systems, and/or methods claimed herein are made and evaluated, and are intended to be purely exemplary and are not intended to limit the scope of articles, systems, and/or methods. Efforts have been made to ensure accuracy with respect to numbers (e.g., amounts, temperature, etc.), but some errors and deviations should be accounted for.

Example 1

Phase Retardation and Fast-Axis Angle of a Birefringent Sample

A mica retarder (Meadowlark Optics) is positioned in the common-path spectral interferometer 10, as shown in FIG. 1, orthogonal to the direction of incident light propagation and used as a birefringent sample.

Figure 3A:
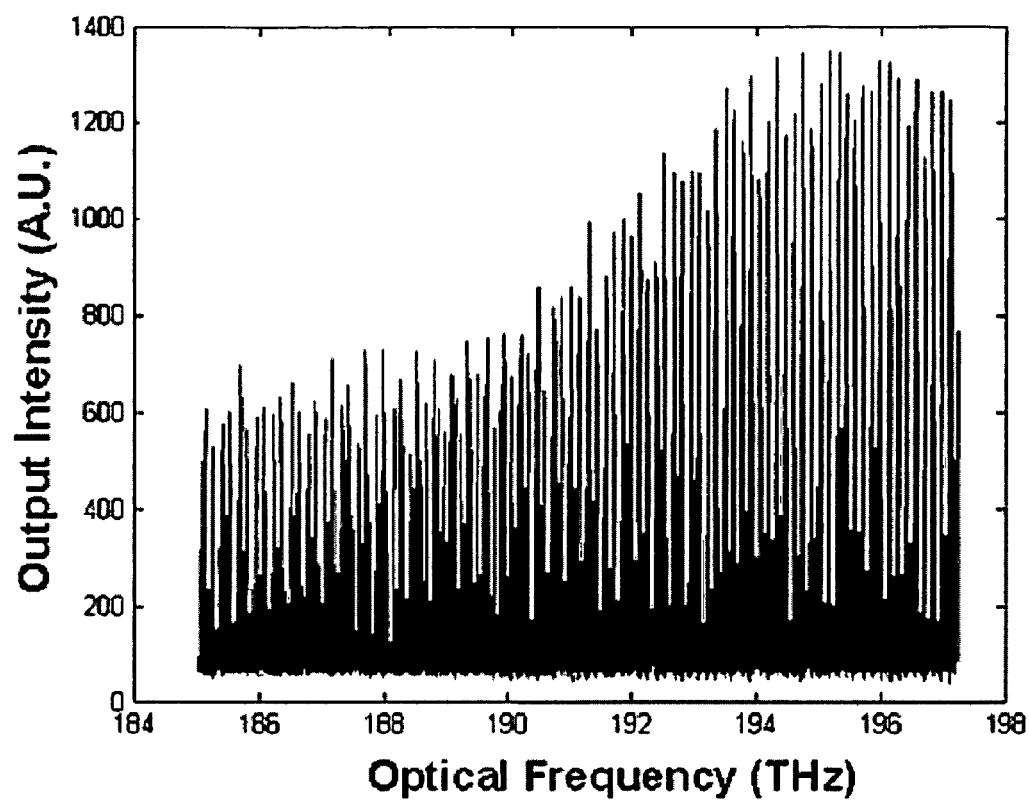
FIG. 3A depicts the typical spectral output intensity from the fiber based single channel polarization-sensitive spectral interferometer with the whole spectrum of 12.2 THz.
Figure 3B:
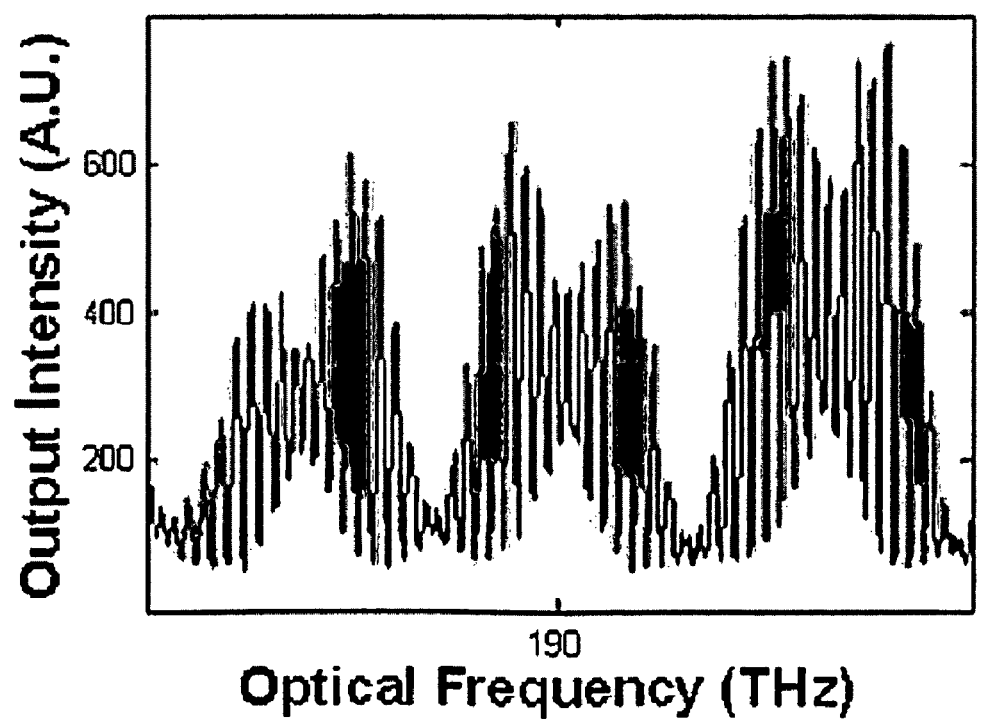
FIG. 3B depicts an enlarged small segment of 10 GHz between 190.69 THz and 190.79 THz of the whole spectrum (12.2 THz) from FIG. 2A to view fringes in more detail.

FIG. 3A depicts the typical spectral output intensity of a mica retarder positioned in the common path fiber based single channel polarization-sensitive spectral interferometer orthogonal to the direction of incident light propagation and used as a birefringent sample. The output spectral width of the whole spectrum was 12.2 THz, as shown in FIG. 3A. FIG. 3B depicts a small segment of 10 Ghz between 190.69 and 190.79 THz of the whole spectrum (12.2 THz) to view fringes in more detail. The output spectrum in FIGS. 3A and 3B is modulated with several distinct high frequencies, and a swept source and OSA with high resolution are required to avoid undersampling. A conventional OSA with a spectral resolution of $\Delta\lambda=0.1$ nm provides a scan range of about 12 mm and is unable to sample sufficiently a spectral modulation of such high frequency.

Figure 4A:
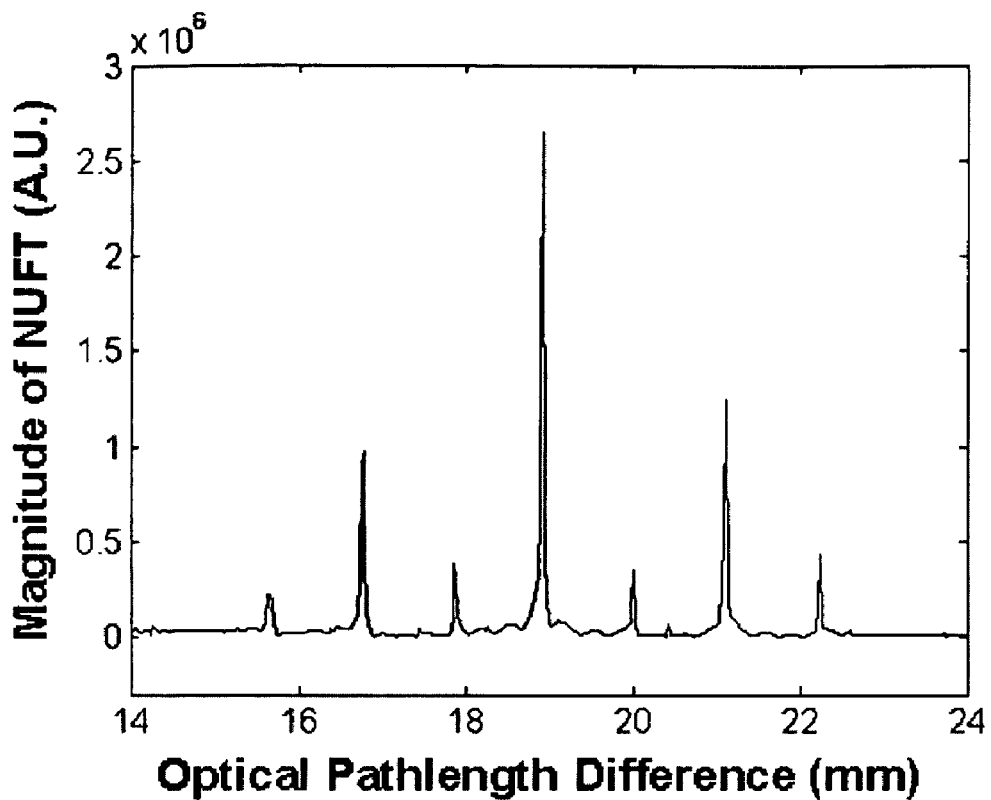
FIG. 4A depicts the Fourier Transform magnitude of interference fringes between and from the back surfaces of the glass window.
Figure 4B:
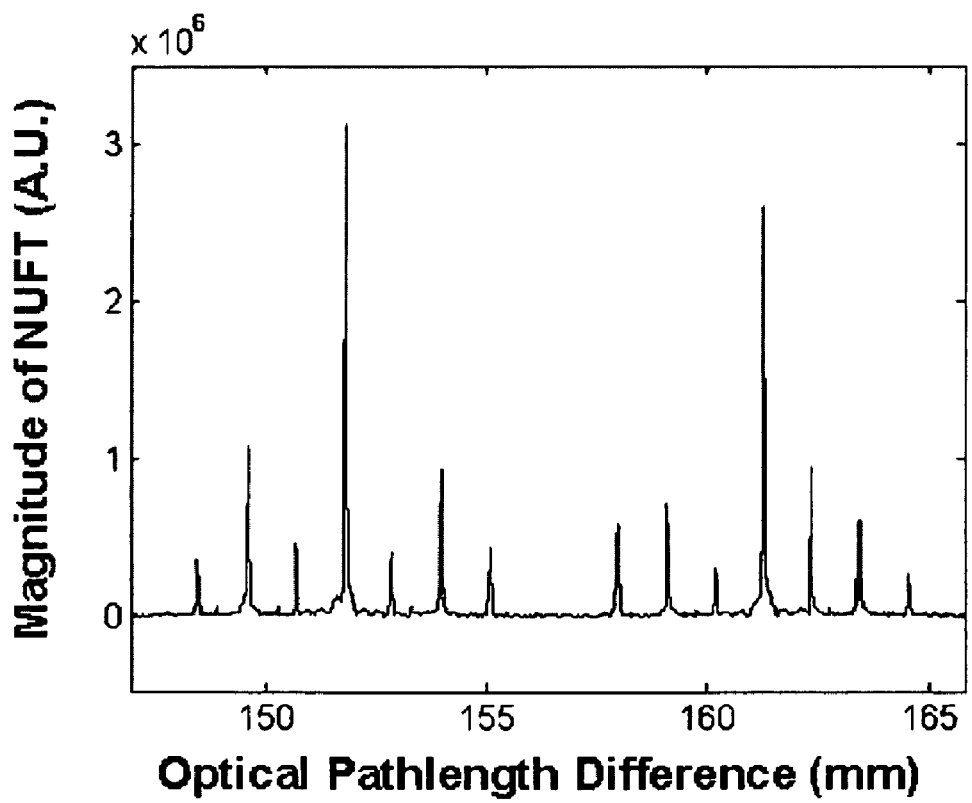
FIG. 4B depicts the Fourier Transform magnitude of interference fringes between the back surface of the glass window and the birefringent sample.

FIGS. 4A and 4B shows the Fourier transform magnitude of interference fringes between the front and back surfaces of the glass window, as shown in FIG. 4A, and between the back surface of the glass window and the birefringent sample, as shown in FIG. 4B. Although the ISA provides the corresponding optical frequency for each recorded spectral component of output intensity, successive spectral samples of output intensity are not equally spaced in optical frequency. In such cases of non-uniform frequency sampling, a Nonuniform Fourier Transform ("NUFT") algorithm was used rather than a simple fast Fourier transform, which assumes uniform sampling. As shown in FIG. 4A, four Stokes spectral components of interfering light are separated into seven peaks in the optical path-length difference domain. The position of the fourth peak and spacing between peaks are determined by the optical path length difference between interfering beams generated in the common-path spectral domain interferometer and phase retardations due to the two PM fiber segments in the FOSPI, respectively. In FIG. 4A, the first seven peaks are formed from interference between the back surface of the glass window and the front surface of the birefringent sample and are similar to those from interference between the front and the back surfaces of the glass window in FIG. 4A, indicating the polarization state between the window and the sample is unchanged. Alternatively, the rightmost seven peaks in FIG. 4B resulting from interference between the back surface of the birefringent sample show the polarization-state change of double-pass light propagation through the birefringent sample.

Figure 5A:
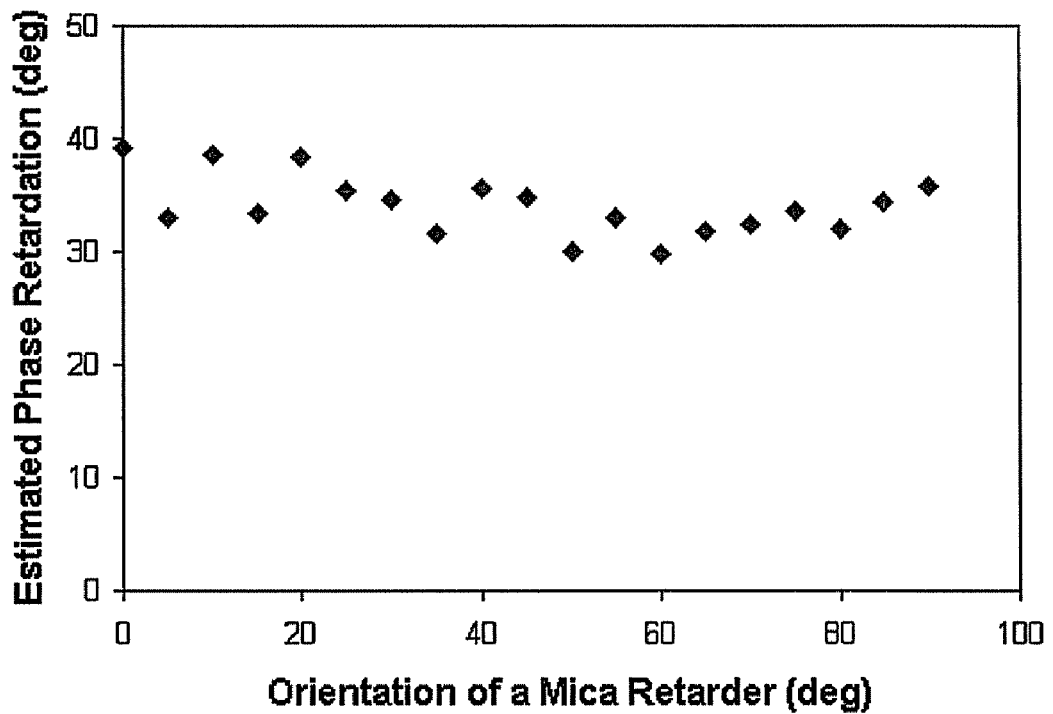
FIG. 5A depicts Phase retardation due to birefringence of the birefringent sample estimated from interference between the back surface of the glass window and the back surface of the birefringent sample.
Figure 5B:
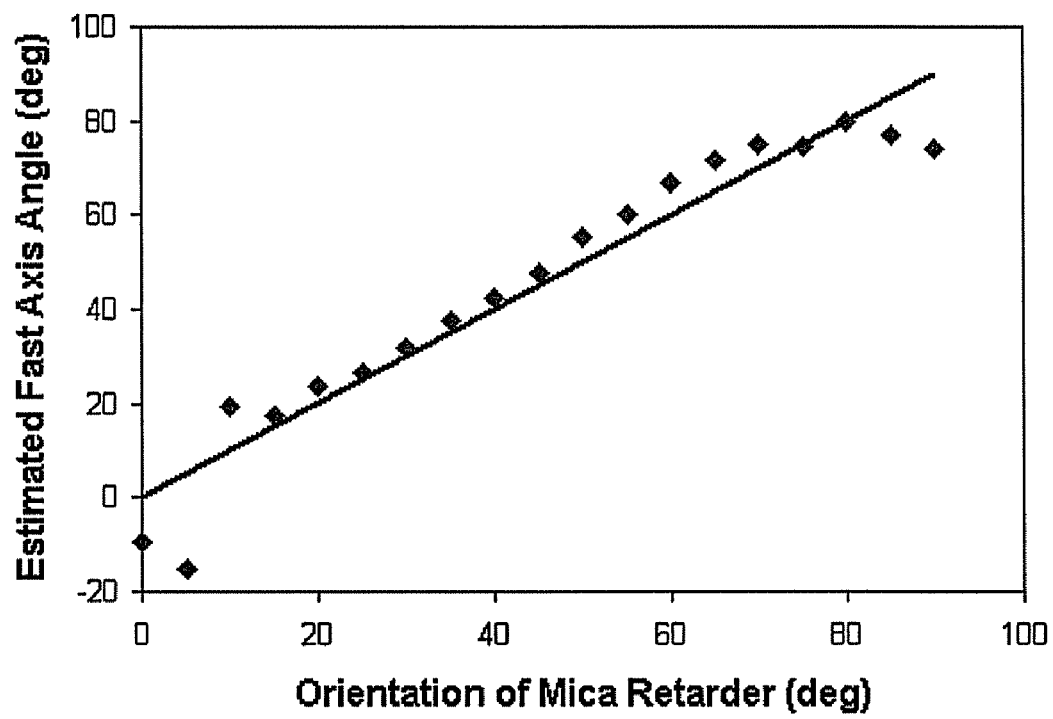
FIG. 5B depicts Phase Retardation due to fast-axis angle of the birefringent sample estimated from interference between the back surface of the glass window and the back surface of the birefringent sample.

Phase retardation due to birefringence, as shown in FIG. 5A, and fast-axis angle, as shown in FIG. 5B, of the birefringent sample were estimated from interference between the back surface of the glass window and the back surface of the birefringent sample by using equations (13) and (14). For this measurement, the birefringent sample was rotated in 5 degrees increments from 0 degrees to 90 degrees. An estimated single-pass phase retardation of δ=34.06 degrees+/−2.68 degrees is consistent with a valued deduced from the manufacturer's specification (31.4 degrees). The estimated fast-axis angle was offset by 87.5 degrees to the reference with respect to the laboratory coordinate system.

Incorporation of a FOSPI 50 into a common-path spectral interferometer 30 with a broadband frequency-swept laser source allows measurement of the polarization and depth information with a single optical frequency scan. Spectral modulations introduced by the common-path spectral interferometer and by the FOSPI combine sequentially so that the polarization and depth information are encoded into separate channels in the time-delay domain. For the single optical frequency scan, multiple scans are required to average out polarimetric speckle noise, as described above. Multiple scans may be implemented to average out polarimetric speckle noise—as described above. Output from the fiber based single channel polarization sensitive spectral interferometer is a convolution of the FOSPI output and that from the common path spectral interferometer.

The full set of Stokes parameters of interfering light at a specific optical path-length difference consists of seven channels in the time-delay domain, and channel separation is dependent on two factors: spectral resolution ($\Delta v$) of the instrument and choice of PM fiber lengths in the FOSPI. For one embodiment, a general bulk optical element does not require PM fibers as mentioned above. For another embodiment of the fiber-based single-channel polarization-sensitive spectral interferometer, channel separation is $\Delta\tau=3.7$ ps and is set by lengths of the PM fiber segments. Maximum channel separation in the time delay domain is inversely related ($\Delta\tau_{max}=1/8\Delta v$) to the spectral resolution of the instrument, and the broadband frequency-swept laser source ($\Delta v=50$ MHz) used here allows $\Delta\tau_{max}=2.5$ ns. Such large channel separations in the time delay domain require optically stable kilometer-length PM fiber segments in the FOSPI. The sample used here is optically transparent, and its optical thickness is large enough so that the two sets of seven channels due to refraction from the front and back surfaces are sufficiently separated. In general, the bandwidth of each peak in the time delay domain is determined by the optical thickness of the sample, and wide channel separation in the time delay domain is required to isolate each channel.

Prior knowledge of the incident polarization state is not required to determine phase retardation and fast-axis angle of a birefringent sample in the fiber based single channel polarization sensitive spectral interferometer. An assumption of no polarization transformation between the reference and sample surfaces is necessary in the analysis, which is easily achieved in a common path spectral interferometer.

Difference in Stokes parameters determined from the reference and interference fringe signals are optical path-length difference [$\Delta(v)$] and the phase retardation [$\delta(v)$] of a birefringent sample. If a sample is non birefringent, Stokes parameters of an interfering fringe signal are $S_i^{(i)}=\cos\Delta(v)S_i^{(1)}(v)$ with Stokes parameters of light reflected from the reference surface $S_i^{(1)}(v)$ and an optical pathlength difference $\Delta(v)$. Integration of a common-path spectral interferometer with a FOSPI at the output enables measurement of the Stokes parameters of the interference signal with neither a calibration correction factor nor any assumption of polarization state of reflected light from the reference surface.

As shown in FIGS. 5A and 5B, phase retardation and fast-axis angle of a birefringent sample are difficult to measure when the direction of an incident light oscillation is primarily parallel to the fast axis of the sample retarder. In this case, the polarization state of light entering the interferometer should be modified. Such modification can be implemented by the input polarization state preparation optics 20 inserted between the reference and the sample surfaces, the segment can be considered a known portion of the birefringent sample with a specified polarization transformation, and the analysis presented may be modified to determine the birefringence and fast axis of a sample. Such an analysis is presented in the paper by Kemp, N J et. al. Opt. Express 2005: 13:4507, herein incorporated by reference.

Exemplary Conclusion

The FOSPI 50 is a PM fiber based instrument to measure the polarization state of collected light and incorporation of the FOSPI 50 into a common-path spectral interferometer 30 allows measurement of the full set of Stokes parameters of interfering light with a single optical frequency scan where multiple A-scans are required to average polarimetric speckle noise unless multiple A-scans are required to average polarimetric speckle noise as indicated above. The high spectral resolution of the broadband frequency swept laser source enables encoding and decoding both the polarization and depth information into separate channels in the time delay domain.

Performance of the fiber based single channel polarization sensitive spectral interferometer has been demonstrated by measuring phase retardation δ and fast axis angle α of a mica retarder while rotated in 5° increments from 0° to 90°. A single optical frequency scan is sufficient to estimate both phase retardation and fast axis angle of a mica plate without knowledge of the polarization state of incident light. The fiber based single channel polarization sensitive spectral interferometer presented allows measurement of both phase retardation and fast axis angle of a birefringent sample. Performance of the fiber based single channel polarization sensitive spectral interferometer is sensitive to phase retardations due to two PM fiber segments in a FOSPI (($\phi_1(v)$ and ($\phi_2(v)$ in Equation 4). The PS-OCT configurations may minimize variations in phase retardations induced by environmental, mechanical and thermal fluctuations.

The coupling of a thermally isolated mechanical enclosure to the polarization sensitive spectral interferometer improves the stability of PM fiber phase retardations ($\phi_1(v)$ and $\phi_2(v)$). Also, by selecting optimal optics for the frequency range of the broadband laser source the signal-to-noise ratio of the system is improved. By using the end facet of the sample path illuminating fiber instead of the glass window, un-wanted and deleterious backscattered signal can be avoided. Slow scan speed of 1 Hz of the current system can be a limitation in some applications especially that require time-resolved measurements. Also, the experimental results, i.e., estimated phase retardation and fast axis angle of a birefringent sample, may be sensitive to post signal processing especially when the instrument is not optimized. Fourier transformation followed by processing in the optical pathlength domain and simple arithmetic are used in the present analysis to determine phase retardation and fast axis angle. Alternatively, a model-based approach may provide estimates of position of reflecting surfaces and birefringence properties. The proposed methodology may be applied to measure in real time the depth resolved polarization state of back-reflected light from a variety of samples.

Example 2

High-Sensitivity Determination of Birefringence in Turbid Media

Polarimetric Speckle Noise Reduction

Figure 10A:
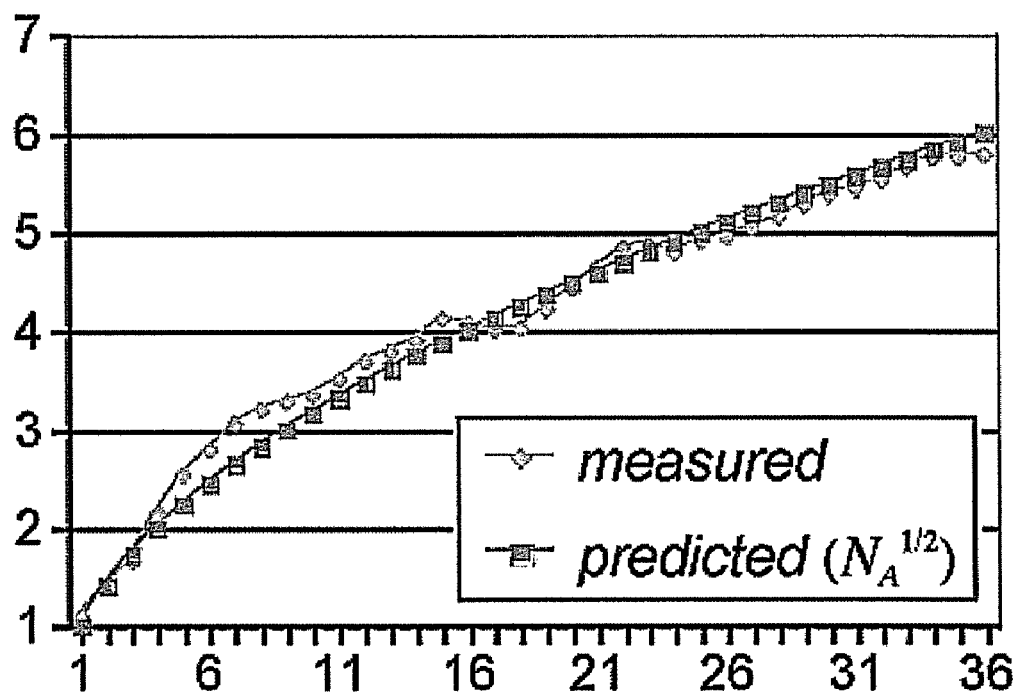
FIG. 10A is a graph of the ensemble averaging $N_A$ uncorrelated speckle fields increases PSNR by a factor of $N_{A1/2}$.
Figure 10B:
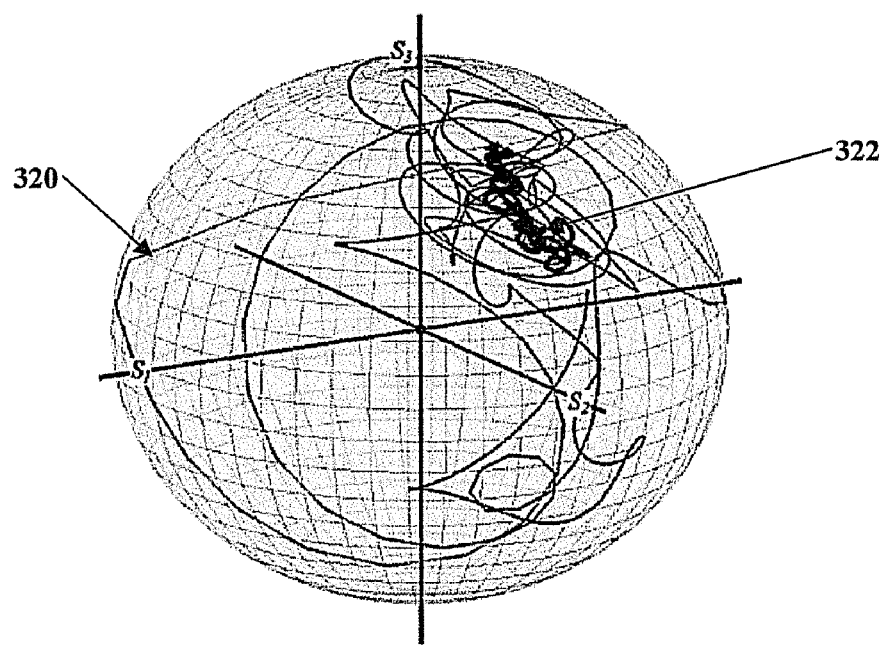
FIG. 10B is a Poincaré sphere before (thin line) and after (thick line) averaging $N_A$=36 speckle fields for birefringent film $S_m$(z) for m=1 plotted on the Poincaré sphere. Averaged S(z) begins to resemble the noise-free model polarization arc P(z).

Many signal processing applications employ ensemble averaging of N separate trials for reducing additive white noise in recorded signals by a factor of $N^{1/2}$. As shown in FIGS. 10A and 10B, averaging $N_A$ uncorrelated speckle fields reduces polarimetric speckle noise ($\sigma_{speckle}$) and increases PSNR by a factor of $N_A^{1/2}$. Sixfold increase in PSNR is demonstrated after averaging Stokes vectors for $N_A$=36 speckle fields in a birefringent film. FIG. 10B is a Poincaré sphere before (thin line 320) and after (thick line 322) averaging $N_A$=36 speckle fields for birefringent film $S_m(z)$ for m=1 plotted on the Poincaré sphere, where averaged S(z) begins to resemble the noise-free model polarization arc P(z).

Birefringent Film Measurement

To verify operation of the PS-OCT configuration and the multi-state nonlinear algorithm, horizontal and vertical interference fringe intensities ($\Gamma_h(z)$ and $\Gamma_v(z)$) were recorded from a turbid birefringent film (New Focus, #5842) with thickness $\Delta z$=80 µm. A transparent mica waveplate was placed on top of the birefringent film to test the multi-state nonlinear algorithm in the presence of a preceding birefringent element with unitary transformation. PSNR was increased by averaging Stokes vectors from Equation (48)

$$\vec{S}(z_j) = \begin{pmatrix} I(z_j) \\ Q(z_j) \\ U(z_j) \\ V(z_j) \end{pmatrix} = \begin{pmatrix} E_h(z_j)^2 + E_v(z_j)^2 \\ E_h(z_j)^2 - E_v(z_j)^2 \\ 2E_h(z_j)E_v(z_j)\cos[\phi_{diff}(z_j)] \\ 2E_h(z_j)E_v(z_j)\sin[\phi_{diff}(z_j)] \end{pmatrix}. \quad (48)$$

from $N_A$=36 uncorrelated speckle fields within a small two-dimensional square grid region (50×50 µm²). Depth-resolved polarization data [$S_m(z)$] was plotted on the Poincaré sphere for M=6 incident polarization states. To demonstrate invariance of the multi-state nonlinear algorithm to a preceding birefringent element, δ of the birefringent film is determined for a range of mica waveplate slow-axis orientations ranging from 0° to 180° in increments of 10°.

Retardation (δ) of the birefringent film was determined for a range of mica waveplate slow-axis orientations ranging from 0° to 180° in increments of 10°. Mean and standard deviation of δ over the range of mica waveplate orientations was δ=24.50°±0.47°, while maximum deviation from the mean was 0.91°. Mean birefringence was $\Delta n=7.0 \cdot 10_{-4}$ or 30.6°/100 µm.

In Vivo Primate Retinal Nerve Fiber Layer Measurement

The PS-OCT configuration is described in previously and the multi-state nonlinear algorithm to detect RNFL birefringence and biattenuance, respectively. $\Gamma_h(z_j)$ and $\Gamma_v(z_j)$ were recorded from the RNFL. All experimental primate procedures were approved by the University of Texas at Austin Institutional Animal Care and Use Committee (protocol #02032203) and conform to all USDA, NIH, and ARVO guidelines for animal welfare.[151] Both eyes of two healthy 6 kg, 4 year old, female rhesus monkeys were imaged. Monkeys were anesthetized with a combination of ketamine (10 mg/Kg) and xylazine (0.25 mg/Kg) given intramuscularly. Anesthesia depth was monitored and maintained by a certified veterinary technologist. Pupils were dilated using one drop of 1% cyclopentolate and one drop of 1% tropicamide. The head was gently secured to a goniometer in the prone position using a custom mask. One drop of 10% methylcellulose was placed in the eye to be imaged and a contact lens was placed on the eye. The contact lenses were chosen to render the monkeys slightly myopic so incoming light was focused at the inner limiting membrane. Specifications of the contact lens were: base curve=6.9 mm, diameter=8.6 mm, power=+2 diopter. The retina was viewed using a surgical microscope and the eye was rotated and held in position by a Thornton fixation ring. A coaxial visible aiming beam was placed directly onto the optic nervehead for registration at the start of each scan. Sample arm optics were configured for pupil-centric scanning. Prior to recording high resolution maps, a low-resolution fast scan was performed to insure the selected lateral area included all desired peripapillary features.

The data acquisition time to record a single peripapillary map may vary according to the optical configuration; however, the time to record the data may not be that important inasmuch as longer acquisition times are desired. Laser power incident on the cornea was 2.8 mW during lateral scanning and 1.7 mW while stationary. Approximate laser spot size at the retinal surface was 30 µm. Axial resolution was determined by the 5 µm coherence length of the laser source in air. Lateral scanning in the x and y dimensions allowed acquisition of $\Gamma_h(z_j)$ and $\Gamma_v(z_j)$ at two user-specified locations: 1 mm inferior to the center of the ONH and 1 mm nasal to the center of the ONH. At each location, $\Gamma_h(z_j)$ and $\Gamma_v(z_j)$ were recorded for an ensemble of $N_A$=36 uncorrelated speckle fields in a small two-dimensional square grid region (50 µm×50 µm). Registration of the imaging location between sessions was accomplished by positioning the eye with the center of the ONH at the zeroed position of the visible aiming beam.

The anterior surface of the RNFL ($z_j$=0) was determined automatically by thresholding, and the posterior RNFL surface was identified manually from the depth-resolved interference fringe intensity [I($z_j$)]. The difference between posterior and anterior surfaces (optical RNFL thickness) was divided by the mean group tissue refractive index (n=1.38) to determine RNFL thickness ($\Delta z_{RNFL}$). Stokes vectors within the ensemble were digitally averaged, normalized, and plotted on the Poincaré sphere for M=6 incident polarization states. The multistate nonlinear algorithm was applied to extract P($z_j$) from S($z_j$) and determine in vivo primate RNFL retardation ($\delta_{RNFL}$) and birefringence ($\Delta n_{RNFL}$).

Figure 11A:
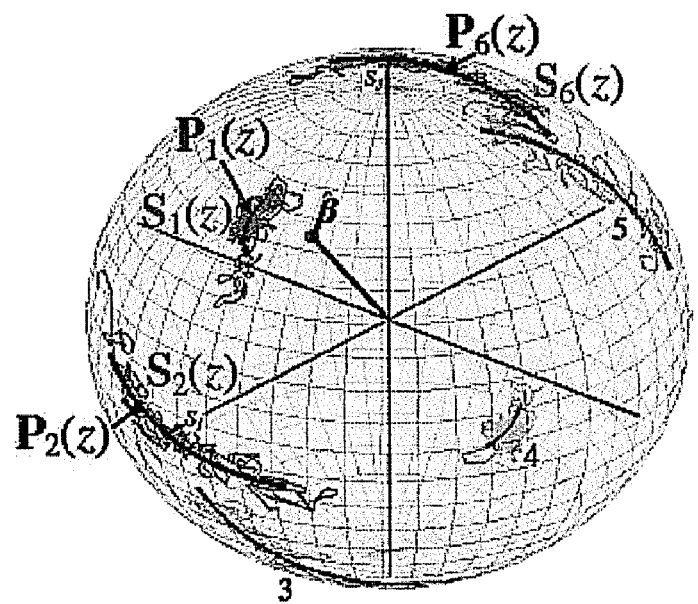
FIG. 11A is a Poincaré sphere showing depth-resolved polarization data [$S_m$(z), gray] for M=6 incident polarization states in a thick (Δz=170 μm) RNFL 1 mm inferior to the ONH.
Figure 11B:
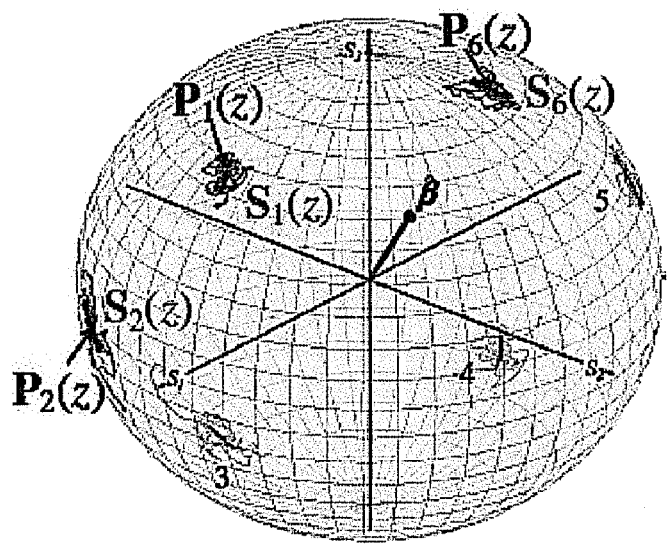
FIG. 11B is a Poincaré sphere showing thin (Δz=50 μm) RNFL 1 mm nasal to the ONH. Noise-free model polarization arcs [$P_m$(z), black] and rotation axis (A) were extracted by the multi-state nonlinear algorithm. (Note: m=3, 4, and 5 are on the far side of the Poincaré sphere).

The primate RNFL was imaged in a thick region (1 mm inferior to the center of the ONH) and a thin region (1 mm nasal to the center of the ONH) during two sessions two weeks apart. Table 1 summarizes the detected RNFL $\Delta z_{RNFL}$, $\delta_{RNFL}$, and $\Delta n_{RNFL}$ given in units of degrees per 100 micrometers. FIGS. 11A and 11B shows PS-OCT-recorded $S_m(z_j)$ for M=6 incident polarization states and corresponding $P_m(z_j)$ extracted by the multistate nonlinear algorithm. Noise-free model polarization arcs [$P_m(z)$, black] and rotation axis (A) were extracted by the multi-state nonlinear algorithm. Arcs corresponding to M=3, 4, and 5 are on the far side of the Poincaré sphere in FIGS. 11A and 11B.

TABLE 1

Thickness and Birefringence of in Vivo Primate RNFL

| Location (session) | $\Delta z_{RNFL}$ (mm) | $\delta_{RNFL}$ (°) | $\Delta n_{RNFL}$ (°/100 µm) |
|---|---|---|---|
| Inferior (day 1) | 170 | 29.5 | 17.3 |
| Inferior (day 2) | 167 | 27.8 | 16.6 |
| Nasal (day 1) | 50 | 3.4 | 6.8 |
| Nasal (day 2) | 51 | 3.9 | 7.6 |

Ensemble averaging to increase PSNR comes with a loss in lateral resolution, increase in acquisition time by a factor of $N_A$, and diminishing returns associated with the $N_A^{1/2}$ relationship. Loss in lateral resolution is from the increase in the field size corresponding to lateral extent of uncorrelated speckle fields included in the averaged ensemble. Because speckle noise statistics are closely related to the beam diameter, detection optics, and microstructure of scatterings in the specimen, each instrument-specimen combination has an optimum spacing between speckle fields which minimizes loss in lateral resolution but insures speckle fields are uncorrelated.

The $N_A^{1/2}$ behavior of averaged polarimetric speckle noise allows trial-and-error discovery of the optimum spacing between speckle fields without a priori knowledge of the scatterer microstructure. The optimum spacing between speckle fields for imaging the birefringent film with our system was determined empirically (8 µm). Larger spacing results in reduced lateral resolution and smaller spacing leaves speckle fields partially correlated thereby diminishing the $N_{A\,1/2}$ noise reduction achieved through ensemble averaging. The likelihood of combining polarization data from adjacent anatomical features is decreased with marginal additional instrumentation complexity by averaging over a small two-dimensional square grid region rather than a pattern of traditional rastered B-scan.

The choice of M=6 incident polarization states in these results was selected empirically. Because switching time of the LCVR is negligible compared to total acquisition time, acquiring M incident polarization states increases imaging time by a factor of M. Although selection of an incident polarization state with γ=90° may be achieved using analysis of prior polarization arcs, this would require additional computing resources (e.g. automatic segmentation, real-time nonlinear fitting) and improvements in speed and accuracy may be marginal. Increased acquisition time by a factor of $N_A \times M$, although problematic during in vivo imaging with slow time-domain systems is not a limiting factor for instruments incorporating spectral-domain approaches.

Results of the birefringent film experiments indicate the multi-state nonlinear algorithm may be applied to determine retardation in turbid birefringent media. Moreover, determination of δ by the multi-state nonlinear algorithm is invariant to unknown unitary polarization transformations from preceding birefringent layers as demonstrated by the mica waveplate rotation.

Figure 12:
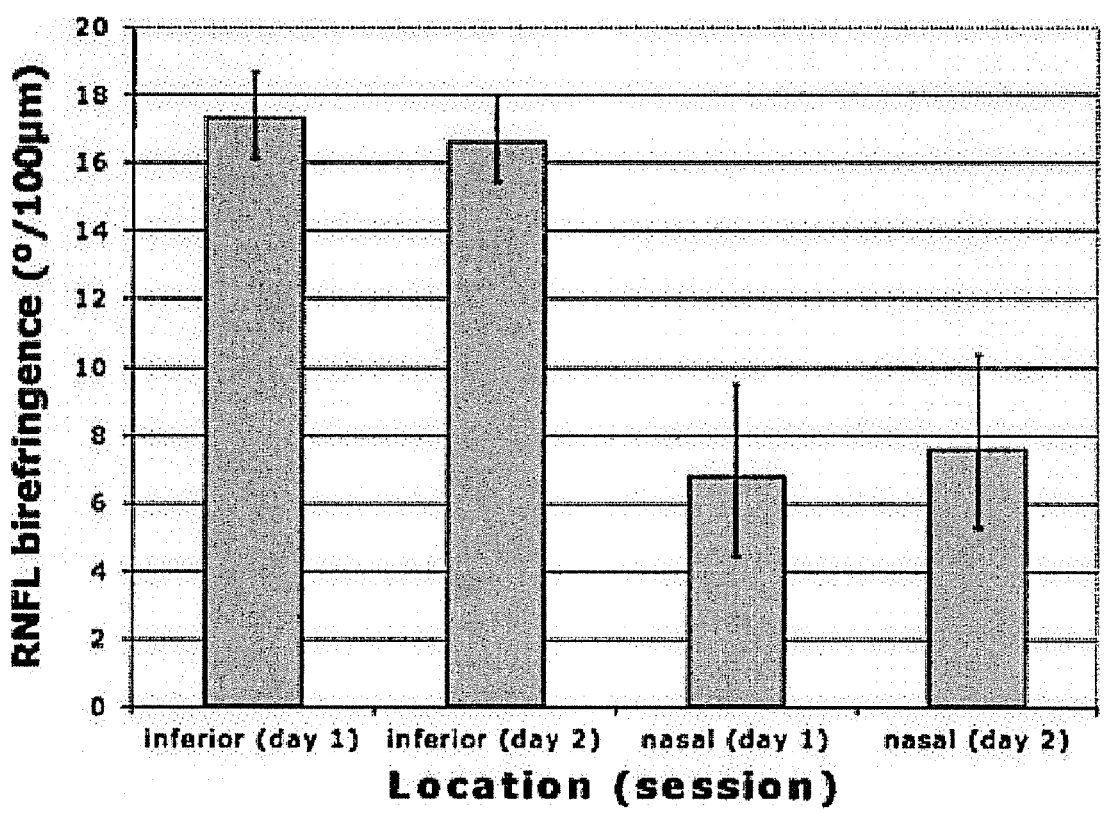
FIG. 12 is a graph of the RNFL birefringence (Δn) in locations 1 mm inferior and 1 mm nasal to the center of the ONH on two separate days, where the error bars indicate approximate PS-OCT birefringence sensitivity.

Sources of error in birefringence calculation include (1) uncertainty in the bulk refractive index (±2.5%); and (2) uncertainty in δ due to polarimetric speckle noise which lingers after ensemble averaging. After averaging $N_A$=36 speckle fields, polarimetric speckle noise was calculated [Eq. (16)] to be $\sigma_{speckle}$=4°, resulting in an approximate double-pass retardation uncertainty of ±2° or a single-pass retardation uncertainty of ±1°. Uncertainty estimated using the mean error between variable birefringent phantom measurements and linear fit was ±1°. These uncertainties give error bars on the RNFL birefringence measurements and also a quantitative value for the birefringence sensitivity of the PS-OCT configuration, as shown in FIG. 12. Additional averaging ($N_A$>36) would decrease uncertainty in δ and further increase the sensitivity of PS-OCT configuration, but with a cost of decreased lateral resolution and increased acquisition time.

Example 3

Form-Biattenuance in Fibrous Tissues

Ex Vivo Rat Tendon Measurements

Four mature, freshly-euthanized Sprague-Dawley rats were obtained. To collect tail tendon specimens, each tail was cut from the body and a longitudinal incision the length of the tail was made in the skin on the dorsal side. Skin was peeled back and tertiary fascicle groups were extracted with tweezers and placed in phosphate buffered saline solution to prevent dehydration before imaging. Anatomical terminology used is consistent with the structure of the rat tail tendon. Tertiary fascicle groups were teased apart into individual fascicles with tweezers and placed in a modified cuvette in the sample path of the PS-OCT configuration. The cuvette maintained saline solution around the fascicle, prevented mechanical deformation in the radial direction, and allowed 20 g weights to be attached at each end of the fascicle. Weights provided minimal longitudinal loading in order to flatten the collagen fibril crimp structure present in rat tail tendon. A total of 111 different fascicle locations were imaged from the four rats, each at the location of maximum diameter across its transverse cross-section (as determined by an OCT B-scan image). Achilles tendon specimens from the same rats were harvested in a straightforward manner and imaged while positioned in the modified cuvette with the same loading conditions. Four different Achilles tendons were imaged in 45 different randomly chosen locations. $S_m(z)$ was recorded ($N_A$=64, M=3) at all locations and the multistate nonlinear algorithm estimated ∈ and δ for each location.

To investigate effect of relative depth of light focus within the tissue on the estimated values for δ and ∈, the same location on a single rat tail tendon fascicle was imaged for a range of axial displacements between the rear principal plane of the f=25 mm focusing lens and the fascicle surface. $S_m(z)$ ($N_A$=64, M=3) for ten 50-µm-steps from 0 (focused at surface) to 450 µm (focused deep within fascicle) was recorded.

To investigate effect of different initial separation-angles [$\gamma_m(0)$] on the PS-OCT-estimated values for δ and ∈, a ⅙-wave retarder was placed in the sample path between the LCVR and scanning optics and $S_m(z)$ ($N_A$=64, M=5) recorded from the same location on a single rat tail tendon fascicle for 12 uniformly spaced orientations (between 0° and 165°) of the ⅙-wave retarder fast-axis.

Figure 13A:
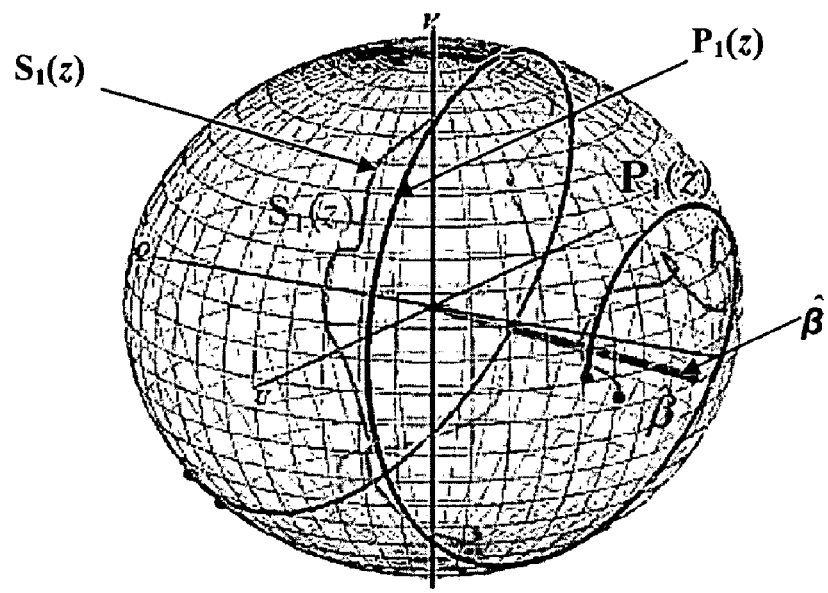
FIG. 13A is a Poincaré sphere showing the depth-resolved polarization data [$S_1$(z)] and associated noise-free model polarization arc [$P_1$(z)] and eigen-axis ($\hat{\beta}$) determined by the multistate nonlinear algorithm in rat tail tendon with relatively high form-biattenuance (Δχ=8.0·10$^{-4}$)
Figure 13B:
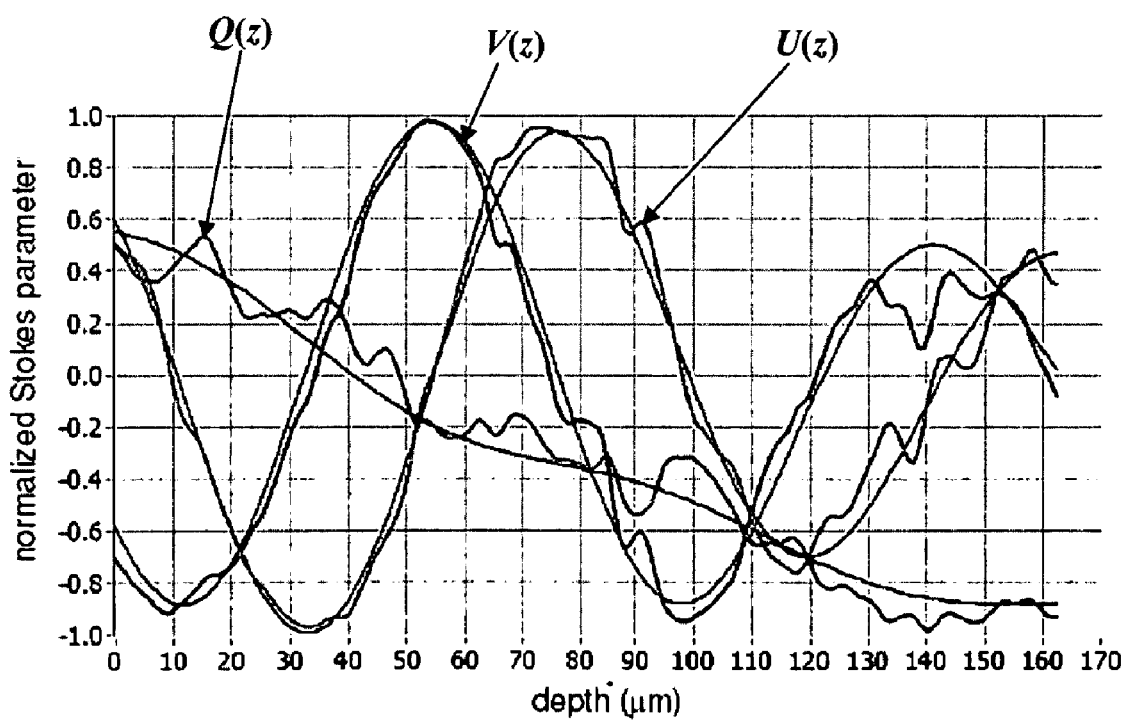
FIG. 13B is a graph for the corresponding normalized Stokes parameters [Q(z), U(z), V(z)] and associated nonlinear fits.
Figure 14A:
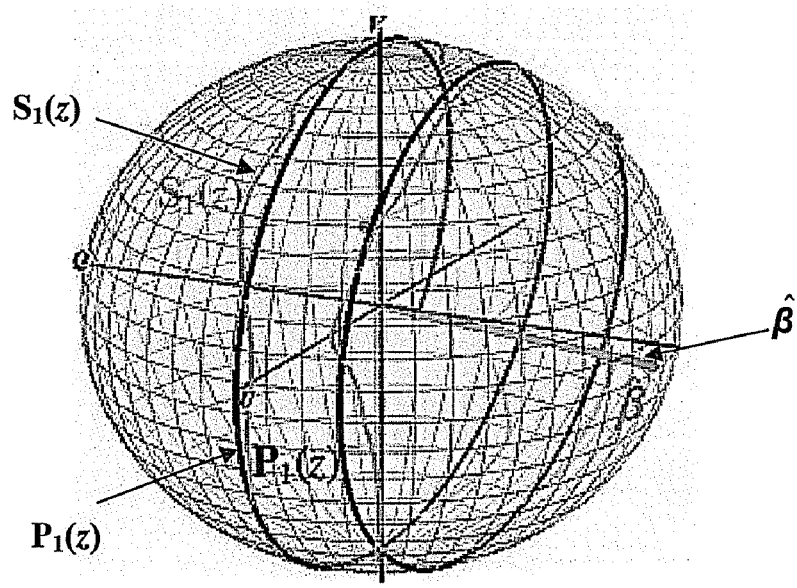
FIG. 14A is a Poincaré sphere showing the depth-resolved polarization data [$S_1$(z)] and associated noise-free model polarization arc [$P_1$(z)] and eigen-axis ($\hat{\beta}$) determined by the multistate nonlinear algorithm in rat tail tendon with relatively low form-biattenuance (Δχ=3.0·10$^{-4}$)
Figure 14B:
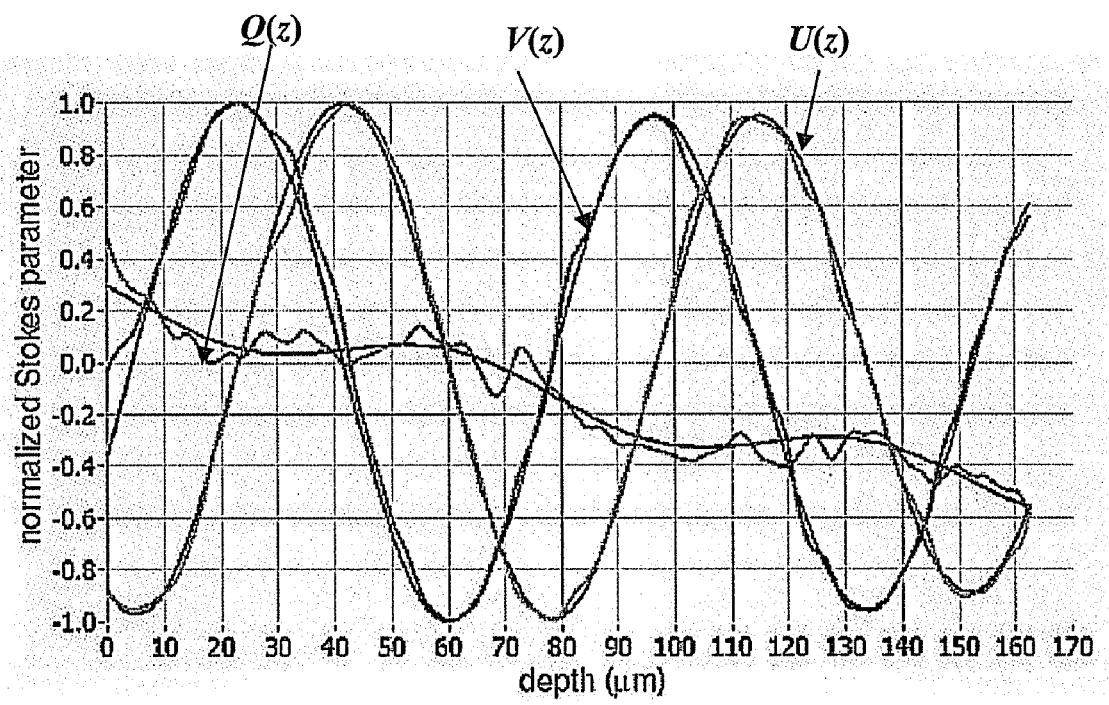
FIG. 14B is a graph for the corresponding normalized Stokes parameters [Q(z), U(z), V(z)] and associated nonlinear fits.

For 111 locations in rat tail tendon, mean ±standard deviation and [range] in rat tail tendon form-biattenuance were $\Delta\chi$=5.3·10$^{-4}$±1.3·10$^{-4}$ [3.0·10$_{-4}$, 8.0·10$^{-4}$] and in form-birefringence were $\Delta n$=51.7·10$^{-4}$±2.6·10$^{-4}$ [46.8·10$^{-4}$, 56.3·10$^{-4}$]. FIGS. 13A-B and 14A-B show $S_m(z)$ and $P_m(z)$ plotted on the Poincaré sphere for two different rat tail tendon fascicles with the largest ($\Delta\chi$=8.0·10$^{-4}$), as shown in FIGS. 13A-B, and smallest ($\Delta\chi$=3.0·10$^{-4}$), as shown in FIGS. 14A-B form-biattenuances detected. Form birefringence for the two fascicles shown in FIGS. 13A-B and 14A-B were $\Delta n$=47.4·10$^{-4}$ and $\Delta n$=55.2·10$^{-4}$ respectively. Polarimetric signal-to-noise ratio (PSNR) ranged from 51 to 155 and standard deviation of polarimetric speckle noise ($\sigma_{speckle}$) was approximately 0.22 rad for the 111 rat tail tendon locations measured. A single incident polarization state (m=1) is shown for simplicity. (a) $S_m(z)$ for tendon with relatively high form-biattenuance ($\Delta\chi$=8.0·10−4) collapses toward $\hat{\beta}$ faster than that for (b) tendon with relatively low form-biattenuance ($\Delta\chi$=3.0·10$^{-4}$).

Variation in Form-Biattenuance Versus Relative Focal Depth

For 10 different displacements between the rear principal plane of the f=25 mm focusing lens and the fascicle surface, $\sigma_{speckle}$≈0.22 rad and mean ±standard deviation in relative-attenuation were ∈=1.42±0.022 rad and in phase retardation were δ=11.5±0.034 rad. Thickness of the tendon specimen was $\Delta z$=360 μm.

Variation in Form-Biattenuance Versus ⅙-Wave Retarder Axis Orientation

For 12 orientations of the ⅙-wave retarder axis, mean ±standard deviation in relative-attenuation were ∈=1.54±0.096 rad and in phase retardation were δ=13.1±0.046 rad. $\sigma_{speckle}$ increased exponentially from 0.066 rad for a small initial separation-angle of $\gamma_m(0)$=0.81 rad up to $\sigma_{speckle}$=0.69 rad for a large $\gamma_m(0)$=3.0 rad. Thickness of the tendon specimen was $\Delta z$=383 μm.

Rat Achilles Tendon

Figure 15A:
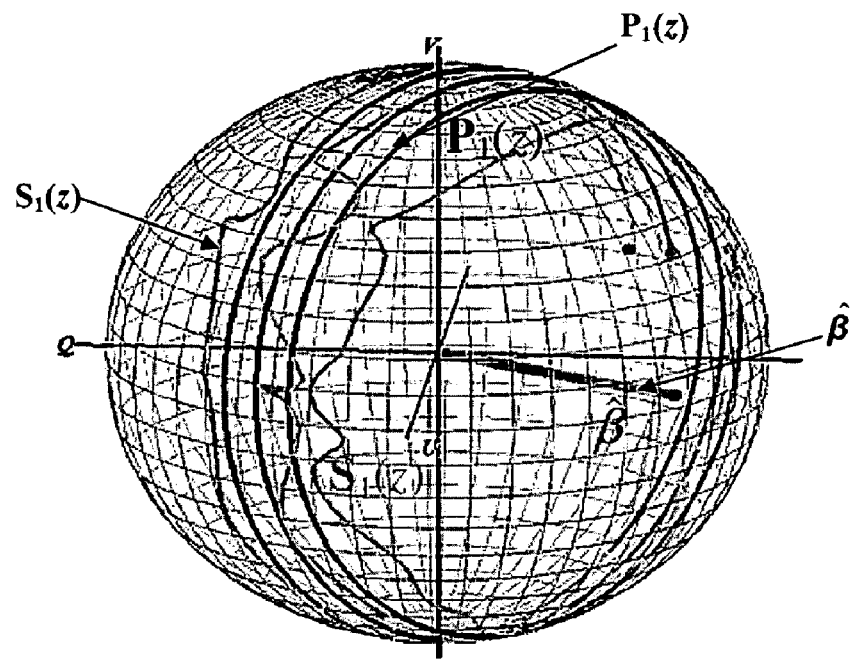
FIG. 15A is a Poincaré sphere showing $S_1$(z) and associated $P_1$(z) and $\hat{\beta}$ determined by the multistate nonlinear algorithm in rat Achilles tendon.
Figure 15B:
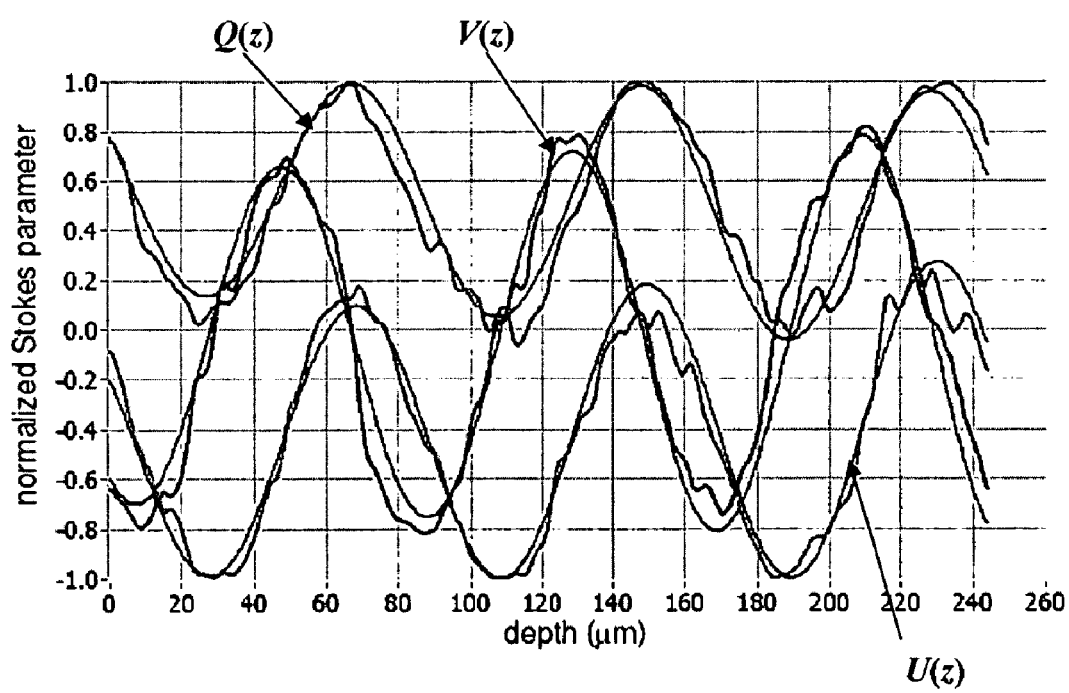
FIG. 15B is the corresponding normalized Stokes parameters of FIG. 15A and associated nonlinear fits.

For 45 locations in rat Achilles tendon, mean±standard deviation and [range] in rat Achilles tendon form-biattenuance were $\Delta\chi$=1.3·10$^{-4}$±0.53·10$^{-4}$ [0.74·10$^{-4}$, 3.2·10$^{-4}$] and in form-birefringence were $\Delta n$=46.9·10$^{-4}$±5.9·10$^{-4}$ [32.9·10$^{-4}$, 56.3·10$^{-4}$]. FIGS. 15A-B shows $S_m(z)$ and $P_m(z)$ plotted on the Poincaré sphere for the location in which the form-biattenuance was the lowest of all tendon specimens studied ($\Delta\chi$=0.74·10$^{-4}$). PSNR ranged from 76 to 175 and $\sigma_{speckle}$≈0.20 rad for the 45 rat Achilles tendon locations measured.

A single incident polarization state (m=1) is shown for simplicity. Form-biattenuance in this specimen ($\Delta\chi$=3.2°/100 μm) is lower than for specimens shown in FIGS. 13A-B and 14A-B and spiral collapse toward $\hat{\beta}$ is correspondingly slower.

Ex Vivo Chicken Tendon Measurements 57 randomly chosen locations were imaged from tendons extracted from the proximal end of chicken thighs obtained at a local grocery store. Temperature variations (freezing/thawing or refrigeration) and postmortem time prior to characterization by PS-OCT were unknown. Extracted tendon specimens were kept hydrated in the modified cuvette and imaged without mechanical loading. $S_m(z)$ was recorded ($N_A$=64, M=3) at all locations and the multistate nonlinear algorithm was used to estimate ∈ and δ for each location.

For 57 locations in chicken drumstick tendon, mean±standard deviation and [range] in chicken drumstick tendon form-biattenuance were $\Delta\chi$=2.1·10$^{-4}$±0.3·10$^{-4}$ [1.4·10$^{-4}$, 3.1·10$^{-4}$] and in form-birefringence were $\Delta n$=44.4·10$^{-4}$±1.9·10$^{-4}$ [38.4·10$^{-4}$, 48.4·10$^{-4}$]. PSNR ranged from 42 to 96 and $\sigma_{speckle}$≈0.28 rad for the 57 chicken drumstick tendon locations measured.

In Vivo Primate Retinal Nerve Fiber Layer Measurements

Details of the animal protocol for PS-OCT characterization of the in vivo primate retinal nerve fiber layer (RNFL) were given in EXAMPLE 2. $S_m(z)$ was recorded ($N_A$=36, M=6) on two different days for six locations distributed in a 100 μm region around a point 1 mm inferior to the optic nerve head ("ONH") center and six locations distributed in a 100 μm region around a point 1 mm nasal to the ONH center.

Figure 16A:
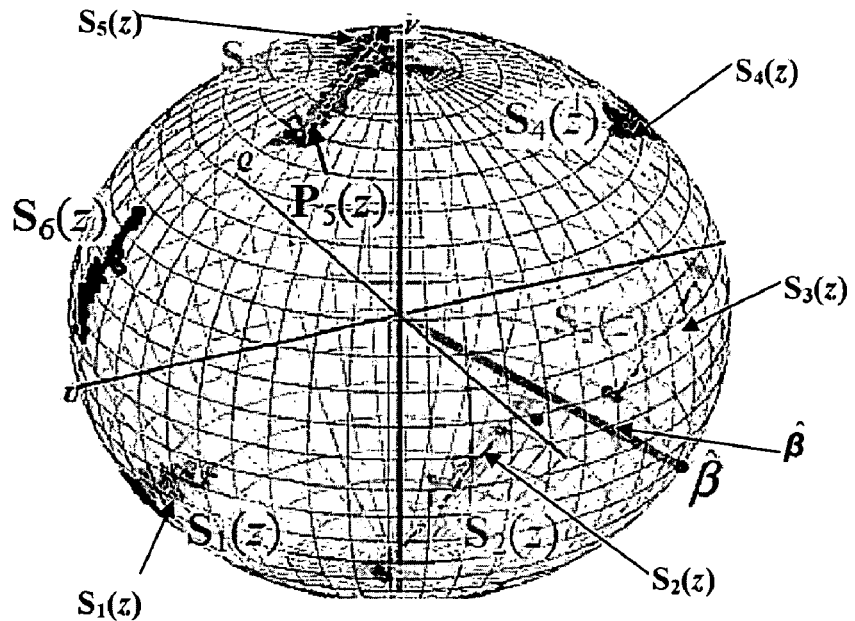
FIG. 16A is a Poincaré sphere showing the $S_m$(z) and associated $P_m$(z) and $\hat{\beta}$ for in vivo primate RNFL for M=6.
Figure 16B:
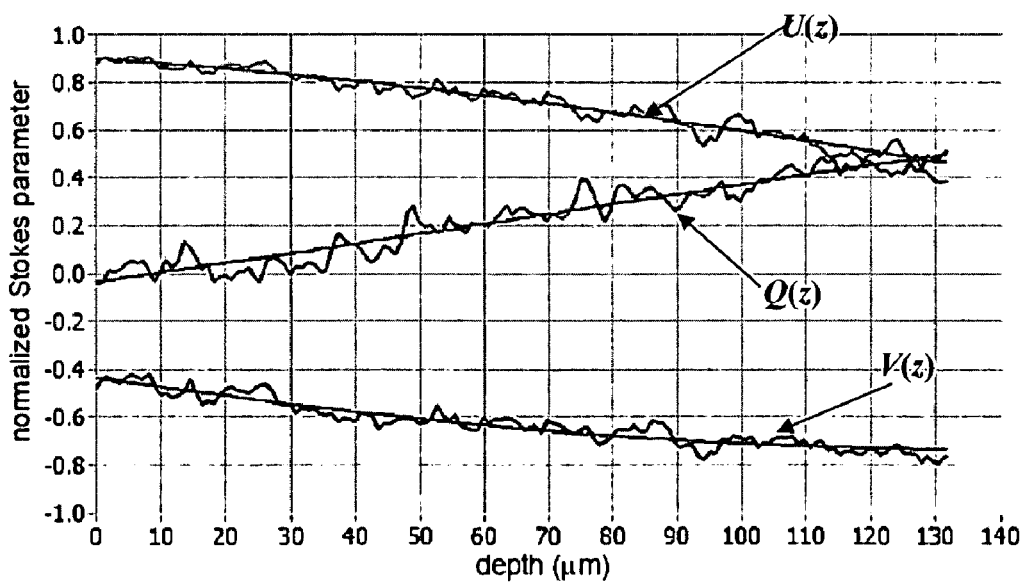
FIG. 16B is the corresponding normalized Stokes parameters [Q(z), U(z), V(z)] and associated nonlinear fits are shown for a single incident polarization state (m=1).

The mean±standard deviation and [range] in form-biattenuance for the six locations within a 100 μm region around a point 1 mm inferior to the ONH center: $\Delta\chi$=0.18·10$^{-4}$±0.09·10$^{-4}$ [0.07·10$^{-4}$, 0.33·10$^{-4}$] on day 1 and $\Delta\chi$=0.18·10$^{-4}$±0.13·10$^{-4}$ [0.06·10$^{-4}$, 0.42·10$^{-4}$] on day 2. Average RNFL thickness in this region was 166 μm and average relative-attenuation (F) was 0.023 radians. FIG. 16A shows typical $S_m(z)$ and $P_m(z)$ plotted on the Poincaré sphere for the region 1 mm inferior to the ONH center in the primate RNFL. PSNR ranged from 3 to 16 and $\sigma_{speckle}$≈0.06 rad for the six inferior locations measured. In the region 1 mm nasal to the ONH center, RNFL thickness averaged 50 μm and PSNR was too low for reliable estimates of $\Delta\chi$ in the nasal region of the primate RNFL. The RNFL exhibits only a fraction of a wave of phase retardation compared to multiple waves exhibited by tendon specimens in FIGS. 13A and 14A.

Variation in Measurements of Form-Biattenuance

Uncertainty in phase retardation ($u_\delta$) is predominantly due to polarimetric speckle noise ($\sigma_{speckle}$) which lingers after ensemble-averaging. Arc length ($l_{arc}$) has approximately the same functional dependence on δ and ∈, therefore uncertainty in relative-attenuation ($u_\in$) is expected to be similar to $u_\delta$ for a given $\sigma_{speckle}$, though additional experiments in a controlled model are necessary to verify the relationship between $u_\in$, $u_\delta$, and $\sigma_{speckle}$. Uncertainties in form-birefringence ($u_{\Delta n}$) or form-biattenuance ($u_{\Delta\chi}$) are dependent on $u_\delta$ or $u_\in$ as well as the specimen thickness ($\Delta z$), which complicates comparison of $u_{\Delta n}$ or $u_{\Delta\chi}$ between specimens or between other variations of PS-OCT configuration. For the rat and chicken tendon specimens studied ($N_A$=64), $\sigma_{speckle}$ ranged from 0.20 to 0.28 rad, giving uncertainties ($u_\delta$ and $u_\in$) due to polarimetric speckle noise no higher than ±0.07 rad. Corresponding uncertainty in form-biattenuance for a $\Delta z$=160-μm-thick specimen is $u_{\Delta\chi}$≈±0.57·10$^{-4}$. In primate RNFL ($N_A$=36), $\sigma_{speckle}$≈0.06 rad corresponds to $u_\in$≈±0.015 rad or $u_{\Delta\chi}$≈±0.12·10$^{-4}$ for an RNFL thickness of $\Delta z$=166 μm.

The range of systematic variation in measurements of δ and ∈ due to placement of the beam focus was negligible. Variation in measured ∈ (6.2%) due to different initial separation-angles [$\gamma_m(0)$] was higher than variation in δ (0.35%). Interestingly, $\sigma_{speckle}$ has a roughly exponential dependence on $\gamma_m(0)$. Large initial separation angles [$\gamma_m(0)$≈π] correspond to incident polarization states [$S_m(0)$] near the preferentially attenuated eigenpolarization; therefore, it is expected that these $S_m(0)$ will have lower detected intensity and relatively higher noise variation on the Poincaré sphere than $S_m(0)$ with lower $\gamma_m(0)$. Additional experiments may characterize completely the dependence of $\sigma_{speckle}$ on $\gamma_m(0)$. Because $W_m(z)$ [Eq. (33)] decreases with increasing $\sigma_{speckle}$, states with large $\gamma_m(0)$ are weighted less by the multistate nonlinear algorithm when estimating δ and ∈. Inspection of the FIGS. 13B, 14B, 15B, and 16B reveals that $\sigma_{speckle}$ does not increase significantly versus depth (z) for the limited tissue thicknesses studied. Therefore, it is not expected that reduced collection of light backscattered from deeper in the tissue significantly affects the estimates of ∈ for the range of depths probed.

Form-Biattenuance Comparison with Other Values

The form-biattenuance values measured in tendon are significantly higher than those approximated from D/$\Delta z$ values reported in chicken tendon ($\Delta\chi$=0.8·10$^{-4}$) or in porcine tendon ($\Delta\chi$=0.17·10$^{-4}$). The range of $\Delta\chi$ values measured in a substantial number of specimens of rat tail tendon (3.0·10$^{-4}$ to 8.0·10−4 for N=111), rat Achilles tendon (0.74·10$^{-4}$ to 3.2·10$^{-4}$ for N=45), and chicken drumstick tendon (1.4·10$^{-4}$ to 3.1·10$^{-4}$ for N=57) demonstrate that a sizable inter-species and intra-species variation is present in tendon form-biattenuance.

Loading the tendon specimens with 20 g weights was to extract tendon exhibits with a well-known crimp structure in which the constituent collagen fibers are not regularly aligned. Applying a small load to the tendon effectively flattens the crimp, providing a reproducible specimen which can be modeled using the Jones matrix in Eq. (30) for a homogeneous linear retarder/diattenuator and giving results that can be objectively compared. And the in vivo state of tendon is more similar to the slightly loaded state than to a completely relaxed or non-loaded state, especially considering that even minimal muscle tone would cause slight tension in connected tendons. Variance in the measurements of rat tail tendon biattenuance and birefringence was substantially reduced by loading, but mean $\Delta\chi$ and $\Delta n$ was not noticeably affected. For the purpose of comparison with previous results on chicken tendon, chicken tendon specimens were not mechanically loaded. Measured values of form-biattenuance of chicken tendon ($\Delta\chi \gtrsim 1.4 \cdot 10^{-4}$) are nearly a factor of two higher than previously reported ($\Delta\chi = 0.8 \cdot 10^{-4}$).

Because the small-angle approximation introduces only minimal error in previously reported values of $D/\Delta z$, discrepancy with $\Delta\chi$ values is not due to conversion from diattenuation (D) to relative-attenuation ($\in$). Difference in values may be due to wide inherent anatomical variation in form-biattenuance, nonstandard tissue extraction and preparation, or large uncertainty in the methodologies. Details such as tissue freshness, anatomical origin of the harvested specimens, and detailed description of the expected uncertainty are not available. Additionally, crimp structure present in non-loaded tendon specimens could cause spatial variations in collagen fiber orientation over the sample beam diameter, resulting in poor agreement with a homogeneous linear retarder/diattenuator model [Eq. (30)] and artifacts in measurements of $\Delta\chi$.

The validity of using diattenuation-per-unit-depth ($D/\Delta z$) as an approximation for $\in/\Delta z$ (or $\Delta\chi$) is dependent on the acceptable uncertainty for a particular application. For example, using the rat tail tendon results presented ($\in=1.54 \pm 0.096$ rad), the percentage error is 6.2% due to $\frac{1}{8}$-wave retarder orientation. Using Eq. (31), the corresponding diattenuation is $D=\tanh(1.54)=0.91$. Because $\in$ increases linearly with depth, this tendon ($\Delta z=383$ μm) has relative-attenuation-per-unit-depth of $\in/\Delta z=1.54$ rad/383 μm=0.004 rad/μm or form-biattenuance $\Delta\chi=5.3 \cdot 10^{-4}$. Expressing this as diattenuation-per-unit-depth $D/\Delta z=0.91/383$ μm=0.0024/μm results in an error of 40%, which is much higher than the next largest error source (6.2%) and may be unacceptable for many applications. Additional reduction in $\sigma_{speckle}$ will allow more sensitive determination of $\in$. For arbitrarily large PSNR, the small-angle approximation is invalid for any specimen.

Diattenuation by PS-OCT has been primarily concerned with its effect on estimates of phase retardation or form birefringence. The reasonable estimates of phase retardation can be made in tendon and muscle even if diattenuation is physically present but is ignored in the model. Indeed, one can discern from the "damped" sinusoidal nature of the normalized Stokes parameters vs. depth (FIGS. 13A-B and 14A-B) that the frequency of sinusoidal oscillation (proportional to form-birefringence) can be estimated without considering the "damped" amplitude variation (due to form-biattenuance) when multiple periods of oscillation (multiple waves of phase retardation) are present. Results show that relative contribution to polarimetric transformations from $\Delta n$ and $\Delta\chi$ varies largely. In rat tail tendon, $\Delta\chi/\Delta n$ was measured as high as 0.17 and in Achilles tendon as low as 0.017. In instances where either 1) $\Delta\chi/\Delta n$ is high, 2) multiple periods of oscillation are not present, or 3) PSNR is low, accuracy in estimates of $\Delta n$ ($\Delta\chi$) will be reduced if form-biattenuance (form-birefringence) is ignored.

Polarimetric speckle noise ($\sigma_{speckle}$) depends on the initial separation-angle [$\gamma_m(0)$]. Based on this observation, the number of incident polarization states (M) and the selection of those states [$S_m(0)$] relative to $\hat{\beta}$ employed by a particular PS-OCT approach will affect the ability to accurately distinguish between $\Delta n$ and $\Delta\chi$. Approaches using M=2 incident polarization states which are positioned orthogonally to each other in their representation on the Poincaré sphere and are suited for detecting $\delta$ and $\Delta n$. Alternatively, M=2 polarization states which are oriented parallel and perpendicular to the optic axis in physical space (and opposite to each other in their representation on the Poincaré sphere) may provide the best estimates of $\in$ and $\Delta\chi$. These considerations suggest that selecting at least M=3 incident polarization states for optimal determination of both form-birefringence and form-biattenuance, regardless of the particular PS-OCT approach used. The multistate nonlinear algorithm discriminates between $\Delta n$ and $\Delta\chi$ by restricting contributions to movement of $S_m(z)$ on the Poincaré sphere from each phenomenon into two orthogonal planes and seamlessly incorporates M=3 incident polarization states while avoiding issues related to overdetermined Jones matrices.

Because form-birefringence and form-biattenuance arise from light scattering by nanometer-sized anisotropic structures, development of sophisticated models relating $\Delta n$ and $\Delta\chi$ to underlying microstructure will allow use of the PS-OCT configurations for noninvasively and invasively quantifying fibrous constituents (e.g., neurotubules in the RNFL or collagen fibers in tendon) which are smaller than the resolution limit of light microscopy. A portion of the tendon birefringence may be due to intrinsic birefringence on the molecular scale. Because biattenuance in tendon or RNFL may arise from interactions on the nanometer scale, form-biattenuance and biattenuance may be used interchangeably.

The small-angle approximation introduces minimal error for diattenuation-per-unit-depth ($D/\Delta z \approx \in/\Delta z$) observed in thin tissue specimens ($\Delta z<1$ mm). Substantial measurements on tissues have a diattenuation (D) that is outside the range of the small-angle approximation and cannot be meaningfully reported on a diattenuation-per-unit-depth ($D/\Delta z$) basis. Biattenuance ($\Delta\chi$) requires no approximation and is analogous and complementary to a well-understood term, birefringence ($\Delta n$). Use of the term biattenuance overcomes the need to specify when a diattenuation-per-unit-depth approximation is valid. Consistency in definitions between birefringence ($\Delta n$) and biattenuance ($\Delta\chi$) or between phase retardation ($\delta$) and relative-attenuation ($\in$) allow a meaningful and intuitive comparison of the relative values (i.e. $\Delta\chi/\Delta n$, $\in/\delta$) of amplitude and phase anisotropy in any optical medium or specimen. The availability of narrow line-width swept-source lasers allows construction of Fourier-domain PS-OCT instruments having scan depths far longer than current PS-OCT instruments. By using swept laser sources and hyperosmotic agents to reduce scattering in tissue, the PS-OCT configuration probes significantly deeper into tissue specimens than 1-2 mm, likely making the small-angle approximation invalid even in tissues with low biattenuance. A narrow line width laser source will allow longer scan distances as described in the common path spectral domain PS-OCT configuration. The ability to determine the biattenuance with a spectral domain approach is dependent on the multi-state fitting algorithm or similar approach as described above. The spectral domain approach, as described in the PS-OCT configuration 10 and 200, allows faster acquisition of the data and provide improved estimates (relative to time domain systems) of birefringence and biattenuance. PS-OCT characterizes non-biological samples which may have higher D and not satisfy the small-angle approximation. Biattenuance is useful in employing other polarimetric optical characterization techniques, which can detect anisotropically scattered light and for which dichroism is therefore inappropriate. Finally, although the term "depth-resolved" is frequently used in the context of either "measured in the depth dimension" or "local variation in a parameter versus depth [e.g., $\Delta\chi(z)$]", biattenuance is independent of the particular interpretation. The first interpretation may be applied to biattenuance, but the multistate nonlinear algorithm can be extended in a straightforward manner to provide local variation in biattenuance versus depth [$\Delta\chi(z)$].

Exemplary Conclusion

Biattenuance ($\Delta\chi$) is an intrinsic physical property responsible for polarization-dependent amplitude attenuation, just as birefringence ($\Delta n$) is the physical property responsible for polarization-dependent phase delay. Diattenuation (D) gives the quantity of accumulated anisotropic attenuation over a given depth ($\Delta z$) by a given optical element. The nonlinear dependence of diattenuation on depth motivated introduction of relative-attenuation ($\in$), which depends linearly on depth, maintains parallelism and consistency with phase retardation ($\delta$) in Eq. (30), and is a natural parameter in depth-resolved polarimetry such as PS-OCT. The mathematical relationships between these parameters were given in Eqs. (27), (29), and (31).

The PS-OCT configurations includes: (1) theoretical and experimental validation for a new term in optical polarimetry, biattenuance ($\Delta\chi$), which describes the phenomenon of anisotropic or polarization-dependent attenuation of light amplitudes due to absorption (dichroism) or scattering; (2) detailed mathematical formulation of $\Delta\chi$ and relative-attenuation ($\in$) in a manner consistent with established polarimetry (i.e., birefringence and phase retardation), and mathematical relationships to related polarimetric terms diattenuation and dual attenuation coefficients; (3) analytic expression for trajectory of normalized Stokes vectors on the Poincaré sphere in the presence of both birefringence and biattenuance; (4) expression for arc length ($l_{arc}$) and PSNR of normalized Stokes vector arcs on the Poincaré sphere in the presence of both birefringence and biattenuance; (5) modification of a multistate nonlinear algorithm to provide sensitive and accurate estimates of $\in$ and $\Delta\chi$ in addition to $\delta$ and $\Delta n$; (6) incorporation of a scalar weighting factor [$W_m(z)$] into the multistate nonlinear algorithm; (7) substantial ex vivo and in vivo experimental data in several species and two tissue types to demonstrate large variation in $\Delta\chi$, as well as interpretation of this data in the context of previously reported values; (8) description of the expected uncertainty in our measurements of $\in$ and $\Delta\chi$; and (9) introduction of a physical model for birefringent and biattenuating optical media.

Form-biattenuance and form-birefringence are closely related but physically distinct phenomena which may convey different information about tissue microstructure. The form-biattenuance diagnostic capabilities remain with how accurate the determination of form-biattenuance and form-birefringence are concurrently used in biomedical research or clinical diagnostics. Form-biattenuance may quantify the effect of tendon crimp on $\Delta n$ and $\Delta\chi$ and to establish the acceptable uncertainty in biattenuance for diagnosis of various pathological tissue states. Other fibrous tissues at multiple imaging wavelengths may refine the physical model and establish a comprehensive anatomical range for biattenuance.

Example 4

Figure 17:
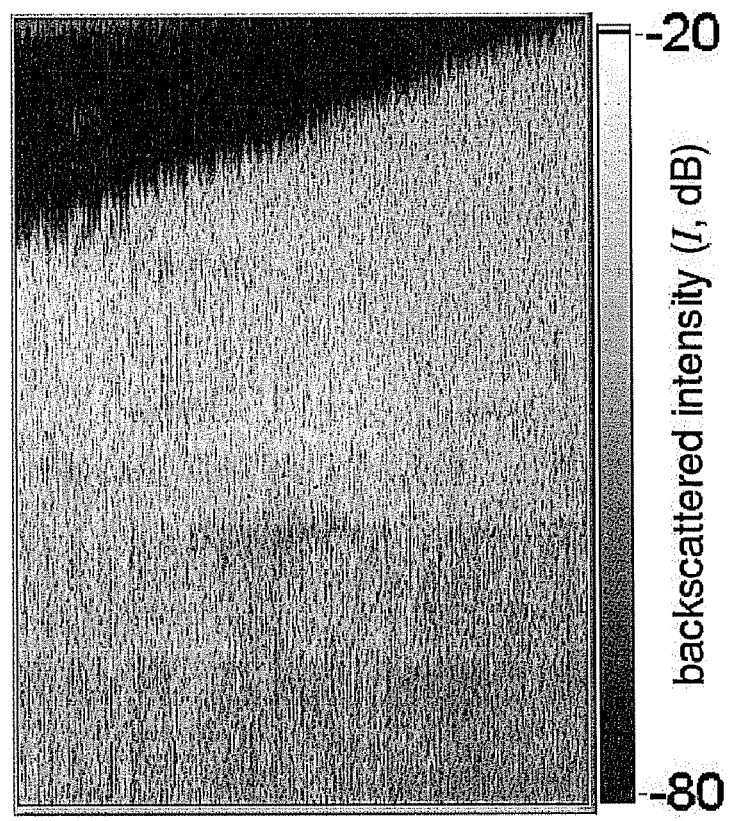
FIG. 17 is an intensity B-scan of annulus fibrous, the image is 0.35 mm wide, 0.5 mm deep, and intensity is plotted logarithmically using arbitrary units.

Fiber Orientation Contrast for Depth-Resolved Identification of Structural Interfaces in Birefringent Tissue Procedures for calibrating the constant retardation offset in the instrument and for preparing the intervertebral disc specimen for PS-OCT imaging were given above. The lateral (x-y dimension) scan pattern used consisted of 20 uniformly spaced clusters of $N_A=36$ A-scans (720 A-scans total). The $N_A=36$ A-scans in each cluster were acquired in slightly displaced spatial locations on a 6 6 square grid (25 μm 25 μm) to uncorrelate speckle noise. A-scans acquired in this x-y scan pattern were flattened into an intensity B-scan image (I(x, z), FIG. 17), resulting in the slight sawtooth artifact apparent on the specimen surface. No averaging was performed in the intensity B-scan image displayed in FIG. 17. Depth-resolved polarization data ($S_m(z)$) was acquired for M=6 different incident polarization states and then ensemble averaging of $N_A=36$ A-scans was performed to reduce polarimetric speckle noise ($\sigma_{speckle}$) in each cluster.

For each of the 20 clusters in the x-dimension, the following procedure was carried out using only the averaged depth-resolved polarization data ($S_m(z)$) for that cluster. First, the top surface of the specimen was identified as the depth ($z_{top}$) at which $S_m(z)$ ceased to exhibit random noise fluctuations and began tracing regular arcs on the Poincaré sphere. Second, depths below $z_{top}$ at which the trajectories of $S_m(z)$ showed a spike in curvature ($\kappa(z)$, FIG. 18A-B) were identified as discrete changes in fiber orientation and were attributed to interfaces between lamellae. Only k=3 lamellae for a single incident polarization state (m=1) are shown for simplicity in FIGS. 18A-B. Lamellar thickness ($\Delta z_k$) was recorded as the distance between interfaces for each lamella k and was compensated by the tissue refractive index (n=1.40). Normalization of Stokes vectors ensures that intensity contrast information (I(z)) does not contribute to identification of lamellar interfaces. Data from adjacent clusters were not used in this procedure.

The high sensitivity nonlinear fitting algorithm in Example 3 was then applied to estimate phase retardation ($\delta_1$), relative attenuation ($\in_1$) and eigenaxis ($\hat{\beta}_1$) for the top lamella (k=1) and then successive $\delta_k$, $\in_k$, and $\hat{\beta}_k$ for k=2 were estimated after iterative compensation of $\delta_{k-1}$ and $\in_{k-1}$.

Exemplary Results

Figure 19:
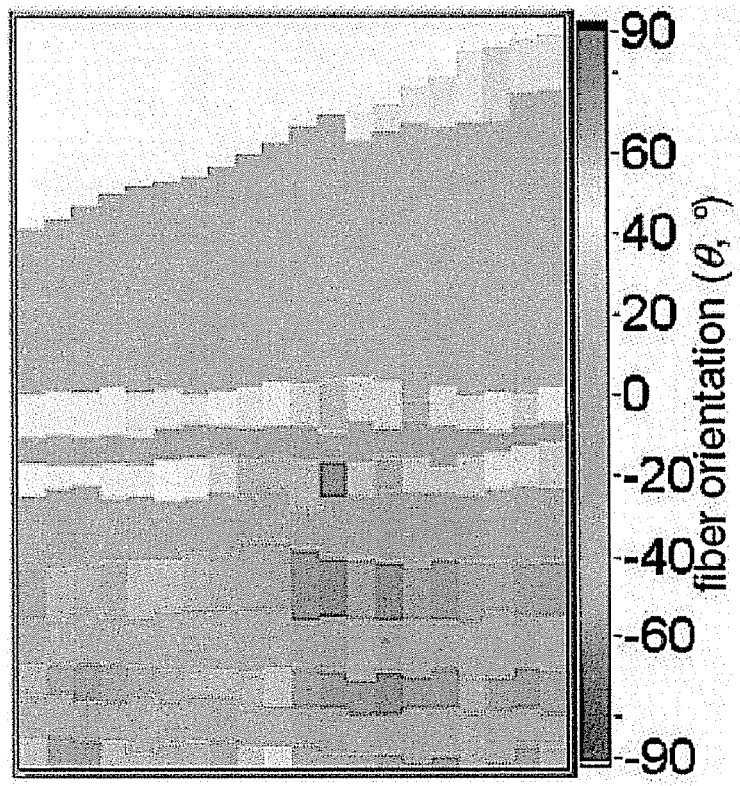
FIG. 19 a fiber orientation B-scan [θ(x,z)] of the annulus fibrous specimen shown in FIG. 17, where the fiber orientation (θ) is assigned a false color representing the counterclockwise angle between the fiber axis and the horizontal as viewed along the incident beam.
Figure 20:
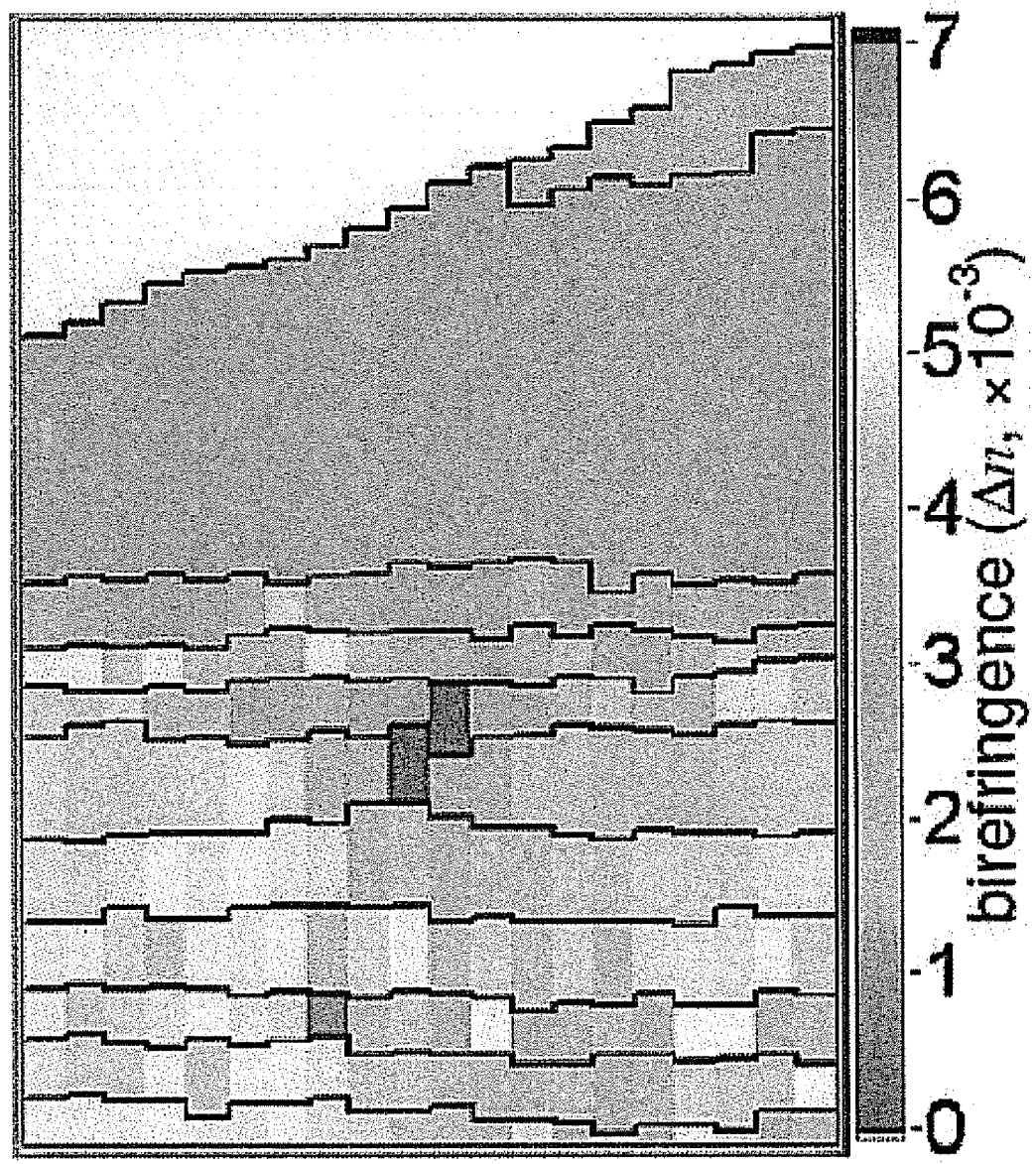
FIG. 20 is a PS-OCT birefringence B-scan [Δn(x,z)] of the annulus fibrous specimen shown in FIG. 17, where the detected interfaces between lamellae are represented by black lines.

Fiber orientation ($\theta_k$) and birefringence ($\Delta n_k$) for each lamella k and for all 20 lateral clusters were calculated from $\Delta z_k$, $\delta_k$ and $\hat{\beta}_k$ as discussed above and assembled into B-scan images of depth-resolved fiber orientation ($\theta(x, z)$, FIG. 19) and birefringence ($\Delta n(x, z)$, FIG. 20). FIG. 19 shows the lamellar structure is clearly visible due to high contrast between fiber orientations in successive layers. Relative attenuation ($\in_k$) was at or below the sensitivity limit for the deeper lamellae in this cartilage specimen and therefore a B-scan image of biattenuance is not shown. The mean and standard deviation in biattenuance in the thick upper layer where $\in$ was above the sensitivity limit are $\Delta\chi=1.02$ $10^{-4}\pm0.31$ $10^{-4}$.

Figure 21:
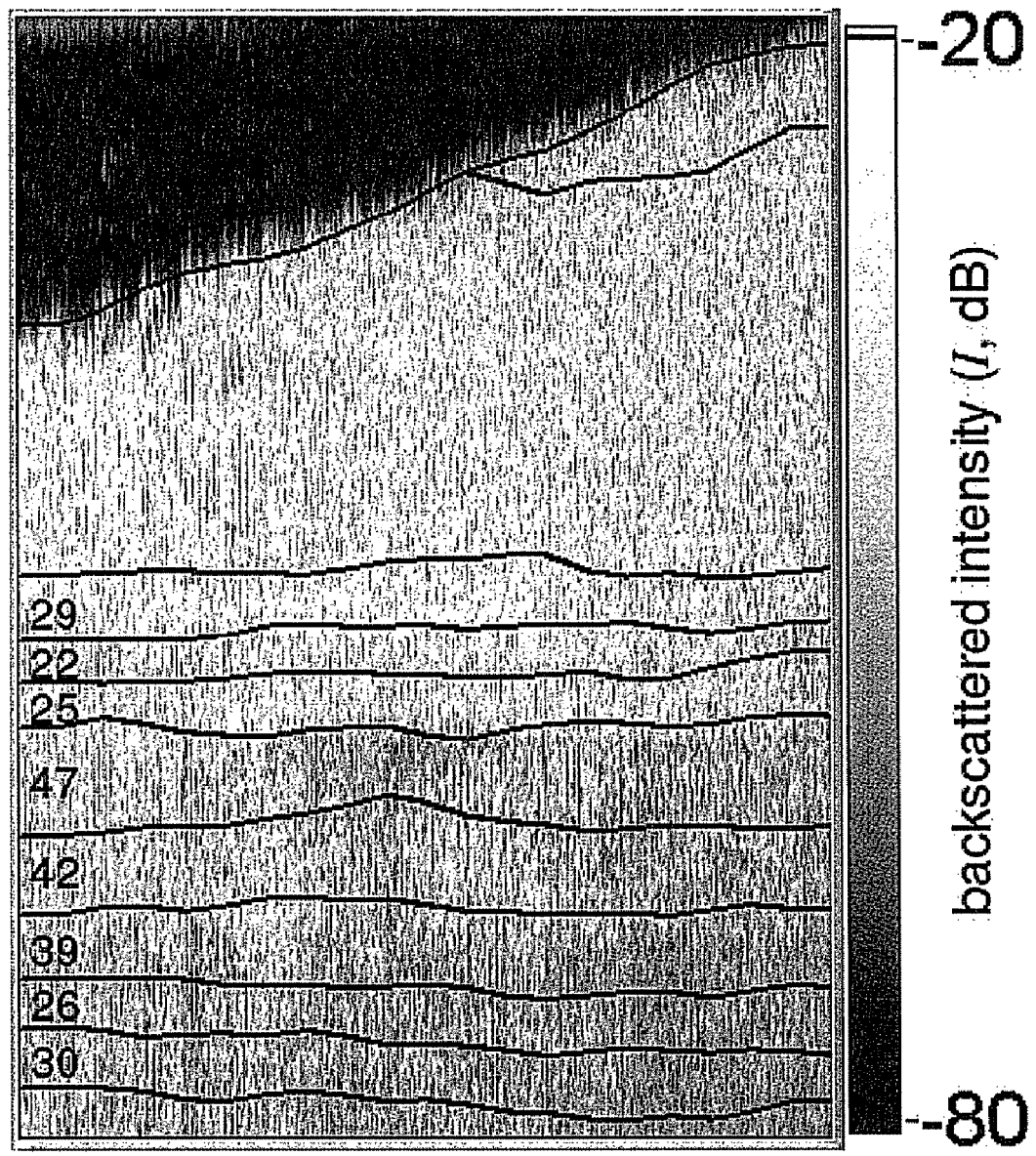
FIG. 21 is an intensity B-scan [I(x,z)] introduced in FIG. 17 with black lines superimposed to indicate structural features (lamellar interfaces) that were not apparent in I(x,z) but were detected in the depth-resolved polarization data [$S_m$(z)], where the numbers on left represent mean thickness of each lamella ($\Delta_k$, μm).

In FIG. 20, black lines indicate lamellar interfaces determined by identifying segments in trajectories of $S_m(z)$ with high curvature ($\kappa(z)$). FIG. 21 shows these interfaces superimposed on the original backscattered intensity OCT B-scan image (I(x, z)). A sliding averaging window (15% of image width) was applied across each interface to smooth black lines in FIG. 21. Quantitative estimates for mean lamellae thickness ($\Delta\bar{z}_k$) are also indicated in FIG. 21.

The determination of boundaries and lamellar thickness ($\Delta\bar{z}_k$) using the trajectory of $S_m(z)$ provides vastly improved contrast over I(x, z) in the annulus fibrous specimen, as shown in FIG. 21. Since backscattered intensity images do not exhibit adequate contrast for detecting these structural details, the technique based only on the depth-resolved polarization state resolves the contrast. This is especially true in cartilage, a tissue in which these structures directly contribute to mechanical and physiological properties.

Improving contrast and identifying lamellar interfaces by detecting changes in relative fiber orientation does not require computationally intensive processing algorithms which are necessary to effectively quantify tissue retardation, diattenuation and fiber orientation (such as fitting of Stokes vector trajectories or Jones matrices). Therefore, the technique is more amenable to real-time image processing necessary in clinical situations. The B-scan image of fiber axis orientation ($\theta(x, z)$, FIG. 19) was constructed using a calibrated PS-OCT configuration and therefore represents the collagen fiber orientation referenced absolutely to the horizontal laboratory frame. For identifying interfaces using the depth-resolved polarization state method, only relative fiber orientation changes must be detected; thus, a fiber-optic rather than bulk-optic PS-OCT configuration has stability and portability advantages in a clinical environment. The method using depth-resolved curvature ($\kappa(z)$) of normalized Stokes vectors ($S(z)$) to identify boundaries in multiple-layered fibrous tissue can be applied to all phase-sensitive PS-OCT configurations that detect depth-resolved Stokes vectors, whether fiber-based or bulk-optic, single-incident-state or multi-incident-state, time-domain or frequency-domain. Following boundary identification, subsequent quantification of fiber orientation (relative or absolute), retardation or diattenuation can be accomplished using the method described in EXAMPLES 2 and 3.

Several additional features are apparent in the $\theta(x, z)$ and $\Delta n(x, z)$ B-scan images. First, a small region of reduced birefringence appears in the middle of the $\Delta n(x, z)$ image, corresponding to a region with slightly lower backscattering intensity in $I(x, z)$. This may be a region containing lower collagen fiber density. Second, an incomplete lamella with reduced birefringence is evident in the top right half of the specimen. Incomplete lamellae are commonly observed in annulus fibrous cartilage. Third, fiber orientation is twisted approximately 15-20° counterclockwise in the right half of the $\theta(x, z)$ image relative to the left half. Finally, increased $\Delta n$ in the lower left region reveals a different collagen fiber structure here.

Optical or electron microscopy histology is well known to not preserve in situ dimensions due to the dehydration process integral in histological preparation and therefore is valuable only for corroboration of general tissue morphology in OCT images. Although histology is the gold standard for pathological diagnoses and identification of tissue type, it is unreasonable to validate quantitative structural dimensions in a specimen by making comparisons between in situ OCT measurements and histology. Other complications frequently arise because histology shrinkage artifacts can occur anisotropically (causing twisting and nonlinear distortion) and registration between OCT images and histology images is imprecise and qualitative at best. Inasmuch as uncertainty in dimensions extracted from an OCT image is due to finite resolution (<5 μm) or uncertainty in tissue refractive index (≈5%), the PS-OCT configurations are more accurate than histology for in situ dimensional analysis of lamellar thickness or fiber orientation in the annulus fibrosis and other tissues exhibiting similar geometries. Additionally, a PS-OCT cross section provides the orientation of fibers into and out of the B-scan plane, whereas a histological analysis cannot reveal this three-dimensional structure without a complex process of registering multiple sections taken parallel to the lamellae at successively deeper locations.

Figure 18A:
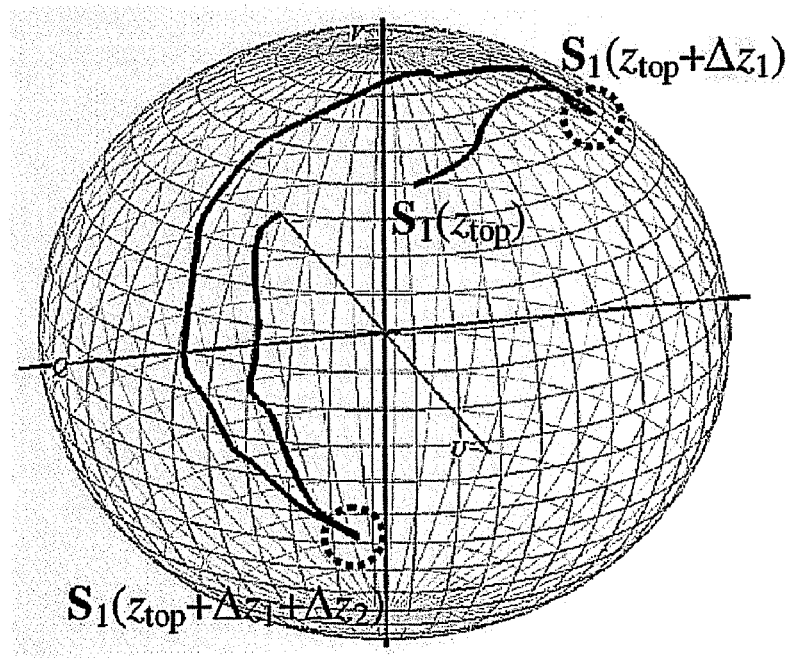
FIG. 18A is a Poincaré sphere with the trajectory of $S_m$(z) for annulus fibrous.
Figure 18B:
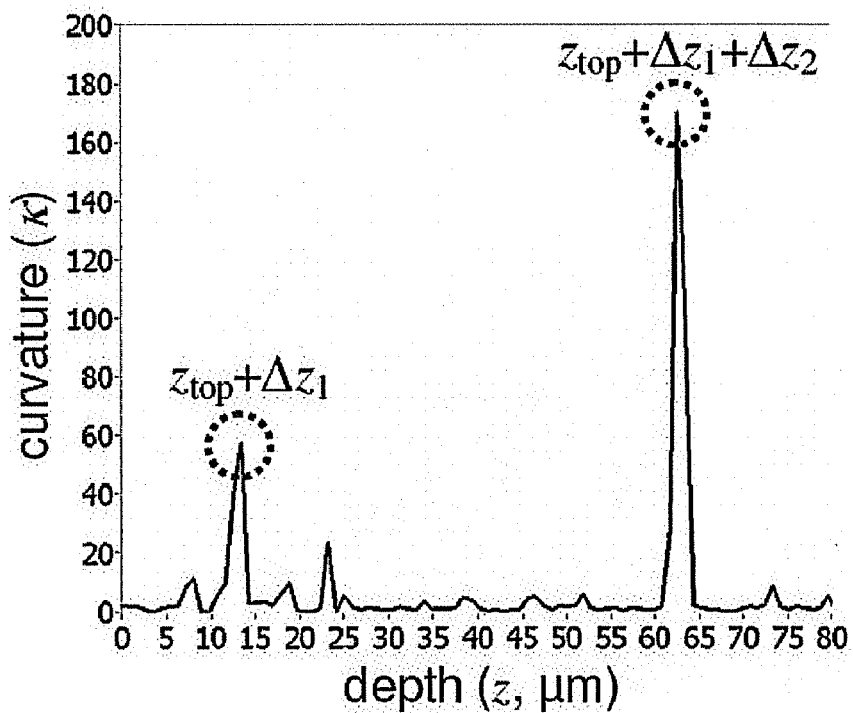
FIG. 18B is a graph of the abrupt changes in trajectory of $S_m$(z) corresponding to lamellar interfaces at $z=z_{top}+\Delta z_1$ and $z=z_{top}+\Delta z_1+\Delta z_2$ are observed as spikes in the curvature [κ(z)] indicated by circles.

Decreasing polarimetric speckle noise ($\sigma_{speckle}$) by ensemble averaging effectively detects changes in $\theta(z)$. Although 90° changes in annulus fibrous fiber orientation ($\theta$) result in dramatic spikes in $\kappa(z)$, as shown in FIGS. 18A-B, other specimens may exhibit less-dramatic $S_m(z)$ trajectory changes which are more difficult to detect without additional $\sigma_{speckle}$ reduction. Algorithms to automatically detect changes in $S_m(z)$ trajectories will be more robust with adequate $\sigma_{speckle}$ reduction. Average $\sigma_{speckle}$ in the specimen was 7° and did not show appreciable variation with depth (z).

The PS-OCT configuration collects ultrastructural information similar to that acquired using histology. Polarization-related properties such as fiber orientation ($\theta(x, z)$) can be used to identify and quantify structural properties (e.g., thickness) in OCT images, regardless of poor contrast in the backscattered intensity B-scan image. Comprehensive PS-OCT imaging of cartilage structures may elucidate injury mechanisms, stress distribution and age variables as well as provide feedback on novel treatment approaches or engineered cartilage-replacement constructs.

The embodiment described herein are based on aspects which have been disclosed by the inventors in disclosure, Kim E and Milner T E, J. Opt. Soc. Am. A. 23: 1458-1467 (2006), hereby incorporated by reference, "High-sensitivity Determination of Birefringence in Turbid Media with Enhanced Polarization-sensitive Optical Coherence Tomography" by Nate J. Kemp et al., J. Opt. Soc. Am. A. 22: 552-560 (2005); "Form-biattenuance in Fibrous Tissues Measured with Polarization-sensitive Optical Coherence Tomography (PS-OCT)" by Nate J. Kemp et al., Optics Express 13: 4611-4628, (2005); and "Fiber Orientation Contrast for Depth-resolved Identification of Structural Interfaces in Birefringent Tissue" by Nate J. Kemp et al., Phys. Med. Biol. 51: 3759-3767 (2006), all of which are incorporated by reference herein.

Additional objects, advantages and novel features of the embodiments as set forth in the description, will be apparent to one skilled in the art after reading the foregoing detailed description or may be learned by practice of the embodiments. The objects and advantages of the embodiments may be realized and attained by means of the instruments and combinations particularly pointed out here.

A polarization sensitive spectral interferometer apparatus and method for analyzing a sample by optical energy reflected from the sample. The polarization sensitive spectral interferometer apparatus and method determines polarization properties of the sample by optical energy reflected from the sample.

What is claimed:

1. A method for analyzing a sample with a spectral interferometer comprising the steps of:
   directing light to the sample with at least one optical fiber of the interferometer including a polarization control element;
   reflecting the light from the sample;
   receiving the light with a receiver of the interferometer;
   determining the polarization properties of the light reflected from the sample with a computer coupled to the receiver; and
   identifying the tissue type of the sample by the polarization properties as function of depth from the depth-resolved birefringence of the sample by employing a multi-state nonlinear algorithm that uses M incident polarization states uniformly distributed on a great circle of the Poincare sphere and utilizing multiple incident polarization states to gives M distinct separation-angles ($\gamma_m$) distributed within the interval [0°, 90°].

2. The method as described in claim 1, wherein M incident polarization state is between 1 and 6.

3. The method as described in claim 1, wherein the determining step further comprises recording the horizontal and vertical interference fringe intensities ($\Gamma_h(z)$ and $\Gamma_y(z)$).

4. The method as described in claim 1, wherein $P(z_j)$ from $S(z_j)$ are extracted from the multi-state nonlinear to determine in retardation ($\delta$) and birefringence ($\Delta n$).

5. The method as described in claim 4, wherein the step of identifying the tissue type of the further comprises maintaining a table look-up in a memory of the computer having known information regarding tissue types and the associated birefringence; and comparing the known information of the associated birefringence properties obtained as a function of depth to the sample with the known information in the table look-up to identify the tissue type.

6. The method as described in claim 5, wherein the directing light to the sample further comprises coupling the optical fiber to a catheter.

7. The method as described in claim 5, wherein the multistate nonlinear algorithm is given by $$R_M = \sum_{m=1}^{M} R_o(S_m(z); \delta, A, P_m(0)),$$

where $R_M$ gives the corresponding M noise-free model polarization arcs $[P_m(z)]$.

8. The method as described in claim 4, wherein the step of identifying the tissue type of the further comprises maintaining a table look-up in a memory of the computer having known information regarding the tissue types and the associated retardation; and comparing the known information of the associated retardation properties obtained as a function of depth to the sample with the known information in the table look-up to identify the tissue type.

9. The method as described in claim 1, wherein the step of identifying the tissue type of the further comprises identifying the tissue type of the sample by the polarization properties as a function of depth from the biattenuance of the sample $\Delta\chi$, which is given by: $\Delta\chi = \chi_s - \chi_f$, where $\chi_s$ and $\chi_f$ attenuation coefficients of the slow and fast eigenpolarizations.

10. The method as described in claim 9, wherein the step of identifying the tissue type of the further comprises maintaining a table look-up in a memory of the computer having known information regarding the tissue types and the associated biattenuance; and comparing the known information of the associated biattenuance properties obtained as a function of depth to the sample with the known information in the table look-up to identify the tissue type.

11. The method as described in claim 1, wherein the step of identifying the tissue type of the further comprises identifying the tissue type of the sample by the polarization properties as a function of depth from the birefringence of the sample by a nonlinear fitting of normalized Stokes vectors from multiple incident polarization states.

12. The method as described in claim 1, wherein the step of identifying the tissue type of the further comprises maintaining a table look-up in a memory of the computer having known information regarding the tissue types and the associated optical axis; and comparing the known information of the associated optical axis properties obtained as a function of depth to the sample with the known information in the table look-up to identify the tissue type.

13. The method as described in claim 1, wherein the directing light to the sample further comprises producing the light over a multiplicity of optical frequencies.

14. The method as described in claim 1, wherein the sample includes a tissue selected from the group consisting of: arterial vessels and plaques, amyloid plaques and neurofibrillary tangles, aneurysms, urethra, tumors, cartilage, cornea, muscle, retina, nerve, skin and tendon.

15. The method as described in claim 1, wherein the sample includes a disease tissue selected from the group consisting of: osteoarthritis, myocardial heart disease, thyroid disease, aneurism, gout, Alzheimer's disease, cancers, tumors, glaucoma, and chronic myeloid leukemia.

16. The method as described in claim 1, wherein the sample includes a tissue subjected to one of the following: burns, wound healing, optical clearing by exogenous chemical agents, or the contractile state of muscle.

* * * * *